US008835714B2

(12) United States Patent
Mittendorf et al.

(10) Patent No.: US 8,835,714 B2
(45) Date of Patent: Sep. 16, 2014

(54) SUGAR AND LIPID METABOLISM REGULATORS IN PLANTS II

(71) Applicants: Volker Mittendorf, Hillsborough, NC (US); Heiko A. Haertel, Berlin (DE); Petra Cirpus, Mannheim (DE)

(72) Inventors: Volker Mittendorf, Hillsborough, NC (US); Heiko A. Haertel, Berlin (DE); Petra Cirpus, Mannheim (DE)

(73) Assignee: BASF Plant Science GmbH, Ludwigshafen (DE)

( * ) Notice: Subject to any disclaimer, the term of this patent is extended or adjusted under 35 U.S.C. 154(b) by 0 days.

(21) Appl. No.: 13/623,212

(22) Filed: Sep. 20, 2012

(65) Prior Publication Data

US 2013/0025001 A1    Jan. 24, 2013

Related U.S. Application Data

(60) Division of application No. 13/103,572, filed on May 9, 2011, now Pat. No. 8,278,506, which is a division of application No. 11/998,203, filed on Nov. 29, 2007, now Pat. No. 7,964,769, which is a continuation of application No. 10/171,404, filed on Jun. 4, 2002, now Pat. No. 7,317,140.

(60) Provisional application No. 60/295,680, filed on Jun. 4, 2001.

(51) Int. Cl.
| *A01H 1/00* | (2006.01) |
| *A01H 5/00* | (2006.01) |
| *A01H 5/10* | (2006.01) |
| *C12N 15/29* | (2006.01) |
| *C12N 15/82* | (2006.01) |
| *C07H 21/04* | (2006.01) |
| *C07K 14/415* | (2006.01) |

(52) U.S. Cl.
CPC .......... *C07K 14/415* (2013.01); *C12N 15/8247* (2013.01)
USPC ........... 800/278; 800/281; 800/295; 800/298; 435/410; 435/419; 435/468; 435/320.1; 536/23.1; 536/23.6

(58) Field of Classification Search
None
See application file for complete search history.

(56) References Cited

U.S. PATENT DOCUMENTS

| 5,444,166 A | 8/1995 | Ecker et al. |
| 5,602,322 A | 2/1997 | Ecker et al. |
| 5,955,650 A | 9/1999 | Hitz |
| 6,084,164 A | 7/2000 | Bidney et al. |
| 6,995,253 B1 | 2/2006 | Innes et al. |
| 7,109,033 B2 | 9/2006 | Harper et al. |
| 7,223,904 B2 * | 5/2007 | Heard et al. ................. 800/295 |

FOREIGN PATENT DOCUMENTS

| EP | 1 033 405 A2 | 9/2000 |
| WO | WO-94/29467 A2 | 12/1994 |
| WO | WO-00/61771 A2 | 10/2000 |
| WO | WO-00/66750 A2 | 11/2000 |
| WO | WO-01/26459 A2 | 4/2001 |
| WO | WO-02/22675 A2 | 3/2002 |
| WO | WO-02/074977 A2 | 9/2002 |

OTHER PUBLICATIONS

Database Genembl, Accession No. AY062851, Nov. 25, 2001, *Arabidopsis thaliana* nucleic acid binding protein-like.*
Sheehy et al, 1988, PNAS, 85:8805-8809.*
Asamizu, et al., Database EST, Accession AV523321, Sep. 1, 2000.
Buhr, T., et al., "Ribozyme Termination of RNA Transcripts Down-Regulate Seed Fatty Acid Genes in Transgenic Soybean", The Plant Journal, (2002), vol. 30, No. 2, pp. 155-163.
Database N Geneseq., Accession AAC48649, Oct. 18, 2000.
Ohlrogge, J., et al., "Fatty Acid Synthesis: From CO2 to Functional Genomics", Biochem. Society Transactions, (2000), vol. 28, No. 6, pp. 567-573.
Yamada et al., Database GenEMBL, Accession AY074284, Apr. 26, 2002.
Vysotskaia, et al., Database Accession No. O80743, Nov. 1, 1998.
Arenas-Huertero, et al., Analysis of *Arabidopsis* Glucose Insensitive Mutants, gin5 and gin6 Reveals a Central Role of the Plant Hormone ABA in the Regulation of Plant Vegetative Development by Sugar, Genes Dev., vol. 14, (2000), pp. 2085-2096.
Beaudoin, et al., "Interactions Between Abscisic Acid and Ethylene Signaling Cascades", Plant Cell, vol. 2000, (2000), pp. 1103-1115.
Brenner, "Regulatory Function of Δ6 Desaturase—Key Enzyme of Polyunsaturated Fatty Acid Synthesis", Adv. Exp. Med. Biol., vol. 83, (1976), pp. 85-101.
Browse, et al., "Fluxes Through the Prokaryotic and Eukaryotic Pathways of Lipid Synthesis in the '16:3' Plant *Arabidopsis thaliana*", Biochemical J., vol. 235, (1986), pp. 25-31.
Cahoon, et al., "Expression of a Coriander Desaturase Results in Petroselinic Acid Production in Transgenic Tobacco", Proc. Natl. Acad. Sci. USA, vol. 89, (1992), pp. 11184-11188.
Cohen, "Signal Integration at the Level of Protein Kinases, Protein Phosphatases and Their Substrates", Trends Biochem. Sci., vol. 17, (1992), pp. 408-413.
Colon-Carmona, et al., "Aux/IAA Proteins Are Phosphorylated by Phytochrome in Vitro", Plant Physiol., vol. 124, (2000), pp. 1728-1738.

(Continued)

*Primary Examiner* — Eileen B O Hara
(74) *Attorney, Agent, or Firm* — Roberte M. D. Makowski

(57) ABSTRACT

Isolated nucleic acids and proteins associated with lipid and sugar metabolism regulation are provided. In particular, lipid metabolism proteins (LMP) and encoding nucleic acids originating from *Arabidopsis thaliana* are provided. The nucleic acids and proteins are used in methods of producing transgenic plants and modulating levels of seed storage compounds. Preferably, the seed storage compounds are lipids, fatty acids, starches or seed storage proteins.

20 Claims, 29 Drawing Sheets

(56) References Cited

OTHER PUBLICATIONS

Frentzen, "Acyltransferases from Basic Science to Modified Seed Oils", Lipids, vol. 100, (1998), pp. 161-166.

Hofgen, et al., "Biochemical and Genetic Analysis of Different Patatin Isoforms Expressed in Various Organs of Potato (*Solanum tuberosum*)", Plant Sci., vol. 66, (1990), pp. 221-230.

Kang & Rawsthorne, "Starch and Fatty Acid Synthesis in Plastids from Developing Embryos of Oilseed Rape (*Brassica napus* L.)", Plant J., vol. 6, (1994), pp. 795-805.

Kuo, et al, "Okadaic Acid, a Protein Phosphatase Inhibitor; Blocks Calcium Changes, Gene Expression, and Cell Death Induced by Gibberellin in Wheat Aleurone Cells", Plant Cell, vol. 8, (1996), pp. 259-269.

Millar, et al., "All Fatty Acids Are Not Equal: Discrimination in Plant Membrane Lipids", Trends Plant Sci., vol. 5, (2000), pp. 95-101.

Ogas, et al., "Cellular Differentiation Regulated by Gibberellin in the *Arabidopsis thaliana* Pickle Mutant", Science, vol. 277, (1997), pp. 91-94.

Ogas, et al., "PICKLE is a CHD3 Chromatin-Remodeling Factor That Regulates the Transition from Embryonic to Vegetative Development in *Arabidopsis*", Proc. Natl. Acad. Sci. USA, vol. 96, (1999), pp. 13839-13844.

Ohlrogge & Browse, "Lipid Biosynthesis", Plant Cell, vol. 7, (1995), pp. 957-970.

Plaxton, "The Organization and Regulation of Plant Glycolysis", Annu. Rev. Plant Physiol. Plant Mol. Biol., vol. 47, (1996), pp. 185-214.

Ritchie & Gilroy, "Calcium-Dependent Protein Phosphorylation May Mediate the Gibberellic Acid Response in Barley Aleurone", Plant Physiol., vol. 116, (1998), pp. 765-776.

Shanklin & Cahoon, "Desaturation and Related Modifications of Fatty Acids", Annu. Rev. Plant Physiol. Plant Mol. Biol., vol. 49, (1998), pp. 611-641.

Topfer, et al., "Modification of Plant Lipid Synthesis", Science, vol. 268, (1995), pp. 681-686.

Van De Loo, et al., "An Oleate 12-Hydroxylase from *Ricinus communis* L. is a Fatty Acyl Desaturase Homolog", Proc. Natl. Acad. Sci. USA, vol. 92, (1995), pp. 6743-6747.

Van De Loo, et al., "Unusual Fatty Acids" in Lipid Metabolism in Plants, TS Moore Jr., CRC Press, (1993), pp. 91-126.

Voelker, "Plant ACYL-ACP Thioesterases: Chain-Length Determining Enzymes in Plant Fatty Acid Biosynthesis", Genetic Engineering Ed.: Setlow, vol. 18, (1996), pp. 111-133.

Zhou, et al., "Glucose and Ethylene Signal Transduction Crosstalk Revealed by an *Arabidopsis* Glucose-Insensitive Mutant", Proc. Natl. Acad. Sci. USA, vol. 95, (1998), pp. 10294-10299.

Abel, et al., J. Mol. Biol., vol. 251, (1995), pp. 533-549.

Kader, Annual Review of Plant Physiology and Plant Molecular Biology, vol. 47, (1996), pp. 627-654.

\* cited by examiner

Figure 1A

SEQ ID NO:1, Nucleotide sequence of the open reading frame of pk002b

ATGGTTCGTCCTGGATTCATTATGCGGCCGCCTGGTACAATCGGTGCTGTTCAAC
TAGCACCACGACCCCTTATTCCAGGAATGCCTGGTCTCCGTCCTGTAATGCCTCCT
ATGGTTAGACCGGCTTCTCTTCCTTTTGTAACACCTGCAGAAAAGCCCCAGACCA
CAATTTACATTGGCAAGATAGCTACCGTGGAAAATGACTTTATGATGTCTATTCT
TGAGTTTTGTGGCCATGTCAAAAGCTGTTTACGTGCGGAAGATCCTACCACCAAG
AAACCTAAAGGTTTTGGATTCTATGAATTTGAATCAGCTGAAGGGATTCTCCGCG
CAATACGCCTGCTGACCCAACGTACTATAGATGGACAAGAGCTTTTGGTGAATGT
TAATCAAGCAACAAGGAGTATTTGCTAAAATATGTTGAGAAGAAAATAGAGAC
TGCAAAGAAAGCCAAGGAAAGTCAAGGAACCAAAGAGAACCAAGCTGAAGGTC
CTGAGAGTGAGCAAGACAAGCTTGAGAGTGCTGATAATGAGACAGGGAAGGAT
GGAGAATCGAAGATTAAAGAAAACATCGATATTGCGAATTCTGCTGTCCTAACT
GATGAAGAAGGGAAGCAGACAGAGAGGCTATGGAAAAGATTGAAACTGCTAT
TGAAGAAAGGTTAAAGTCCAACCCTTTGCCTCCTCCACCACCACCACCTGCTGAT
GGTTCAGGCATGGAATTTGCTTTCAAATCTAAGGATGGTGACTCCAACACTGACG
TAGCTAGGAGTGATGCCGCAGCAAATGATGTTGAGACTTCTGGAGAACACAATA
GGCCTGACACAAGCTCACCTGATTGGAGTAAGAGAAATGACCGAAGAGGCAGAG
AAAGAGGTGAGAAGGAGCAAGAAATGGATAGATACGAGAGGGAGGCTGAAAGA
GAACGGTCAAGGAAAGAGAGAGAGCAAAGGAGGAAACTTGAGGATGCAGAGCG
TGCTTACCAGACTCGTCTTCGACAATGGGAACGAAGAGAAAGAGAAAAGGAGAA
GGAACGACAGTACGAGAAGGAGAAAGAGAAAGAGAAAGAGCGCAAGAGGAAA
AAGGAAATCCGCTATGAGGAAGAAGAGGAAGAAGACGATGATGATTCAAGAAG
AAGATGGCATAGGGCTGCATTAGATGAGAGAAGAAGACGACAACTAAGAGAAA
AGGAGGATGACTTAGCTGATAGATTGAAAGAAGAGGAAGAGGTTGCTGAGGCG
AAGAGGAGTGCCGAGGAGCAAAATTTGCAGCAACAGCAATTAGATGCCTTAAGA
ATCCTATCGGGACAGGCAGCTATTGGAAGCGAAACGGTTCAGACATCACCTATT
GAAAATGATCACAAGGCAACTCTCCAAACTGTCGGTGAATCTGCCAATGAGCAC
CATGCAGCAGATTTTGAAGAAATGGTTCTGGTAATGAATCGATGGCTATCGATA
ATAATAGTGGATCAGAGGCACATGCTCCCTCAAAGAAATTAGGATTTGGGCTTGT
GGGATCCGGAAAGCGAACTTCTGTGCCTTCTGTTTTCTATGAGGAGGATGAAGAT
GAAGCACGTAAGGCTAAAAAGATGAAACCTTTGGTTCCTATAGATTACTCAACC
GAGGAACAAGAGGCTGTGGCCCATGGTGGCTCAGGGAATACACCACCTCATTTG
GCTTTAGCCGCTGAATTTGCAAAACGAATTTCGAGTACCAATCCCAAGGAAGAG

Figure 1A Continued

ACGATAGAAACCGAAAAACAAAGGAGCAGACGTTCTCATGATAAGGCAAGCCA
CCGGGACAGGGAAAGGGAAAGGGAAAGGGACAGGGACAGGGATAGAGTCAGG
GACCGAGGTGACGGGCATAGTGGTCCCACCAAAGACGCCAAAGAGTCTGGAAAA
GCAAAGATAATTGATACTAAGTTTCTGGATGCGAAACAATTGATAGATACAATCC
CAAAGACAAAGGAAGATTTATTTTCTTACGAGATAAACTGGGCTATGTATGACA
AGCACCAAGTGCACGAAAGAATGAGACCATGGATCTCAAAGAAAATTATGGAGT
TTCTCGGAGAAGAGGAAGCCACTCTGGTAGATTTCATCGTGTCAAACACTCAACA
ACACGTGCAGGCGTCTCAGATGCTTGAGCTGTTGCAATCAATTCTAGACGAAGAA
GCTGAGATGTTTGTGCTGAAGATGTGGAGAACGCTCATCTTTGAGATCAAGCGGG
TTGAAGCTGGAGTCCCGGTAAAATCCAAAGCCTGA

Figure 1B

SEQ ID NO:2, Amino acid sequence of the open reading frame of pk002b

MVRPGFIMRPPGTIGAVQLAPRPLIPGMPGLRPVMPPMVRPASLPFVTPAEKPQTTIYI
GKIATVENDFMMSILEFCGHVKSCLRAEDPTTKKPKGFGFYEFESAEGILRAIRLLTQ
RTIDGQELLVNVNQATKEYLLKYVEKKIETAKKAKESQGTKENQAEGPESEQDKLES
ADNETGKDGESKIKENIDIANSAVLTDEEREADREAMEKIETAIEERLKSNPLPPPPPP
PADGSGMEFAFKSKDGDSNTDVARSDAAANDVETSGEHNRPDTSSPDWSKRNDRR
GRERGEKEQEMDRYEREAERERSRKEREQRRKLEDAERAYQTRLRQWERREREKE
KERQYEKEKEKEKERKRKKEIRYEEEEEEDDDDSRRRWIIRAALDERRRRQLREKED
DLADRLKEEEEVAEAKRSAEEQNLQQQQLDALRILSGQAAIGSETVQTSPIENDHKA
TLQTVGESANEHHAADFEENGSGNESMAIDNNSGSEAHAPSKKLGFGLVGSGKRTS
VPSVFYEEDEDEARKAKKMKPLVPIDYSTEEQEAVAHGGSGNTPPHLALAAEFAKRI
SSTNPKEETIETEKQRSRRSHDKASHRDRERERERDRDRDRVRDRGDGHSGPTKDAK
ESGKAKIIDTKFLDAKQLIDTIPKTKEDLFSYEINWAMYDKHQVHERMRPWISKKIME
FLGEEEATLVDFIVSNTQQHVQASQMLELLQSILDEEAEMFVLKMWRTLIFEIKRVEA
GVPVKSKA

Figure 2A

SEQ ID NO:3, Nucleotide sequence of the open reading frame of pk020b

GTGCTGAAAAAGAAGAAACCCATACTTACTGACGAGCATTTCGTAGATGGTCGG
TTTGGTTCGATGTTCCAAAATCCGGACTTCCAAATTGATAAGGACTCATATGAAT

Figure 2A Continued

ATGGTGTCCTACACCCTGTTGCTTCTTCGAAGAAGCAACCTTCTCTGTTAGATGA
ACACTTTGAAGCTGTATCAGATGATGACGAGAACAGTGATTCTGATGCATCACAG
CCTTCAGATGACGAGGCCGACGATGGAGACGCAACTAGGCCAAGCAAGAAAGC
GAGAACTCCGAAGTTGTATGAAGTGAAAGATGAGCGGCATGCCGCAGCTTATCA
CAACCGCACTTCACTGGCTAAAGAAGATAGTCTTCCTATGGGCGAGCGTGTCAAG
GCTATAGAGAACCGGCGTGGCAACTTTGGAGGCTCGAAAGATATCAAATTCGGT
CCTGGAGGATCACGGGAGTTTTCTTTCAAGGCGAGAGGGTCATCAAAGTACAAA
GAAGATAGAGACGATGAGTATGAAGATGGGCAAAGAAACAAGAGGAGAGGAGT
TCAGTCTCTTGGACTGAAATCAACAAATATTAGAGGCGGTTTCAGAGGTAGAGG
AGGTGGTGGTTTTAGAGGGAGAGGAGGCGGCGGTTCCCGGGGAAAAGGTGGCCG
TGGTGGTGGGCGTGGAAGAGGCCGGCAATGA

Figure 2B

SEQ ID NO:4, Amino acid sequence of the open reading frame of pk020b

VLKKKKPILTDEHFVDGRFGSMFQNPDFQIDKDSYEYGVLHPVASSKKQPSLLDEHF
EAVSDDDENSDSDASQPSDDEADDGDATRPSKKARTPKLYEVKDERHAAAYHNRTS
LAKEDSLPMGERVKAIENRRGNFGGSKDIKFGPGGSREFSFKARGSSKYKEDRDDEY
EDGQRNKRRGVQSLGLKSTNIRGGFRGRGGGGFRGRGGGGSRGKGGRGGGRGRGR
Q

Figure 3A

SEQ ID NO:5, Nucleotide sequence of the open reading frame of pk033

ATGGAGCAGATGATATTCATTAGAAAAGACGACAAAGTAGAGGTTTTTTCTGAA
GAAGAAGAGTTAAAAGGGTCTTATTACAGAGCGATTCTGGAAGATAATCCAACG
AAATCAGGACACAATAAGCTTAAAGTTCGTTACTTGACGCAGCTCAATGAACAC
CGTTTGGCTCCTTTAACGGAATTCGTCGATCAGAGGTTCATTCGTCCTGTCCCGTC
GGAGGATGTGAACGACGGCGTCGTTTTTGTAGAAGGCTTGATGGTCGACGCTTAT
CTCAAAGATGGGTGGTGGACTGGTGTGGTGGTAAAAACAATGGAGGATGAGAAG
TTTTTGGTTTACTTCGATTGCCCACCAGACATTATTCAGTTTGAGAAAAAGAAATT
GAGGGTTCATCTTGATTGGACCGGCTTCAAATGGATCCGACCTGATAATAAGGAA
TTGGTCAAGTCTGTTTTTAGTTGCGGGACAATGGTGGAATTGAGATTTGATTGTG
CTTGGATTCCGGTAATTGTCATTAAGGAGTTGGAGAAGGACAAGAGGTTTCTTGT

Figure 3A Continued

```
CAAGTACTGGAATAAGTCCTATAGCTGCCGGGAATCGAAAAATTTAATTGTTGAT
TCCCTAAGACTAAGGCCTATGCAGCCTCCTTTATCTGTTGGAAAGTATGAATTGC
TGGATCATGTAGAGGCGTTAGTGGTTTTGAATGGCGTCAAGGTGTGGTCAGGGG
AATTGTCTTTGAGGGAAGGTACATGGTAAGTTTCGGGGCAACAAAGGAGGCATC
GCAATTTAATCACTCTGATATTAGGCCTCCAATGGAGTGGGAAGATGGAGTTTGG
CATAAAAGAACAAAGCCAAAACGCCAGAAAGAAACTTCTTTAGACGGCAACAG
AAATGTGCAGACAAAGGAACCACCGGGAAATGAGATGGCTGATGATGTGAAAA
AAGAATCTGGTTTACCTATAACCCTGGGGGTAACTGCAACAAAGAACAAAACCC
AAGGAAAGGTATCCCCTGTGCCAATGAAGAATGGCTTTGGAAATGAGTCAACTC
GAGAGAAGATGCCTGAGGAGCCTAAGATCAAATATTATACTCGAAAGAGGAAAA
GAGGAGGTCTAAAGCTCAATTCATACATCAATAAGACTGTGTTATCCTCGGATCG
GACCCCCAATGTGGTGAAGAATTCTGCTTCTAATGCTGAGGAAAACCATGCAAA
ACACACAATAATGGTTTTGCCTTTTGCAAAGAAGTCACCGGTCTGGAAGACTTAT
GAATCACTGGAGGTCTTCAAAAGTGTATCACACAGTCTTCATTTCAGCCCATTGT
TTGAGACTAAGCAAGATTTCCGTGAAGGGTATGCAATAGGTATGATGGTGACTTA
TTTTGGGTTACTGGAGAAATTTAAAGATCTTGAAGCCGACGTTCCTGTAAGCCAA
CTAAATAGCCTTAAAGATTCATTTTCGGAGCTCGAGAAACATGGCTTCAATGTTA
CAACTCCATTATCACGGATCGACAAGCTGTCAGCACTCAAAGATAGACAACTAT
ATATAATGGAGGAACTAAAAGGTTTTGACAAGGAGATGACAAATGAATTTAGCA
AGGCTAAACAAGAGTTTGATGACATGGAACAAAAGATTCTTGAGGTGAAACACA
AGATTATCGAGCTGCAGAGGCAAGAAGCTGCTCTAAAAGAACAAAAGGAAGCA
GAAAAAGAACAGAAAGATGCAGCCTGGAAAAAGATATGTCAGATGGAGTCATG
CGCAAAAGATCTCAATGTAGAGCTTGAAGATGTGGAGTTTGAGTTTGAGACAATT
TTGTCGGCTCCTTGGTAA
```

Figure 3B

SEQ ID NO:6, Amino acid sequence of the open reading frame of pk033

MEQMIFIRKDDKVEVFSEEEELKGSYYRAILEDNPTKSGHNKLKVRYLTQLNEHRLA
PLTEFVDQRFIRPVPSEDVNDGVVFVEGLMVDAYLKDGWWTGVVVKTMEDEKFLV
YFDCPPDIIQFEKKKLRVHLDWTGFKWIRPDNKELVKSVFSCGTMVELRFDCAWIPVI
VIKELEKDKRFLVKYWNKSYSCRESKNLIVDSLRLRPMQPPLSVGKYELLDHVEAFS
GFEWRQGVVRGIVFEGRYMVSFGATKEASQFNHSDIRPPMEWEDGVWHKRTKPKR
QKETSLDGNRNVQTKEPPGNEMADDVKKESGLPITLGVTATKNKTQGKVSPVPMKN

Figure 3B Continued

GFGNESTREKMPEEPKIKYYTRKRKRGGLKLNSYINKTVLSSDRTPNVVKNSASNAE
ENHAKHTIMVLPFAKKSPVWKTYESLEVFKSVSHSLHFSPLFETKQDFREGYAIGMM
VTYFGLLEKFKDLEADVPVSQLNSLKDSFSELEKHGFNVTTPLSRIDKLSALKDRQLY
IMEELKGFDKEMTNEFSKAKQEFDDMEQKILEVKHKIIELQRQEAALKEQKEAEKEQ
KDAAWKKICQMESCAKDLNVELEDVEFEFETILSAPW

Figure 4A

SEQ ID NO:7, Nucleotide sequence of the open reading frame of pk037

ATGGCTATGGTAGATGAACCGTTGTATCCCATTGCTGTGCTTATAGATGAGCTTA
AGAATGATGATATTCAGCTTCGTTTGAACTCGATCCGTCGCTTATCTACTATAGCT
CGTGCTCTTGGAGAGGAGCGTACAAGGAAGGAGTTAATCCCTTTTTTGAGTGAGA
ATAGTGACGATGACGATGAGGTGCTTCTTGCAATGGCTGAGGAGTTAGGAGTTTT
TATTCCGTTTGTTGGAGGAATTGAGTTTGCGCATGTTCTTCTTCCTCCTTTGGAAT
CTCTATGTACTGTTGAAGAGACTTGTGTGAGAGGAAAAGCTGTGGAATCGCTTTG
TAAGATTGGATCTCAGATGAAAGAGAATGATCTTGTTGAATCTTTTGTTCCTCTTG
TGAAGAGGTTAGCGGGTGGTGAATGGTTTGCAGCAAGAGTTTCTGCATGTGGTAT
ATTTCATGTTGCATACCAAGGTTGCACTGATGTTTTGAAGACTGAGTTACGGGCT
ACTTATAGCCAGTTGTGCAAAGATGATATGCCAATGGTGCGAAGAGCTGCTGCAT
CTAACCTGGGGAAATTTGCTACAACTGTCGAGTCTACCTTTTTGATTGCTGAGAT
CATGACTATGTTCGATGATCTTACTAAAGATGACCAAGATTCTGTGAGACTATTG
GCTGTTGAAGGGTGTGCAGCTCTTGGAAAGTTGTTGGAACCTCAGGATTGTGTTG
CACGCATTTTACCTGTTATTGTTAATTTCTCTCAGGATAAATCTTGGAGGGTGCGC
TACATGGTTGCAAATCAGCTATATGAACTTTGTAAGGCAGTGGGTCCTGATTGCA
CGAGGACGGATTTGGTTCCAGCATATGTAAGATTGCTAAGGGACAATGAGGCTG
AAGTGCGAATAGCAGCAGCGGGAAAAGTGACCAAGTTCTGTCGGCTTTTGAATC
CAGAGCTTGCGATTCAGCACATCCTTCCTTGTGTGAAGGAATTATCATCGGATTC
TTCTCAACATGTCCGCTCTGCTCAGCTTCAGTAATAATGGGGATGGCTCCTATCC
TTGGGAAGGACTCAACCATTGAGCATCTGTTACCAATTTTTCTTTCCCTTTTGAAA
GATGAATTTCCTGATGTGCGCCTTAACATCATAAGCAAGTTAGATCAAGTCAACC
AGGTTATTGGAATTGATCTACTATCTCAATCCTTGTTACCGGCCATTGTAGAACTT
GCTGAGGATCGGCACTGGAGAGTCCGACTTGCAATAATAGAGTATGTTCCACTGT
TGGCCAGCCAGTTAGGTATAGGATTTTTCGATTACAAGCTCGGAGCCCTTTGCAT

Figure 4A Continued

GCAATGGCTGCAAGACAAGGTCTACTCTATCCGCGAAGCTGCAGCTGCAGCAAA
CAACCTAAAGCGCCTCGCAGAGGAGTTTGGTCCTGAATGGGCAATGCAGCACTT
AGTTCCCCAGGTATTGGACATGGTCAACAATCCGCACTACCTACACAGGATGATG
GTTCTACGCGCAATATCTCTCATGGCGCCTGTAATGGGATCAGAAATCACATGCT
CTAAGTTTCTTCCTGTGGTTGTTGAAGCATCAAAAGACAGAGTTCCAAACATCAA
GTTCAACGTTGCCAAACTTCTGCAATCCCTCATCCCCATAGTCGACCAATCAGTG
GTGGACAAAACAATCCGTCAGTGTTTGGTGGACCTGAGCGAAGACCCTGATGTT
GATGTTCGTTATTTTGCAAATCAAGCACTTAATTCCATCGATGGTTCCACAGCAG
CACAATCCTGA

Figure 4B

SEQ ID NO:8, Amino acid sequence of the open reading frame of pk037

MAMVDEPLYPIAVLIDELKNDDIQLRLNSIRRLSTIARALGEERTRKELIPFLSENSDD
DDEVLLAMAEELGVFIPFVGGIEFAHVLLPPLESLCTVEETCVRGKAVESLCKIGSQM
KENDLVESFVPLVKRLAGGEWFAARVSACGIFHVAYQGCTDVLKTELRATYSQLCK
DDMPMVRRAAASNLGKFATTVESTFLIAEIMTMFDDLTKDDQDSVRLLAVEGCAAL
GKLLEPQDCVARILPVIVNFSQDKSWRVRYMVANQLYELCKAVGPDCTRTDLVPAY
VRLLRDNEAEVRIAAAGKVTKFCRLLNPELAIQHILPCVKELSSDSSQHVRSALASVI
MGMAPILGKDSTIEHLLPIFLSLLKDEFPDVRLNIISKLDQVNQVIGIDLLSQSLLPAIVE
LAEDRHWRVRLAIIEYVPLLASQLGIGFFDYKLGALCMQWLQDKVYSIREAAAAAN
NLKRLAEEFGPEWAMQHLVPQVLDMVNNPHYLHRMMVLRAISLMAPVMGSEITCS
KFLPVVVEASKDRVPNIKFNVAKLLQSLIPIVDQSVVDKTIRQCLVDLSEDPDVDVRY
FANQALNSIDGSTAAQS

Figure 5A

SEQ ID NO:9, Nucleotide sequence of the open reading frame of pk038

ATGACCACGTTATTCCTCCTTATTGCTCTATTCATCACAACCATCCTCAACCCAAC
AAGTGGAGAATCAGTAGGTGTATGCTATGGAATGATGGGGAACAACCTTCCTTCT
CAATCAGACACAATCGCTCTCTTTAGACAAAACAACATCCGACGTGTTAGACTCT
ACGATCCAAACCAAGCCGCTTTAAACGCTCTTAGAAACACGGGTATCGAAGTCA
TCATCGGCGTTCCAAACACCGATCTTCGTTCACTCACTAACCCTTCTTCCGCTAGA
TCATGGCTCCAAAACAACGTCCTCAACTATTACCCCGCCGTTAGCTTCAAGTACA

Figure 5A Continued

TCGCCGTAGGTAACGAAGTATCTCCGTCGAACGGCGGTGATGTTGTGCTCCCTGC
CATGCGTAACGTTTACGATGCTCTAAGAGGTGCAAATCTTCAAGATCGTATTAAA
GTTTCTACCGCCATTGATATGACTTTGATTGGAAACTCTTTCCCTCCTTCCTCCGG
AGAGTTTCGTGGTGACGTTAGATGGTATATCGATCCCGTCATCGGGTTTCTTACG
AGTACGAACTCAGCGTTACTAGCCAACATCTATCCTTACTTCAGCTACGTTGACA
ATCCACGTGACATATCTCTCTTACGCTCTCTTCACTTCTCCTTCCGTCGTCGTAT
GGGACGGCTCTCGTGGCTACCAAAACCTCTTTGACGCTTTACTTGACGTTGTTTAC
TCTGCCGTTGAACGCTCAGGCGGTGGATCTCTCCCAGTGGTTGTTTCCGAGAGCG
GATGGCCTTCTAACGGTGGAAACGCCGCGAGTTTCGATAACGCGCGAGCTTTTA
CACGAATCTTGCGTCGCGTGTGAGAGAGAACAGAGGAACACCGAAGAGACCTGG
AAGAGGAGTGGAAACGTATTTGTTCGCTATGTTTGATGAGAATCAAAAGAGTCCT
GAGATCGAGAAGAATTTTGGTTTGTTTTTTCCTAATAAACAACCAAAATTTCCGA
TCACATTCTCTGCCGCGAGAGACGGTACGGCGGTTGAGTGA

Figure 5B

SEQ ID NO:10, Amino acid sequence of the open reading frame of pk038

MTTLFLLIALFITTILNPTSGESVGVCYGMMGNNLPSQSDTIALFRQNNIRRVRLYDPN
QAALNALRNTGIEVIIGVPNTDLRSLTNPSSARSWLQNNVLNYYPAVSFKYIAVGNE
VSPSNGGDVVLPAMRNVYDALRGANLQDRIKVSTAIDMTLIGNSFPPSSGEFRGDVR
WYIDPVIGFLTSTNSALLANIYPYFSYVDNPRDISLSYALFTSPSVVVWDGSRGYQNL
FDALLDVVYSAVERSGGGSLPVVVSESGWPSNGGNAASFDNARAFYTNLASRVREN
RGTPKRPGRGVETYLFAMFDENQKSPEIEKNFGLFFPNKQPKFPITFSAARDGTAVE

Figure 6A

SEQ ID NO:11, Nucleotide sequence of the open reading frame of pk042a

GTGTCCATCACTGGAAAGGGAGTGAAAGCCACCGTTAAAGGTAGAGAGATTATG
GTGGGGAACAAGAATCTGATGAATGATCATAAAGTTATTATTCCAGATGATGCTG
AAGAGTTGCTAGCTGACTCTGAAGATATGGCCCAGACCGGAATTCTTGTCTCCAT
AAACAGTGAACTGATTGGAGTTTTGTCTGTTTCGGATCCTCTAAAACCGAGTGCT
CGAGAAGCCATCTCCATTCTAAAATCCATGAATATCAAAAGCATCATGGTAACTG
GTGGCAACTGGGGAACAGCAAACTCAATTGCTAGAGAAGTCGGTATCGACTCTG

Figure 6A Continued

TTATCGCAGAAGCTAAACCTGAGCAAAAAGCAGAGAAAGTCAAGGAATTACAGG
CTGCGGGACATGTTGTGGCAATGGTAGGTGACGGAATCAATGACTCACCGGCTCT
CGTGGCAGCGGATGTAGGTATGGCGATAGGTGCAGGAACAGACATTGCTATAGA
AGCAGCGGATATAGTTCTGATGGAAAGCAACTTAGAAGATGTGATCACAGCCAT
TGATCTTTCAAGGAAAACGTTCTCAAGAATCCGTCTCAACTACGTATGGGCTCTC
GGGTATAACCTCATGGGGATACCGATCGCTGCGGGAGTGCTTTTCCCAGGGACAC
GTTTCAGGTTGCCTCCATGGATTGCAGGTGCTGCAATGGCTGCTTCTTCTGTTAGT
GTTGTGTGTTGCTCTCTCTTGCTTAAGAACTACAAGCGACCTAAGAAGCTTGATC
ATCTGGAGATTCGGGAGATTCAGGTGGAGCGAGTTTAA

Figure 6B

SEQ ID NO:12, Amino acid sequence of the open reading frame of pk042a

VSITGKGVKATVKGREIMVGNKNLMNDHKVIIPDDAEELLADSEDMAQTGILVSINS
ELIGVLSVSDPLKPSAREAISILKSMNIKSIMVTGGNWGTANSIAREVGIDSVIAEAKPE
QKAEKVKELQAAGHVVAMVGDGINDSPALVAADVGMAIGAGTDIAIEAADIVLMES
NLEDVITAIDLSRKTFSRIRLNYVWALGYNLMGIPIAAGVLFPGTRFRLPPWIAGAAM
AASSVSVVCCSLLLKNYKRPKKLDHLEIREIQVERV

Figure 7A

SEQ ID NO:13, Nucleotide sequence of the open reading frame of pk053b

GTGGCCATGGAAGGAGAATTTCAGGATGAGCTTGTGGTTGTTGGAGATGGAGTG
GATTCAGCTTCTTTGATTATGGCCTTAAGGAAGAAAGCATGTCATGTCACTCTTG
AGACTCTTGAAGAAGTGAAGAAGCCACAGGTCGAAGAGAAGTCTATTACACCGC
ATTGCTGCATAGCTCAATGTCCTGTGGTTAGCAATGAGCAGCCAAGGCCTGAGGT
TTATAGAATAGTGCATGATTCTTATGGTCCAACCACTGGGTGCTTAGTTATGTAA

Figure 7B

SEQ ID NO:14, Amino acid sequence of the open reading frame of pk053b

VAMEGEFQDELVVVGDGVDSASLIMALRKKACHVTLETLEEVKKPQVEEKSITPHC
CIAQCPVVSNEQPRPEVYRIVHDSYGPTTGCLVM

Figure 8A

SEQ ID NO:15, Nucleotide sequence of the open reading frame of pk060

ATGGTCTTGATTACTAAGATGTCTCTCTCTTTCTACATCATTCATCTTCTCATTTTC
TCCTTGATTTCCACTTGTGTTGTCTCCAACCAGGCCGAGGATAATCTTCTTCAAGG
CCTAAACAGCTACCGAACTGCTCAAAGAGTTCCTCCATTTGCCAAGAATGAGAA
GGCTGATTGTGTGGCTGATGAGATCGCCGACAAGCTCGAAGATCAGCCATGCAC
AAACCACACCACAGCGAGCACGGTTACTCCTGGCTCGGTACCTCCACGGCTGAC
GAACTACCAGGACATTCTCTCTGAATGCAAAATCGACCCAAACACTACCCGTGAC
GGATTGATCTTACCTGTCTGTATCCCTAACCGGATCCCGACTTTGGCTTTAACTAA
TTACACCCAAACTGGTTATGCTCGGTATCTTAATGATTCGAGGTATGTCGGGGCT
GGTGTTGGGTCGGAGAAAGAGTGGATGGTGGTTGTATTGACGACAAGTACTCCA
GGTGGAAGCTTTACAGCTGGTGTTGCTGCTGGCAAGGCGACGTCTGTGAGAGTA
ATGGCTGGTTTAGGGCTAATGGGGTTGTTGTTTAGTTGCCTTGTGCTCTTCTGA

Figure 8B

SEQ ID NO:16, Amino acid sequence of the open reading frame of pk060

MVLITKMSLSFYIIHLLIFSLISTCVVSNQAEDNLLQGLNSYRTAQRVPPFAKNEKADC
VADEIADKLEDQPCTNHTTASTVTPGSVPPRLTNYQDILSECKIDPNTTRDGLILPVCI
PNRIPTLALTNYTQTGYARYLNDSRYVGAGVGSEKEWMVVVLTTSTPGGSFTAGVA
AGKATSVRVMAGLGLMGLLFSCLVLF

Figure 9A

SEQ ID NO:17, Nucleotide sequence of the open reading frame of pk063b

ATGGAGAAAGTGACCAACTCAGACTTGAAATCCTCTGTTGATGGTGGCGTTGTTG
ATGTGTATGGAGAAGATTCAGCCACCATTGAGCACAACATAACTCCTTGGTCTCT
CTCTGTTTCTAGTGGATATTCATTGCTGAGAGATCCTCGCTACAACAAAGGACTT
GCTTTCACTGAGAAAGAGAGAGACACTCATTACTTGCGTGGTCTTCTCCCTCCAG
TTGTTCTTGATCAAAAGCTTCAGGAGAAGAGGCTGTTGAACAATATCCGACAATA
TCAATTCCCATTACAAAAGTACATGGCTCTGACAGAACTTCAGGAAAGAAACGA
GAGACTGTTTTACGAGCTATTGATAGATAATGTTGAGGAGCTACTTCCTATTGTTT
ATACTCCAACTGTTGGTGAAGCTTGTCAGAAATTTGGAAGTATTTTCAGGCGACC
TCAGGGTTTATTCATCAGTTTAAAAGACAAGGGAAAGATTCTAGATGTGTTAAAG

Figure 9A Continued

AACTGGCCTGAAAGGAACATACAGGTTATTGTTGTTACTGACGGTGAAAGGATTT
TAGGATTAGGAGATCTTGGATGTCAGGGGATGGGTATACCGGTTGGTAAGTTGG
CGTTATATTCAGCACTTGGAGGTGTTCGTCCTTCAGCGTGTTTACCTGTCACCATT
GATGTGGGAACAAACAATGAGAAACTGTTGAATGATGAGTTCTACATAGGACTC
AGGCAAAAGAGAGCAACGGGACAGGAATATAGTGAACTCTTGAATGAATTCATG
AGTGCTGTGAAACAGAACTATGGTGAAAAGTTCTTATTCAGTTTGAAGATTTTG
CTAATCATAATGCCTTTGAGTTGCTTGCAAAATACAGCGATACTCATCTCGTCTTC
AACGATGATATACAGGGGACAGCATCAGTTGTTTTAGCAGGATTAGTTTCCGCAC
AGAAGTTAACGAATAGCCCACTTGCAGAGCATACCTTCCTCTTTCTTGGTGCTGG
TGAAGCTGGAACTGGAATAGCAGAACTCATAGCTCTCTATATGTCAAAACAGAT
GAATGCTTCGGTAGAGGAAAGCCGCAAGAAAATCTGGCTTGTTGATTCCAAGGG
ATTGATTGTTAACTCCCGCAAAGATTCACTTCAAGACTTTAAGAAACCATGGGCT
CATGAACATGAACCAGTCAAAGACCTCTTAGGTGCTATCAAGGCAATAAAACCG
ACTGTTCTGATTGGATCTTCTGGCGTTGGACGGTCTTTTACAAAAGAAGTGATAG
AAGCCATGTCCTCCATTAATGAGAGACCACTGATAATGGCTCTCTCTAACCCCAC
AACACAATCTGAATGTACAGCCGAAGAAGCTTATACTTGGAGTAAGGGCCGTGC
CATTTTTGCTAGTGGAAGCCCTTTTGATCCAGTTGAGTATGAAGGAAAGGTGTTT
GTATCTACACAGGCGAACAATGCGTACATATTCCCGGGCTTTGGACTTGGTTTGG
TTATCTCTGGAGCAATACGGGTACATGACGATATGCTTCTAGCTGCTGCTGAGGC
ATTAGCTGGACAAGTAAGCAAAGAGAACTATGAGAAAGGAATGATATATCCTTC
ATTCTCTTCCATCCGGAAAATATCAGCTCAGATTGCAGCCAATGTAGCAACTAAG
GCGTATGAACTAGGATTGGCAGGGCGGCTTCCACGGCCGAAAGATATTGTCAAA
TGTGCAGAGAGTAGCATGTACAGCCCCACATACCGTCTCTACCGTTGA

Figure 9B

SEQ ID NO:18, Amino acid sequence of the open reading frame of pk063b

MEKVTNSDLKSSVDGGVVDVYGEDSATIEHNITPWSLSVSSGYSLLRDPRYNKGLAF
TEKERDTHYLRGLLPPVVLDQKLQEKRLLNNIRQYQFPLQKYMALTELQERNERLFY
ELLIDNVEELLPIVYTPTVGEACQKFGSIFRRPQGLFISLKDKGKILDVLKNWPERNIQ
VIVVTDGERILGLGDLGCQGMGIPVGKLALYSALGGVRPSACLPVTIDVGTNNEKLL
NDEFYIGLRQKRATGQEYSELLNEFMSAVKQNYGEKVLIQFEDFANHNAFELLAKYS
DTHLVFNDDIQGTASVVLAGLVSAQKLTNSPLAEHTFLFLGAGEAGTGIAELIALYM
SKQMNASVEESRKKIWLVDSKGLIVNSRKDSLQDFKKPWAHEHEPVKDLLGAIKAIK

Figure 9B Continued

PTVLIGSSGVGRSFTKEVIEAMSSINERPLIMALSNPTTQSECTAEEAYTWSKGRAIFA
SGSPFDPVEYEGKVFVSTQANNAYIFPGFGLGLVISGAIRVHDDMLLAAAEALAGQV
SKENYEKGMIYPSFSSIRKISAQIAANVATKAYELGLAGRLPRPKDIVKCAESSMYSPT
YRLYR

Figure 10A

SEQ ID NO:19, Nucleotide sequence of the open reading frame of pk064

ATGGCGTCAGACAAACAAAAGGCGGAGAGAGCCGAGGTTGCGGCGAGGCTAGC
GGCTGAGGACTTGCATGACATTAACAAATCCGGTGGTGCTGATGTCACAATGTAT
AAGGTGACGGAGAGAACAACTGAACATCCACCGGAGCAAGATAGGCCCGGTGT
GATAGGTTCAGTGTTCAGGGCTGTCCAAGGAACGTATGAGCATGCGAGAGACGC
TGTAGTTGGAAAAACCCACGAAGCGGCTGAGTCTACCAAAGAAGGAGCTCAGAT
AGCTTCAGAGAAAGCGGTTGGAGCAAAGGACGCAACCGTCGAGAAAGCTAAGG
AAACCGCTGATTATACTGCGGAGAAGGTGGGTGAGTATAAAGACTATACGGTTG
ATAAAGCTAAAGAGGCTAAGGACACAACTGCAGAGAAGGCGAAGGAGACTGCT
AATTATACTGCGGATAAGGCGGTGGAAGCAAAGGATAAGACGGCGGAGAAGAT
TGGTGAGTACAAAGACTATGCGGTGGATAAGGCAGTAGAAGCTAAAGATAAGAC
AGCGGAGAAGGCGAAGGAGACTTCGAATTATACGGCGGATAAGGCTAAAGAGG
CTAAGGACAAGACGGCTGAGAAGGTTGGTGAGTATAAGGATTACACGGTGGACA
AGGCCGTGGAAGCTAGGGATTACACAGCGGAGAAGGCTATTGAAGCAAAGGAT
AAGACAGCTGAGAAGACTGGAGAGTATAAGGACTATACGGTGGAGAAGGCGAC
GGAGGGGAAAGATGTTACGGTGAGTAAGCTAGGAGAGCTGAAGGATAGTGCCGT
TGAGACAGCGAAGAGAGCTATGGGTTTCTTGTCGGGGAAGACAGAGGAGGCCAA
AGGAAAAGCTGTGGAGACCAAAGATACTGCCAAGGAAAACATGGAGAAAGCTG
GAGAAGTAACAAGACAAAAGATGGAGGAAATGAGATTGGAAGGTAAAGAGCTC
AAAGAAGAAGCTGGAGCAAAAGCCCAAGAGGCATCTCAAAAGACTAGGGAGAG
TACTGAGTCGGGAGCTCAAAAAGCCGAAGAGACCAAAGATTCTCCTGCCGTGAG
GGGAAATGAAGCGAAAGGGACTATTTTTGGTGCATTAGGGAATGTAACGGAAGC
AATAAAGAGCAAACTGACAATGCCATCAGACATTGTGGAGGAAACACGCGCGGC
ACGTGAGCATGGAGGGACGGGTAGGACTGTGGTTGAAGTCAAGGTCGAGGATTC
AAAGCCGGGTAAGGTGGCGACTTCACTGAAGGCGTCGGATCAAATGACCGGTCA

Figure 10A Continued

AACATTCAACGACGTTGGACGGATGGATGATGATGCTCGGAAAGATAAGGGAAAGCTGTGA

Figure 10B

SEQ ID NO:20, Amino acid sequence of the open reading frame of pk064

MASDKQKAERAEVAARLAAEDLHDINKSGGADVTMYKVTERTTEHPPEQDRPGVIGSVFRAVQGTYEHARDAVVGKTHEAAESTKEGAQIASEKAVGAKDATVEKAKETADYTAEKVGEYKDYTVDKAKEAKDTTAEKAKETANYTADKAVEAKDKTAEKIGEYKDYAVDKAVEAKDKTAEKAKETSNYTADKAKEAKDKTAEKVGEYKDYTVDKAVEARDYTAEKAIEAKDKTAEKTGEYKDYTVEKATEGKDVTVSKLGELKDSAVETAKRAMGFLSGKTEEAKGKAVETKDTAKENMEKAGEVTRQKMEEMRLEGKELKEEAGAKAQEASQKTRESTESGAQKAEETKDSPAVRGNEAKGTIFGALGNVTEAIKSKLTMPSDIVEETRAAREHGGTGRTVVEVKVEDSKPGKVATSLKASDQMTGQTFNDVGRMDDDARKDKGKL

Figure 11A

SEQ ID NO:21, Nucleotide sequence of the open reading frame of pk073

ATGCTCTCTGACGCCGGGGGTGGTTCCGATTGCCGGCGTCGGGACTTATCAACTCCCATCAACCTTCATGTGTTCTATATAAGCTTTATCTTCATTGAATCTTCCTCCGTTATCTCAAATCTCTCAAAATATCTAAATCTCCTTTTTTATGTGAGCTTCTTCACTGAAAGTTTTCTTTGTGACGGAAGAGTATATCGATGCTCTATTGGCTCCGATCTGACTCAGATCTTGGATGCATCTCTGTCTTCGAACCCAAAACAAGAAAATTCACAACAGTCCAACAGCTCCTCTTCTCAAACATCAGAGCAAGACTTCATCAACTTATCAAAAGCTCTAGATCTGGACTAGCACCAACACCACCTTTGGTTTCTTCTCACCGGTTTTCGTTGATGGCAGGAGTATCTCTTGGACCATCAGATGTGCTTCTTCCGCTGGGAACGTCGACGGCACACGACGAGCTCAAACGCTGGCAATGGTCACCCTATATGATTCACAGTCGCCCATCATTCCAATTCTTCAGAATGACGGAGGCGCTTTCCTTATCCCGACAACATCAACCCTAG

Figure 11B

SEQ ID NO:22, Amino acid sequence of the open reading frame of pk073

MLSDAGGGSDCRRRDLSTPINLHVFYISFIFIESSSVISNLSKYLNLLFYVSFFTESFLCD
GRVYRCSIGSDLTQILDASLSSNPKQENSQQSNSSSSQTSEQDFINLSKSSRSGLAPTPP
LVSSHRFSLMAGVSLGPSDVLLPLGTSTAHDELKRWQWSPYMIHSRPSFQFFRMTEA
LSLSRQHQP

Figure 12A

SEQ ID NO:23, Nucleotide sequence of the open reading frame of pk082

ATGGAAGGTGGAGCTGCTCTCTACAATCCTCGAACTGTCGAAGAAGTTTTCAAGG
ATTTCAAAGGTCGTCGTACTGCCATTGTCAAAGCTCTCACCACCGATGTTCAAGA
GTTTTACCAACAATGTGACCCTGAGAAGGAGAATCTTTGCTTGTATGGGTTACCG
AATGAAGAATGGGAAGTGAATTTACCAGCTGAAGAAGTGCCTCCTGAGTTACCA
GAGCCAGCTCTTGGTATTAACTTTGCTAGGGATGGGCTCTCTGAAAAGGAATGGC
TTTCGCTTGTTGCTATTCACAGTGACGCTTGGTTACTGTCTGTCTCGTTTTACTTTG
GCTCAAGGTTTTCTTTCCACAAGGAAGAGAGGAAGCGTTTGTTCAACATGATCAA
TGATGTTCCTACTATATTTGAAGTAGTGACTGGAATGGCTAAAGCAAAGGACAA
GTCATCTGCTGCAAATCAAAACGGAAACAAATCCAAGTCTAACTCTAAAGTTAG
AACTTCAGGGGGAAAAAGCTCAAAGACCAAGCAGCCAAAAGAGGAGGACGAAG
AAATAGATGAAGATGATGAGGATGACCACGGGGAAACCCTTTGTGGAGCCTGTG
GAGACAGTGATGGTGCTGATGAATTCTGGATCTGCTGTGACCTTTGTGAGAAGTG
GTTCCATGGCAAGTGTGTGAAGATCACTCCAGCTAGAGCTGAGCATATCAAACA
ATACAAGTGCCCTTCATGCAGCAACAAAAGAGCTCGAGCTTAA

Figure 12B

SEQ ID NO:24, Amino acid sequence of the open reading frame of pk082

MEGGAALYNPRTVEEVFKDFKGRRTAIVKALTTDVQEFYQQCDPEKENLCLYGLPN
EEWEVNLPAEEVPPELPEPALGINFARDGLSEKEWLSLVAIHSDAWLLSVSFYFGSRF
SFHKEERKRLFNMINDVPTIFEVVTGMAKAKDKSSAANQNGNKSKSNSKVRTSGGK
SSKTKQPKEEDEEIDEDDEDDHGETLCGACGDSDGADEFWICCDLCEKWFHGKCVK
ITPARAEHIKQYKCPSCSNKRARA

Figure 13A

SEQ ID NO:25, Nucleotide sequence of the open reading frame of pk084a

ATGGGGTCATCACAGTCTTCGCAATTACTCGATGAAGAAGAAGAAGAAGAT
GAAGCAGAGAGCGAAGGTGAAGAAGTAGAAGAAGAAGAAGATGAAGCAGAGA
GCGAATTGAATAACAGAAGAATCGAGCTGGATAATCTCTTGGTCAAGAAAGTTC
TCGAGCAAGAGCCTGAGATGCTTCCTTGTCACGCCTCTGCTTCTCCACTCTCTCCT
CAGCTCTCTTCTCTTGGAACTCCTCGAATCGGACCTTCCATTAAAGTCTGGGATCC
TTACAACGTCCTCGCGCCACCTCCTCCTTCTTCTCCGCCTCTTTTCTCTCGTATCTC
CTCCGCCGCGGAACACGATCGCTCCGCCGTGACGGAAGTCTATTTCATCAGCCAC
GGCGAGTGTGATCTCAATCTCAGGCCTGATCTGATTGGAGGTAGATGCCACGTGG
CTACTCTCACACCCAACGGGAAACGTCAGGCGAGAGCTCTAGCCGTATTTTTAAA
CTCTGAAGGTGTTCGATTCACCTCCGTCTTCTCTTCGCCTCTGGATCGAGCTAGAT
CCATGGCTGTTTCTGTTTGCCAGGAAATGAATTTTCCTGAGGAGCATTTGCAAGT
CTCGGATGCTGTGGTTGAGATGAGTTTAGGGGACTGGGAAAGCTGTCATCGGTCA
GAGATTTACACACCTGAAACTCTAAGTTTAATAGAAAGATGCCAACCTGATTTCT
CAGCTCCATCTGGTGAATCACTCAGACAAGTAGAGTTTCGGATGGTTCAGTTTCT
GAATGGGACAGTCTCAGGACTTTCGGAGAAGCTCAGGTCAGAACTTCTTCCATCT
ACACAGCACACAAATTCCAGAGGGTTCTCGTTAGCTACTTCTATTCATCGCCCAA
TTCTTACAAGGAAGAAATCTGGGAAGAGCCGGTTTCAGGTGATGAATGCAACTG
GTGATCACGAGGGTAGTGAAGAGATATTTAGTAATCACAATGATGAACAACACC
TAGGTGATATAAACATCAAGAGTTCTTCTTCTCAACTCTCAACCTGCATTGGAGT
TTTCACTCACTCTTTACCTATAAAGTGTCTTCTTACCGGTATCCTTGGATGCAGCC
CGGTAATGACACATAAGATCTGTGTGGAGGATTCCTCTGTGACCGTATTACAGCA
TTCGTGGAAAACCGGGTGGCAGGTAAAGCGGTTAAATGACACCGCTCATCTTAG
ACTGTTGTAG

Figure 13B

SEQ ID NO:26, Amino acid sequence of the open reading frame of pk084a

MGSSQSSQLLDEEEEEEDEAESEGEEVEEEEDEAESELNNRRIELDNLLVKKVLEQEP
EMLPCHASASPLSPQLSSLGTPRIGPSIKVWDPYNVLAPPPPSSPPLFSRISSAAEHDRS
AVTEVYFISHGECDLNLRPDLIGGRCHVATLTPNGKRQARALAVFLNSEGVRFTSVFS
SPLDRARSMAVSVCQEMNFPEEHLQVSDAVVEMSLGDWESCHRSEIYTPETLSLIER
CQPDFSAPSGESLRQVEFRMVQFLNGTVSGLSEKLRSELLPSTQHTNSRGFSLATSIHR

Figure 13B Continued

PILTRKKSGKSRFQVMNATGDHEGSEEIFSNHNDEQHLGDINIKSSSSQLSTCIGVFTH
SLPIKCLLTGILGCSPVMTHKICVEDSSVTVLQHSWKTGWQVKRLNDTAHLRLL

Figure 14A

SEQ ID NO:27, Nucleotide sequence of the open reading frame of pk086

ATGCTAGATCACAGTGAAAAGGTCTTATTGGTTGATTCAGAAACCATGAAAACA
AGAGCTGAAGATATGATCGAACAGAACAACACTAGTGTTAACGACAAGAAGAA
GACTTGTGCTGATTGTGGAACCAGTAAAACTCCTCTTTGGCGTGGTGGTCCTGTT
GGTCCAAAGTCGTTGTGTAACGCGTGTGGGATCAGAAACAGAAAGAAGAGAAGA
GGAGGAACAGAAGATAATAAGAAATTAAAGAAATCGAGTTCTGGCGGCGGAAA
CCGTAAATTTGGTGAATCGTTAAAACAGAGTTTGATGGATTTGGGGATAAGGAA
GAGATCAACGGTGGAGAAGCAACGACAGAAGCTTGGTGAAGAAGAACAAGCCG
CTGTGTTACTCATGGCTCTTTCTTATGGCTCTGTTTACGCTTAG

Figure 14B

SEQ ID NO:28, Amino acid sequence of the open reading frame of pk086

MLDHSEKVLLVDSETMKTRAEDMIEQNNTSVNDKKKTCADCGTSKTPLWRGGPVG
PKSLCNACGIRNRKKRRGGTEDNKKLKKSSSGGGNRKFGESLKQSLMDLGIRKRSTV
EKQRQKLGEEEQAAVLLMALSYGSVYA

Figure 15A

SEQ ID NO:29, Nucleotide sequence of the open reading frame of pk088b

ATGGCAACACACTCTTCCTTCACCGCAACAACACCTCTCTTTCTCATCGTTCTTCT
ATCCCTATCCTCCGTCTCAGTTCTCGGCGCATCTCACCACCACGCAACGGCGCCG
GCTCCGTCTGTAGACTGTTCGACTCTCATACTCAACATGGCTGACTGTTTATCCTT
CGTTTCGAGCGGAGGCACGGTGGCGAAACCGGAAGGTACATGTTGCTCTGGTCTT
AAGACGGTGCTTAAAGCTGACTCTCAGTGTCTATGTGAAGCGTTTAAGAGCAGTG
CTTCTCTTGGAGTTACTTTGAATATCACTAAGGCTTCTACTCTTCCCGCCGCATGC
AAGCTTCACGCTCCTTCTATCGCTACTTGTGGATGTCTTGCTCCAGGAGTAGCTGC
TGCTGGACCTGAGACAGCCGGATTTCTAGCTCCAAATCCTTCTTCAGGGAACGAT

Figure 15A Continued

GGATCTTCTTTGATTCCGACCTCGTTCACAACTGTACTCAGTGCCGTACTGTTCGT
TTTGTTCTTCTCTAGTGCGTAA

Figure 15B

SEQ ID NO:30, Amino acid sequence of the open reading frame of pk088b

MATHSSFTATTPLFLIVLLSLSSVSVLGASHHHATAPAPSVDCSTLILNMADCLSFVSS
GGTVAKPEGTCCSGLKTVLKADSQCLCEAFKSSASLGVTLNITKASTLPAACKLHAP
SIATCGLSVAPSTAPGLAPGVAAAGPETAGFLAPNPSSGNDGSSLIPTSFTTVLSAVLF
VLFFSSA

Figure 16A

SEQ ID NO:31, Nucleotide sequence of the open reading frame of pk095

ATGGACCCTTTAGCTTCCCAACATCAACACAACCATCTGGAAGATAATAACCAAA
CCCTAACCCATAATAATCCTCAATCCGATTCCACCACCGACTCATCAACTTCCTCC
GCTCAACGCAAACGCAAAGGCAAAGGTGGTCCGGACAACTCCAAGTTCCGTTAC
CGTGGCGTTCGACAAAGAAGCTGGGGCAAATGGGTCGCCGAGATCCGAGAGCCA
CGTAAGCGCACTCGCAAGTGGCTTGGTACTTTCGCAACCGCCGAAGACGCCGCA
CGTGCCTACGACCGGGCTGCCGTTTACCTATACGGGTCACGTGCTCAGCTCAACT
TAACCCCTTCGTCTCCTTCCTCCGTCTCTTCCTCTTCCTCCTCCGTCTCCGCCGCTT
CTTCTCCTTCCACCTCCTCTTCCTCCACTCAAACCCTAAGACCTCTCCTCCCTCGC
CCCGCCGCCGCCACCGTAGGAGGAGGAGCCAACTTTGGTCCGTACGGTATCCCTT
TTAACAACAACATCTTCCTTAATGGTGGGACCTCTATGTTATGCCCTAGTTATGGT
TTTTTCCCTCAACAACAACAACAACAAAATCAGATGGTCCAGATGGGACAATTCC
AACACCAACAGTATCAGAATCTTCATTCTAATACTAACAATAACAAGATTTCTGA
CATCGAGCTCACTGATGTTCCGGTAACTAATTCGACTTCGTTTCATCATGAGGTG
GCGTTAGGGCAGGAACAAGGAGGAAGTGGGTGTAATAATAATAGTTCGATGGAG
GATTTGAACTCTCTAGCTGGTTCGGTGGGTTCGAGTCTATCAATAACTCATCCAC
CGCCGTTGGTTGATCCGGTATGTTCTATGGGTCTGGATCCGGGTTATATGGTTGG
AGATGGATCTTCGACCATTTGGCCTTTTGGAGGAGAAGAAGAATATAGTCATAAT
TGGGGGAGTATTTGGGATTTTATTGATCCCATCTTGGGGGAATTCTATTAA

Figure 16B

SEQ ID NO:32, Amino acid sequence of the open reading frame of pk095

MDPLASQHQHNHLEDNNQTLTHNNPQSDSTTDSSTSSAQRKRKGKGGPDNSKFRYR
GVRQRSWGKWVAEIREPRKRTRKWLGTFATAEDAARAYDRAAVYLYGSRAQLNLT
PSSPSSVSSSSSSVSAASSPSTSSSSTQTLRPLLPRPAAATVGGGANFGPYGIPFNNNIFL
NGGTSMLCPSYGFFPQQQQQQNQMVQMGQFQHQQYQNLHSNTNNNKISDIELTDV
PVTNSTSFHHEVALGQEQGGSGCNNNSSMEDLNSLAGSVGSSLSITHPPPLVDPVCS
MGLDPGYMVGDGSSTIWPFGGEEEYSHNWGSIWDFIDPILGEFY

Figure 17A

SEQ ID NO:33, Nucleotide sequence of the open reading frame of pk096

ATGGTTAAAGAAATAGCTTCTTGGTTATTGATACTATCAATGGTGGTGTTTGTTTC
TCCGGTTTTAGCTATAAACGGCGGTGGTTATCCACGATGTAACTGCGAAGACGAA
GGAAACAGTTCTGGAGTACAGAGAACATTCTAGAAACTCAAAGAGTAAGCGAT
TTCTTAATCGCAGTAGCTTATTTCTCAATCCCTATTGAGTTACTTTACTTCGTGAG
TTGTTCCAATGTTCCATTCAAATGGGTTCTCTTTGAGTTTATCGCCTTCATTGTTCT
TTGTGGTATGACTCATCTTCTTCATGGTTGGACTTACTCTGCTCATCCATTTAGAT
TAATGATGGCGTTTACTGTTTTCAAGATGTTGACTGCTTTAGTCTCTTGTGCTACT
GCGATTACGCTTATTACTTTGATTCCTCTGCTTTTGAAAGTTAAAGTTAGAGAGTT
TATGCTTAAGAAGAAAGCTCATGAGCTTGGTCGTGAAGTTGGTTTGATTTTGATT
AAGAAAGAGACTGGCTTTCATGTTCGTATGCTTACTCAAGAGATTCGTAAGTCTT
TGGATCGTCATACGATTCTTTATACTACTTTGGTTGAGCTTTCGAAGACTTTAGGG
TTGCAGAATTTTGCGGTTTGGATGCCGAATGACGGTGGAACGGAGATGGATTTGA
CTCATGAGTTGAGAGGGAGAGGTGGTTATGGTGGTTGTTCTGTTTCTATGGAGGA
TTTGGATGTTGTTAGGATTAGGGAGAGTGATGAAGTGAATGTGTTGAGTGTTGAC
TCGTCCATTGCTCGAGCTAGTGGTGGTGGTGGGGATGTTAGTGAGATTGGTGCCG
TGGCTGCTATTAGAATGCCGATGCTTCGTGTTTCGGATTTTAATGGAGAGCTAAG
TTATGCGATACTTGTTTGTGTTTTACCGGGCGGGACGCCTCGGGATTGGACTTATC
AGGAGATTGAGATTGTTAAAGTTGTGGCGGATCAAGTAACCGTTGCGTTAGATCA
TGCAGCGGTTCTTGAAGAGTCTCAGCTTATGAGGGAGAAGCTGGCGGAACAGAA
CAGGGCGTTGCAGATGGCGAAGAGAGACGCGTTGAGAGCGAGCCAAGCGAGGA
ATGCGTTTCAGAAAACGATGAGCGAAGGGATGAGGCGTCCTATGCATTCGATAC
TCGGTCTTTTGTCGATGATTCAGGACGAGAAGTTGAGTGACGAGCAGAAAATGA

Figure 17A Continued

TTGTTGATACGATGGTTAAAACAGGGAATGTTATGTCGAATTTGGTGGGGGACTC
TATGGATGTGCCTGACGGTAGATTTGGTACGGAGATGAAACCATTTAGTCTGCAT
CGTACGATCCATGAAGCAGCTTGTATGGCGAGATGTTTGTGTCTATGCAATGGAA
TTAGGTTCTTGGTTGACGCGGAGAAGTCTCTACCTGATAATGTAGTAGGTGATGA
AGAAGGGTCTTTCAAGTGATACTTCATATAGTTGGTAGTTTAGTAAAGCCTAGA
AAACGTCAAGAAGGATCTTCATTGATGTTTAAGGTTTTGAAAGAAAGAGGAAGC
TTGGATAGGAGTGATCATAGATGGGCTGCTTGGAGATCACCGGCTTCTTCAGCAG
ATGGAGATGTGTATATAAGATTTGAAATGAATGTAGAGAATGATGATTCAAGTTC
TCAATCATTTGCTTCTGTTTCCTCCAGAGATCAAGAAGTTGGTGATGTTAGATTCT
CCGGCGGCTATGGGTTAGGACAAGATCTAAGCTTTGGTGTTTGTAAGAAAGTGGT
GCAGTTGATTCATGGGAATATCTCGGTGGTCCCTGGCTCGGATGGTTCACCGGAG
ACCATGTCGTTGCTCCCTCGGTTTCGACGTAGACCCTCCATATCTGTCCATGGATC
CAGCGAGTCGCCAGCTCCTGACCACCACGCTCACCCACATTCGAATTCTCTGTTA
CGTGGCTTACAAGTTTTATTGGTAGACACCAACGATTCGAACCGGGCAGTTACAC
GTAAACTCTTAGAGAAACTCGGGTGCGATGTAACCGCGGTTTCCTCTGGATTCGA
TTGCCTTACCGCCATTGCTCCCGGCTCGTCCTCGCCTTCTACTTCGTTTCAAGTGG
TGGTGCTTGATCTTCAAATGGCAGAGATGGACGGTTATGAAGTGGCCATGAGGA
TCAGGAGTCGATCTTGGCCGTTGATTGTGGCGACGACAGTGGGCTTGGATGAAG
AAATGTGGGACAAGTGTGCACAGATTGGAATCAATGGAGTTGTGAGAAAGCCAG
TGGTGTTAAGAGCTATGGAGAGTGAGCTCCGAAGAGTATTGTTGCAAGCTGACC
AACTTCTCTAA

Figure 17B

SEQ ID NO:34, Amino acid sequence of the open reading frame of pk096

MVKEIASWLLILSMVVFVSPVLAINGGGYPRCNCEDEGNSFWSTENILETQRVSDFLI
AVAYFSIPIELLYFVSCSNVPFKWVLFEFIAFIVLCGMTHLLHGWTYSAHPFRLMMAF
TVFKMLTALVSCATAITLITLIPLLLKVKVREFMLKKKAHELGREVGLILIKKETGFH
VRMLTQEIRKSLDRHTILYTTLVELSKTLGLQNFAVWMPNDGGTEMDLTHELRGRG
GYGGCSVSMEDLDVVRIRESDEVNVLSVDSSIARASGGGGDVSEIGAVAAIRMPMLR
VSDFNGELSYAILVCVLPGGTPRDWTYQEIEIVKVVADQVTVALDHAAVLEESQLM
REKLAEQNRALQMAKRDALRASQARNAFQKTMSEGMRRPMHSILGLLSMIQDEKLS
DEQKMIVDTMVKTGNVMSNLVGDSMDVPDGRFGTEMKPFSLHRTIHEAACMARCL
CLCNGIRFLVDAEKSLPDNVVGDERRVFQVILHIVGSLVKPRKRQEGSSLMFKVLKE

Figure 17B Continued

RGSLDRSDHRWAAWRSPASSADGDVYIRFEMNVENDDSSSQSFASVSSRDQEVGDV
RFSGGYGLGQDLSFGVCKKVVQLIHGNISVVPGSDGSPETMSLLPRFRRRPSISVHGS
SESPAPDHHAHPHSNSLLRGLQVLLVDTNDSNRAVTRKLLEKLGCDVTAVSSGFDCL
TAIAPGSSSPSTSFQVVVLDLQMAEMDGYEVAMRIRSRSWPLIVATTVGLDEEMWD
KCAQIGINGVVRKPVVLRAMESELRRVLLQADQLL

Figure 18A

SEQ ID NO:35, Nucleotide sequence of the open reading frame of pk097a

ATGGAAGTCTGCAATTGTATTGAACCGCAATGGCCAGCGGATGAATTGTTAATGA
AATACCAATACATCTCCGATTTCTTCATTGCGATTGCGTATTTTTCGATTCCTCTT
GAGTTGATTTACTTTGTGAAGAAATCAGCCGTGTTTCCGTATAGATGGGTACTTG
TTCAGTTTGGTGCTTTTATCGTTCTTTGTGGAGCAACTCATCTTATTAACTTATGG
ACTTTCACTACGCATTCGAGAACCGTGGCGCTTGTGATGACTACCGCGAAGGTGT
TAACCGCTGTTGTCTCGTGTGCTACTGCGTTGATGCTTGTTCATATTATTCCTGAT
CTTTTGAGTGTTAAGACTCGGGAGCTTTTCTTGAAAAATAAAGCTGCTGAGCTCG
ATAGAGAAATGGGATTGATTCGAACTCAGGAAGAAACCGGAAGGCATGTGAGA
ATGTTGACTCATGAGATTAGAAGCACTTTAGATAGACATACTATTTTAAAGACTA
CACTTGTTGAGCTTGGTAGGACATTAGCTTTGGAGGAGTGTGCATTGTGGATGCC
TACTAGAACTGGGTTAGAGCTACAGCTTTCTTATACACTTCGTCATCAACATCCC
GTGGAGTATACGGTTCCTATTCAATTACCGGTGATTAACCAAGTGTTTGGTACTA
GTAGGGCTGTAAAAATATCTCCTAATTCTCCTGTGGCTAGGTTGAGACCTGTTTCT
GGGAAATATATGCTAGGGGAGGTGGTCGCTGTGAGGGTTCCGCTTCTCCACCTTT
CTAATTTTCAGATTAATGACTGGCCTGAGCTTTCAACAAAGAGATATGCTTTGAT
GGTTTTGATGCTTCCTTCAGATAGTGCAAGGCAATGGCATGTCCATGAGTTGGAA
CTCGTTGAAGTCGTCGCTGATCAGGTGGCTGTAGCTCTCTCACATGCTGCGATCC
TAGAAGAGTCGATGCGAGCTAGGGACCTTCTCATGGAGCAGAATGTTGCTCTTGA
TCTAGCTAGACGAGAAGCAGAAACAGCAATCCGTGCCCGCAATGATTTCCTAGC
GGTTATGAACCATGAAATGCAACACCGATGCATGCGATTATTGCACTCTCTTCC
TTACTCCAAGAAACGGAACTAACCCCTGAACAAAGACTGATGGTGGAAACAATA
CTTAAAAGTAGTAACCTTTTGGCAACTTTGATGAATGATGTCTTAGATCTTTCAA
GGTTAGAAGATGGAAGTCTTCAACTTGAACTTGGGACATTCAATCTTCATACATT
ATTTAGAGAGGTCCTCAATCTGATAAAGCCTATAGCGGTTGTTAAGAAATTACCC

Figure 18A Continued

ATCACACTAAATCTTGCACCAGATTTGCCAGAATTTGTTGTTGGGGATGAGAAAC
GGCTAATGCAGATAATATTAAATATAGTTGGTAATGCTGTGAAATTCTCCAAACA
AGGTAGTATCTCCGTAACCGCTCTTGTCACCAAGTCAGACACGAGCTGCTGAC
TTTTTTGTCGTGCCAACTGGGAGTCATTTCTACTTGAGAGTGAAGGTAAAAGACT
CTGGAGCAGGAATAAATCCTCAAGACATTCCAAAGATTTTCACTAAATTTGCTCA
AACACAATCTTTAGCGACGAGAAGCTCGGGTGGTAGTGGGCTTGGCCTCGCCATC
TCCAAGAGGTTTGTGAATCTGATGGAGGGTAACATTTGGATTGAGAGCGATGGTC
TTGGAAAAGGATGCACGGCTATCTTTGATGTTAAACTTGGGATCTCAGAACGTTC
AAACGAATCTAAACAGTCGGGCATACCGAAAGTTCCAGCCATTCCCCGACATTC
AAATTTCACTGGACTTAAGGTTCTTGTCATGGATGAGAACGGGGTAAGTAGAATG
GTGACGAAGGGACTTCTTGTACACCTTGGGTGCGAAGTGACCACGGTGAGTTCA
AACGAGGAGTGTCTCCGAGTTGTGTCCATGAGCACAAAGTGGTCTTCATGGACG
TGTGCATGCCCGGGGTCGAAAACTACCAAATCGCTCTCCGTATTCACGAGAAATT
CACAAAACAACGCCACCAACGGCCACTACTTGTGGCACTCAGTGGTAACACTGA
CAAATCCACAAAAGAGAAATGCATGAGCTTTGGTCTAGACGGTGTGTTGCTCAA
ACCCGTATCACTAGACAACATAAGAGATGTTCTGTCTGATCTTCTCGAGCCCCGG
GTACTGTACGAGGGCATGTAA

Figure 18B

SEQ ID NO:36, Amino acid sequence of the open reading frame of pk097a

MEVCNCIEPQWPADELLMKYQYISDFFIAIAYFSIPLELIYFVKKSAVFPYRWVLVQF
GAFIVLCGATHLINLWTFTTHSRTVALVMTTAKVLTAVVSCATALMLVHIIPDLLSV
KTRELFLKNKAAELDREMGLIRTQEETGRHVRMLTHEIRSTLDRHTILKTTLVELGRT
LALEECALWMPTRTGLELQLSYTLRHQHPVEYTVPIQLPVINQVFGTSRAVKISPNSP
VARLRPVSGKYMLGEVVAVRVPLLHLSNFQINDWPELSTKRYALMVLMLPSDSARQ
WHVHELELVEVVADQVAVALSHAAILEESMRARDLLMEQNVALDLARREAETAIR
ARNDFLAVMNHEMRTPMHAIIALSSLLQETELTPEQRLMVETILKSSNLLATLMNDV
LDLSRLEDGSLQLELGTFNLHTLFREVLNLIKPIAVVKKLPITLNLAPDLPEFVVGDEK
RLMQIILNIVGNAVKFSKQGSISVTALVTKSDTRAADFFVVPTGSHFYLRVKVKDSGA
GINPQDIPKIFTKFAQTQSLATRSSGGSGLGLAISKRFVNLMEGNIWIESDGLGKGCTA
IFDVKLGISERSNESKQSGIPKVPAIPRHSNFTGLKVLVMDENGVSRMVTKGLLVHLG
CEVTTVSSNEECLRVVSHEHKVVFMDVCMPGVENYQIALRIHEKFTKQRHQRPLLV
ALSGNTDKSTKEKCMSFGLDGVLLKPVSLDNIRDVLSDLLEPRVLYEGM

Figure 18C

SEQ ID NO:37, Nucleotide sequence of the open reading frame of pk097b

ATGGAAGTCTGCAATTGTATTGAACCGCAATGGCCAGCGGATGAATTGTTAATGA
AATACCAATACATCTCCGATTTCTTCATTGCGATTGCGTATTTTCGATTCCTCTT
GAGTTGATTTACTTTGTGAAGAAATCAGCCGTGTTTCCGTATAGATGGGTACTTG
TTCAGTTTGGTGCTTTTATCGTTCTTTGTGGAGCAACTCATCTTATTAACTTATGG
ACTTTCACTACGCATTCGAGAACCGTGGCGCTTGTGATGACTACCGCGAAGGTGT
TAACCGCTGTTGTCTCGTGTGCTACTGCGTTGATGCTTGTTCATATTATTCCTGAT
CTTTTGAGTGTTAAGACTCGGGAGCTTTTCTTGAAAAATAAAGCTGCTGAGCTCG
ATAGAGAAATGGGATTGATTCGAACTCAGGAAGAAACCGGAAGGCATGTGAGA
ATGTTGACTCATGAGATTAGAAGCACTTTAGATAGACATACTATTTTAAAGACTA
CACTTGTTGAGCTTGGTAGGACATTAGCTTTGGAGGAGTGTGCATTGTGGATGCC
TACTAGAACTGGGTTAGAGCTACAGCTTTCTTATACACTTCGTCATCAACATCCC
GTGGAGTATACGGTTCCTATTCAATTACCGGTGATTAACCAAGTGTTTGGTACTA
GTAGGGCTGTAAAAATATCTCCTAATTCTCCTGTGGCTAGGTTGAGACCTGTTTCT
GGGAAATATATGCTAGGGGAGGTGGTCGCTGTGAGGGTTCCGCTTCTCCACCTTT
CTAATTTTCAGATTAATGACTGGCCTGAGCTTTCAACAAAGAGATATGCTTTGAT
GGTTTTGATGCTTCCTTCAGATAGTGCAAGGCAATGGCATGTCGATGAGTTGGAA
CTCGTTGAAGTCGTCGCTGATCAGGTGGCTGTAGCTCTCTCACATGCTGCGATCC
TAGAAGAGTCGATGCGAGCTAGGGACCTTCTCATGGAGCAGAATGTTGCTCTTGA
TCTAGCTAGACGAGAAGCAGAAACAGCAATCCGTGCCCGCAATGATTTCCTAGC
GGTTATGAACCATGAAATGCGAACACCGATGCATGCGATTATTGCACTCTCTTCC
TTACTCCAAGAAACGGAACTAACCCCTGAACAAAGACTGATGGTGGAAACAATA
CTTAAAAGTAGTAACCTTTTGGCAACTTTGATGAATGATGTCTTAGATCTTTCAA
GGTTAGAAGATGGAAGTCTTCAACTTGAACTTGGGACATTCAATCTTCATACATT
ATTTAGAGAGGTCCTCAATCTGATAAAGCCTATAGCGGTTGTTAAGAAATTACCC
ATCACACTAAATCTTGCACCAGATTTGCCAGAATTTGTTGTTGGGGATGAGAAAC
GGCTAATGCAGATAATATTAAATATAGTTGGTAATGCTGTGAAATTCTCCAAACA
AGGTAGTATCTCCGTAACCGCTCTTGTCACCAAGTCAGACACACGAGCTGCTGAC
TTTTTTGTCGTGCCAACTGGGAGTCATTTCTACTTGAGAGTGAAGGTAAAAGACT
CTGGAGCAGGAATAAATCCTCAAGACATTCCAAAGATTTTCACTAAATTTGCTCA
AACACAATCTTTAGCGACGAGAAGCTCGGGTGGTAGTGGGCTTGGCCTCGCCATC
TCCAAGAGGTTTGTGAATCTGATGGAGGGTAACATTTGGATTGAGAGCGATGGTC
TTGGAAAAGGATGCACGGCTATCTTTGATGTTAAACTTGGGATCTCAGAACGTTC

Figure 18C Continued

AAACGAATCTAAACAGTCGGGCATACCGAAAGTTCCAGCCATTCCCCGACATTC
AAATTTCACTGGACTTAAGGTTCTTGTCATGGATGAGAACGGGGTAAGTAGAATG
GTGACGAAGGGACTTCTTGTACACCTTGGGTGCGAAGTGACCACGGTGAGTTCA
AACGAGGAGTGTCTCCGAGTTGTGTCCCATGAGCACAAAGTGGTCTTCATGGACG
TGTGCATGCCCGGGGTCGAAAACTACCAAATCGCTCTCCGTATTCACGAGAAATT
CACAAAACAACGCCACCAACGGCCACTACTTGTGGCACTCAGTGGTAACACTGA
CAAATCCACAAAAGAGAAATGCATGAGCTTTGGTCTAGACGTGTGTTGCTCAAA
CCCGTATCACTAG

Figure 18D

SEQ ID NO:38, Amino acid sequence of the open reading frame of pk097b

MEVCNCIEPQWPADELLMKYQYISDFFIAIAYFSIPLELIYFVKKSAVFPYRWVLVQF
GAFIVLCGATHLINLWTFTTHSRTVALVMTTAKVLTAVVSCATALMLVHIIPDLLSV
KTRELFLKNKAAELDREMGLIRTQEETGRHVRMLTHEIRSTLDRHTILKTTLVELGRT
LALEECALWMPTRTGLELQLSYTLRHQHPVEYTVPIQLPVINQVFGTSRAVKISPNSP
VARLRPVSGKYMLGEVVAVRVPLLHLSNFQINDWPELSTKRYALMVLMLPSDSARQ
WHVDELELVEVVADQVAVALSHAAILEESMRARDLLMEQNVALDLARREAETAIR
ARNDFLAVMNHEMRTPMHAIIALSSLLQETELTPEQRLMVETILKSSNLLATLMNDV
LDLSRLEDGSLQLELGTFNLHTLFREVLNLIKPIAVVKKLPITLNLAPDLPEFVVGDEK
RLMQIILNIVGNAVKFSKQGSISVTALVTKSDTRAADFFVVPTGSHFYLRVKVKDSGA
GINPQDIPKIFTKFAQTQSLATRSSGGSGLGLAISKRFVNLMEGNIWIESDGLGKGCTA
IFDVKLGISERSNESKQSGIPKVPAIPRHSNFTGLKVLVMDENGVSRMVTKGLLVHLG
CEVTTVSSNEECLRVVSHEHKVVFMDVCMPGVENYQIALRIHEKFTKQRHQRPLLV
ALSGNTDKSTKEKCMSFGLDVCCSNPYH

Figure 19A

SEQ ID NO:39, Nucleotide sequence of the open reading frame of pk098

ATGATGGGCAGTGTCGAGCTGAATCTGAGGGAGACTGAGCTGTGTCTTGGTCTTC
CCGGTGGAGATACAGTGGCTCCGGTAACCGGAAACAAGAGAGGGTTCTCAGAGA
CGGTTGATCTGAAGCTAAATCTGAATAATGAGCCTGCAAACAAGGAAGGATCTA
CGACTCATGACGTCGTGACTTTTGATTCCAAGGAGAAGAGTGCTTGTCCTAAAGA
TCCAGCCAAACCTCCGGCCAAGGCACAAGTTGTGGGATGGCCACCGGTGAGATC

Figure 19A Continued

ATACCGGAAGAACGTGATGGTTTCCTGCCAAAAATCAAGCGGTGGCCCGGAGGC
GGCGGCGTTCGTGAAGGTATCAATGGACGGAGCACCGTACTTGAGGAAAATCGA
TTTGAGGATGTATAAAAGCTACGATGAGCTTTCTAATGCTTTGTCCAACATGTTC
AGCTCTTTTACCATGGGCAAACATGGAGGAGAAGAAGGAATGATAGACTTCATG
AATGAGAGGAAATTGATGGATTTGGTGAATAGCTGGGACTATGTTCCTCTTATG
AAGACAAAGACGGTGATTGGATGCTCGTCGGCGACGTTCCTTGGCCAATGTTCGT
CGATACATGCAAGCGTTTACGTCTCATGAAAGGATCGGATGCCATTGGTCTCGCT
CCGAGGGCGATGGAGAAGTGCAAGAGCAGAGCTTGA

Figure 19B

SEQ ID NO:40, Amino acid sequence of the open reading frame of pk098

MMGSVELNLRETELCLGLPGGDTVAPVTGNKRGFSETVDLKLNLNNEPANKEGSTT
HDVVTFDSKEKSACPKDPAKPPAKAQVVGWPPVRSYRKNVMVSCQKSSGGPEAAA
FVKVSMDGAPYLRKIDLRMYKSYDELSNALSNMFSSFTMGKHGGEEGMIDFMNER
KLMDLVNSWDYVPSYEDKDGDWMLVGDVPWPMFVDTCKRLRLMKGSDAIGLAPR
AMEKCKSRA

Figure 20A

SEQ ID NO:41, Nucleotide sequence of the open reading frame of pk099

ATGATCGGCCAACTTATGAACCTCAAGGCCACGGAGCTCTGTCTCGGCCTCCCCG
GCGGCGCTGAAGCAGTTGAGAGTCCTGCCAAATCGGCGGTGGGAAGCAAGAGAG
GCTTCTCCGAAACCGTTGATCTCATGCTCAATCTTCAATCTAACAAAGAAGGCTC
CGTTGATCTCAAAAACGTTTCTGCTGTTCCCAAGGAGAAGACTACCCTTAAAGAT
CCTTCTAAGCCTCCTGCTAAAGCACAAGTGGTGGGATGGCCACCTGTGAGGAACT
ACAGGAAGAACATGATGACTCAGCAGAAGACCAGTAGTGGTGCGGAGGAGGCC
AGCAGTGAGAAGGCCGGGAACTTTGGTGGAGGAGCAGCCGGAGCCGGCTTGGTG
AAGGTCTCCATGGACGGTGCTCCATATCTGAGGAAAGTTGACCTCAAGATGTACA
AAAGCTACCAGGATCTTTCTGATGCATTGGCCAAAATGTTCAGCTCCTTTACTAT
GGGAAACTATGGAGCACAAGGAATGATAGATTTCATGAACGAGAGCAAGCTAAT
GAATCTGCTGAATAGCTCTGAGTATGTGCCAAGCTACGAGGACAAAGATGGTGA
CTGGATGCTCGTTGGCGATGTCCCATGGGAAATGTTTGTCGAGTCTTGCAAACGT

Figure 20A Continued

TTGCGCATTATGAAGGGATCTGAAGCAGTTGGACTTGCTCCGAGAGCAATGGAG
AAGTACTGCAAGAACAGATCTTGA

Figure 20B

SEQ ID NO:42, Amino acid sequence of the open reading frame of pk099

MIGQLMNLKATELCLGLPGGAEAVESPAKSAVGSKRGFSETVDLMLNLQSNKEGSV
DLKNVSAVPKEKTTLKDPSKPPAKAQVVGWPPVRNYRKNMMTQQKTSSGAEEASS
EKAGNFGGGAAGAGLVKVSMDGAPYLRKVDLKMYKSYQDLSDALAKMFSSFTMG
NYGAQGMIDFMNESKLMNLLNSSEYVPSYEDKDGDWMLVGDVPWEMFVESCKRL
RIMKGSEAVGLAPRAMEKYCKNRS

Figure 21A

SEQ ID NO:43, Nucleotide sequence of the open reading frame of pk100

ATGAAAAGCTTGCATGTGGCGGCCAACGCCGGAGATCTGGCTGAGGATTGTGGA
ATACTCGGTGGAGACGCTGATGATACTGTTTTGATGGATGGAATTGATGAAGTTG
GTAGAGAGATCTGGTTAGATGACCATGGAGGAGATAATAATCATGTTCATGGTC
ATCAAGATGATGATTTGATTGTTCATCATGACCCTTCAATCTTCTATGGAGATCTC
CCAACGCTTCCTGATTTCCCATGCATGTCGTCTTCATCATCGTCTTCAACATCTCC
AGCTCCTGTCAACGCAATCGTCTCCTCAGCCTCTTCTTCTTCGGCAGCTTCTTCCT
CCACTTCCTCAGCTGCTTCTTGGGCTATATTGAGATCAGATGGAGAAGATCCGAC
TCCAAACCAAAACCAATACGCATCAGGAAACTGTGACGACTCTTCTGGTGCATTG
CAATCCACAGCTTCCATGGAGATTCCATTAGACAGCAGTCAAGGTTTTGGTTGCG
GCGAAGGCGGTGGTGATTGCATTGATATGATGGAGACTTTCGGGTACATGGATCT
ACTTGATAGCAACGAGTTCTTTGACACCTCAGCTATATTTAGCCAAGACGACGAC
ACGCAAAACCCTAACTTGATGGACCAAACCCTTGAGAGACAAGAAGACCAGGTC
GTTGTTCCGATGTTGGAGAATAACAGTGGTGGAGACATGCAAATGATGAATTCTT
CCTTGGAACAGGACGATGATCTCGCTGCTGTGTTTTGGAGTGGCTAAAGAACAA
CAAGGAGACTGTGTCGGCTGAGGATTTGAGGAAAGTAAAGATAAAGAAAGCTAC
GATTGAATCAGCGGCAAGAAGACTAGGCGGTGGTAAAGAAGCGATGAAGCAGC
TTTTAAAGCTGATTCTTGAATGGGTCCAAACTAATCACTTACAAAGAAGACGCAC
CACCACCACCACCACCAACCTCTCTTATCAACAATCATTCCAACAAGATCCATTT
CAAAACCCTAACCCTAATAACAACAACCTAATCCCACCGTCCGACCAAACCTGTT

Figure 21A Continued

TCTCACCTTCAACATGGGTTCCTCCACCACCACAACAACAAGCTTTTGTCTCGGA
CCCGGGTTTTGGATACATGCCTGCTCCAAACTATCCGCCACAGCCAGAGTTCCTT
CCTTTACTTGAATCTCCACCGTCATGGCCACCACCACCACAGTCTGGTCCCATGC
CACATCAACAATTCCCCATGCCGCCAACCTCGCAGTATAATCAATTTGGAGATCC
AACAGGTTTCAATGGATACAACATGAATCCGTACCAATATCCTTATGTTCCTGCA
GGACAAATGAGAGATCAGAGATTACTCCGTTTGTGTTCCTCAGCAACTAAAGAG
GCAAGAAAGAAACGGATGGCGAGACAGAGGAGGTTCTTGTCTCATCACCACAGA
CATAACAACAACAACAACAACAATAATCAGCAGAACCAAACCCAAATCGG
AGAAACCTGTGCCGCGGTGGCTCCACAACTTAACCCCGTGGCCACAACCGCCAC
GGGAGGGACCTGGATGTATTGGCCTAATGTCCCGGCAGTGCCGCCTCAATTACCG
CCAGTGATGGAGACTCAGTTACCCACCATGGACCGAGCTGGCTCAGCTTCTGCTA
TGCCACGTCAGCAGGTGGTACCAGATCGCCGGCAGGGATGGAAACCAGAAAGA
ATTTGCGGTTTCTCTTGCAGAAAGTCTTGAAGCAAAGCGACGTGGGTAACCTCGG
AAGGATCGTTTTGCCAAAAAAGAAGCTGAGACACACTTGCCGGAGCTAGAGGC
AAGAGACGGCATCTCTCTGGCCATGGAAGACATCGGAACCTCTCGTGTTTGGAAC
ATGCGCTACAGGTTTTGGCCTAACAACAAAAGCAGGATGTATCTCCTCGAGAAC
ACCGGCGATTTTGTGAAAACCAATGGGCTCCAAGAAGGTGATTTCATAGTCATAT
ACTCCGACGTCAAATTGATACGAGGGGTTAAAGTAAGACAACCGAGCGGACAAA
AGCCGGAGGCTCCACCGTCGTCAGCAGCTACGAAGAGACAAAACAAGTCGCAAA
GGAACATAAACAATAACTCTCCGTCGGCGAATGTGGTGGTCGCTTCACCAACTTC
TCAAACTGTTAAATGA

Figure 21B

SEQ ID NO:44, Amino acid sequence of the open reading frame of pk100

MKSLHVAANAGDLAEDCGILGGDADDTVLMDGIDEVGREIWLDDHGGDNNHVHG
HQDDDLIVHHDPSIFYGDLPTLPDFPCMSSSSSSSTSPAPVNAIVSSASSSSAASSSTSS
AASWAILRSDGEDPTPNQNQYASGNCDDSSGALQSTASMEIPLDSSQFGCGEGGGD
CIDMMETFGYMDLLDSNEFFDTSAIFSQDDDTQNPNLMDQTLERQEDQVVVPMLEN
NSGGDMQMMNSSLEQDDDLAAVFLEWLKNNKETVSAEDLRKVKIKKATIESAARR
LGGGKEAMKQLLKLILEWVQTNHLQRRRTTTTTNLSYQQSFQQDPFQNPNPNNNN
LIPPSDQTCFSPSTWVPPPPQQQAFVSDPGFGYMPAPNYPPQPEFLPLLESPPSWPPPP
QSGPMPHQQFPMPPTSQYNQFGDPTGFNGYNMNPYQYPYVPAGQMRDQRLLRLCS
SATKEARKKRMARQRRFLSHHHRHNNNNNNNNQQNQTQIGETCAAVAPQLNPVA

Figure 21B Continued

TTATGGTWMYWPNVPAVPPQLPPVMETQLPTMDRAGSASAMPRQQVVPDRRQGW
KPEKNLRFLLQKVLKQSDVGNLGRIVLPKKEAETHLPELEARDGISLAMEDIGTSRV
WNMRYRFWPNNKSRMYLLENTGDFVKTNGLQEGDFIVIYSDVKLIRGVKVRQPSGQ
KPEAPPSSAATKRQNKSQRNINNNSPSANVVASPTSQTVK

Figure 22A

SEQ ID NO:45, Nucleotide sequence of the open reading frame of pk105

ATGGAGGAAGTATCTCCGGCGATCGCAGGTCCTTTCAGGCCATTCTCCGAAACCC
AGATGGATTTCACCGGGATCAGATTGGGTAAAGGTTACTGCAATAACCAATACTC
AAATCAAGATTCCGAGAACGGAGATCTAATGGTTTCGTTACCGGAGACTTCATCA
TGCTCTGTTTCTGGGTCACATGGTTCTGAATCTAGGAAAGTTTTGATTTCTCGGAT
CAATTCTCCTAATTTAAACATGAAGGAATCAGCAGCTGCTGATATAGTCGTCGTT
GATATCTCCGCCGGAGATGAGATCAACGGCTCAGATGTTACTAGCGAGAAGAAG
ATGATCAGCAGAACAGAGAGTAGGAGTTTGTTTGAATTCAAGAGTGTGCCTTTGT
ATGGTTTCACTTCGATTTGTGGAAGAAGACCAGAGATGGAAGATGCTGTTTCGAC
TATACCAAGATTCCTTCAATCTTCTTCTGGTTCCATGTTAGATGGTCGGTTTGATC
CTCAATCCGCCGCTCATTTCTTCGGTGTTTACGACGGCCATGGCGGTTCTCAGGTA
GCGAACTATTGTAGAGAGAGGATGCATTTGGCTTTGGCGGAGGAGATAGCTAAG
GAGAAACCGATGCTCTGCGATGGTGATACGTGGCTGGAGAAGTGGAAGAAAGCT
CTTTTCAACTCGTTCCTGAGAGTTGACTCGGAGATTGAGTCAGTTGCGCCGGAGA
CGGTTGGGTCAACGTCGGTGGTTGCCGTTGTTTTCCCGTCTCACATCTTCGTCGCT
AACTGCGGTGACTCTAGAGCCGTTCTTTGCCGCGGCAAAACTGCACTTCCATTAT
CCGTTGACCATAAACCGGATAGAGAAGATGAAGCTGCGAGGATTGAAGCCGCAG
GAGGGAAAGTGATTCAGTGGAATGGAGCTCGTGTTTTCGGTGTTCTCGCCATGTC
GAGATCCATTGGCGATAGATACTTGAAACCATCCATCATTCCTGATCCGGAAGTG
ACGGCTGTGAAGAGAGTAAAAGAAGATGATTGTCTGATTTTGGCGAGTGACGGG
GTTTGGGATGTAATGACGGATGAAGAAGCGTGTGAGATGGCAAGGAAGCGGATT
CTCTTGTGGCACAAGAAAAACGCGGTGGCTGGGGATGCATCGTTGCTCGCGGAT
GAGCGGAGAAAGGAAGGGAAAGATCCTGCGGCGATGTCCGCGGCTGAGTATTTG
TCAAAGCTGGCGATACAGAGAGGAAGCAAAGACAACATAAGTGTGGTGGTGGTT
GATTTGAAGCCTCGGAGGAAACTCAAGAGCAAACCCTTGAACTGA

Figure 22B

SEQ ID NO:46, Amino acid sequence of the open reading frame of pk105

MEEVSPAIAGPFRPFSETQMDFTGIRLGKGYCNNQYSNQDSENGDLMVSLPETSSCS
VSGSHGSESRKVLISRINSPNLNMKESAAADIVVVDISAGDEINGSDVTSEKKMISRTE
SRSLFEFKSVPLYGFTSICGRRPEMEDAVSTIPRFLQSSSGSMLDGRFDPQSAAHFFGV
YDGHGGSQVANYCRERMHLALAEEIAKEKPMLCDGDTWLEKWKKALFNSFLRVDS
EIESVAPETVGSTSVVAVVFPSHIFVANCGDSRAVLCRGKTALPLSVDHKPDREDEAA
RIEAAGGKVIQWNGARVFGVLAMSRSIGDRYLKPSIIPDPEVTAVKRVKEDDCLILAS
DGVWDVMTDEEACEMARKRILLWHKKNAVAGDASLLADERRKEGKDPAAMSAAE
YLSKLAIQRGSKDNISVVVVDLKPRRKLKSKPLN

Figure 23A

SEQ ID NO:47, Nucleotide sequence of the open reading frame of pk107

ATGGAAATGCCCGGTAGAAGATCTAATTACACTTTGCTTAGTCAATTTTCTGACG
ATCAGGTGTCAGTTTCCGTCACCGGAGCTCCTCCGCCTCACTATGATTCCTTGTCG
AGCGAAAACAGGAGCAACCATAACAGCGGGAACACCGGGAAAGCTAAGGCGGA
GAGAGGCGGATTTGATTGGGATCCTAGCGGTGGTGGTGGTGGTGATCATAGGTT
GAATAATCAACCGAATCGGGTTGGGAATAATATGTATGCTTCGTCTCTAGGGTTG
CAAAGGCAATCCAGTGGGAGTAGTTTCGGTGAGAGCTCTTTGTCTGGGGATTATT
ACATGCCTACGCTTCTGCGGCGGCTAACGAGATCGAATCTGTTGGATTTCCTCA
AGATGATGGGTTTAGGCTTGGATTTGGTGGTGGTGGAGGAGATTTGAGGATACA
GATGGCGGCGGACTCCGCTGGAGGGTCTTCATCTGGGAAGAGCTGGGCGCAGCA
GACGGAGGAGAGTTATCAGCTGCAGCTTGCATTGGCGTTAAGGCTTTCGTCGGAG
GCTACTTGTGCCGACGATCCGAACTTTCTGGATCCTGTACCGGACGAGTCTGCTT
TACGGACTTCGCCAAGTTCAGCCGAAACCGTTTCACATCGTTTCTGGGTTAATGG
CTGCTTATCGTACTATGATAAAGTTCCTGATGGGTTTTATATGATGAATGGTCTGG
ATCCCTATATTTGGACCTTATGCATCGACCTGCATGAAAGTGGTCGCATCCCTTC
AATTGAATCATTAAGAGCTGTTGATTCTGGTGTTGATTCTTCGCTTGAAGCGATC
ATAGTTGATAGGCGTAGTGATCCAGCCTTCAAGGAACTTCACAATAGAGTCCACG
ACATATCTTGTAGCTGCATTACCACAAAAGAGGTTGTTGATCAGCTGGCAAAGCT
TATCTGCAATCGTATGGGGGGTCCAGTTATCATGGGGAAGATGAGTTGGTTCCC
ATGTGGAAGGAGTGCATTGATGGTCTAAAAGAAATCTTTAAAGTGGTGGTTCCCA
TAGGTAGCCTCTCTGTTGGACTCTGCAGACATCGAGCTTTACTCTTCAAAGTACT

Figure 23A Continued

GGCTGACATAATTGATTTACCCTGTCGAATTGCCAAAGGATGTAAATATTGTAAT
AGAGACGATGCCGCTTCGTGCCTTGTCAGGTTTGGGCTTGATAGGGAGTACCTGG
TTGATTTAGTAGGAAAGCCAGGTCACTTATGGGAGCCTGATTCCTTGCTAAATGG
TCCTTCATCTATCTCAATTTCTTCCTCTGCGGTTTCCACGACCAAAGCCAGTTG
AACCCGCAGTCGATTTTAGGTTACTAGCCAAACAATATTTCTCCGATAGCCAGTC
TCTTAATCTTGTTTTCGATCCTGCATCAGATGATATGGGATTCTCAATGTTTCATA
GGCAATATGATAATCCGGGTGGAGAGAATGACGCATTGGCAGAAAATGGTGGTG
GGTCTTTGCCACCCAGTGCTAATATGCCTCCACAGAACATGATGCGTGCGTCAAA
TCAAATTGAAGCAGCACCTATGAATGCCCCACCAATCAGTCAGCCAGTTCCAAAC
AGGGCAAATAGGGAACTTGGACTTGATGGTGATGATATGGACATCCCGTGGTGT
GATCTTAATATAAAAGAAAAGATTGGAGCAGGTTCCTTTGGCACTGTCCACCGTG
CTGAGTGGCATGGCTCGGATGTTGCTGTGAAAATTCTCATGGAGCAAGACTTCCA
TGCTGAGCGTGTTAATGAGTTCTTAAGAGAGGTTGCGATAATGAAACGCCTTCGC
CACCCTAACATTGTTCTCTTCATGGGTGCGGTCACTCAACCTCCAAATTTGTCAAT
AGTGACAGAATATTTGTCAAGAGGTAGTTTATACAGACTTTTGCATAAAAGTGGA
GCAAGGGAGCAATTAGATGAGAGACGTCGCCTGAGTATGGCTTATGATGTGGCT
AAGGGAATGAATTATCTTCACAATCGCAATCCTCCAATTGTGCATAGAGATCTAA
AATCTCCAAACTTATTGGTTGACAAAAAATATACAGTCAAGGTTTGTGATTTTGG
TCTCTCGCGATTGAAGGCCAGCACGTTTCTTTCCTCGAAGTCAGCAGCTGGAACC
CCCGAGTGGATGGCACCAGAAGTCCTGCGAGATGAGCCGTCTAATGAAAAGTCA
GATGTGTACAGCTTCGGGGTCATCTTGTGGGAGCTTGCTACATTGCAACAACCAT
GGGGTAACTTAAATCCGGCTCAGGTTGTAGCTGCGGTTGGTTTCAAGTGTAAACG
GCTGGAGATCCCGCGTAATCTGAATCCTCAGGTTGCAGCCATAATCGAGGGTTGT
TGGACCAATGAGCCATGGAAGCGTCCATCATTTGCAACTATAATGGACTTGCTAA
GACCATTGATCAAATCAGCGGTTCCTCCGCCCAACCGCTCGGATTTGTAA

Figure 23B

SEQ ID NO:48, Amino acid sequence of the open reading frame of pk107

MEMPGRRSNYTLLSQFSDDQVSVSVTGAPPPHYDSLSSENRSNHNSGNTGKAKAER
GGFDWDPSGGGGGDHRLNNQPNRVGNNMYASSLGLQRQSSGSSFGESSLSGDYYM
PTLSAAANEIESVGFPQDDGFRLGFGGGGGDLRIQMAADSAGGSSSGKSWAQQTEES
YQLQLALALRLSSEATCADDPNFLDPVPDESALRTSPSSAETVSHRFWVNGCLSYYD
KVPDGFYMMNGLDPYIWTLCIDLHESGRIPSIESLRAVDSGVDSSLEAIIVDRRSDPAF

Figure 23B Continued

KELHNRVHDISCSCITTKEVVDQLAKLICNRMGGPVIMGEDELVPMWKECIDGLKEI
FKVVVPIGSLSVGLCRHRALLFKVLADIIDLPCRIAKGCKYCNRDDAASCLVRFGLDR
EYLVDLVGKPGHLWEPDSLLNGPSSISISSPLRFPRPKPVEPAVDFRLLAKQYFSDSQS
LNLVFDPASDDMGFSMFHRQYDNPGGENDALAENGGGSLPPSANMPPQNMMRASN
QIEAAPMNAPPISQPVPNRANRELGLDGDDMDIPWCDLNIKEKIGAGSFGTVHRAEW
HGSDVAVKILMEQDFHAERVNEFLREVAIMKRLRHPNIVLFMGAVTQPPNLSIVTEY
LSRGSLYRLLHKSGAREQLDERRRLSMAYDVAKGMNYLHNRNPPIVHRDLKSPNLL
VDKKYTVKVCDFGLSRLKASTFLSSKSAAGTPEWMAPEVLRDEPSNEKSDVYSFGVI
LWELATLQQPWGNLNPAQVVAAVGFKCKRLEIPRNLNPQVAAIIEGCWTNEPWKRP
SFATIMDLLRPLIKSAVPPPNRSDL

SEQUENCE LISTING

<160> NUMBER OF SEQ ID NOS: 99

<210> SEQ ID NO 1
<211> LENGTH: 2253
<212> TYPE: DNA
<213> ORGANISM: Arabidopsis thaliana

<400> SEQUENCE: 1

```
atggttcgtc ctggattcat tatgcggccg cctggtacaa tcggtgctgt tcaactagca      60
ccacgacccc ttattccagg aatgcctggt ctccgtcctg taatgcctcc tatggttaga     120
ccggcttctc ttcctttgt aacacctgca gaaaagcccc agaccacaat ttacattggc      180
aagatagcta ccgtggaaaa tgactttatg atgtctattc ttgagttttg tggccatgtc     240
aaaagctgtt tacgtgcgga agatcctacc accaagaaac ctaaaggttt tggattctat     300
gaatttgaat cagctgaagg gattctccgc gcaatacgcc tgctgaccca acgtactata     360
gatggacaag agcttttggt gaatgttaat caagcaacaa aggagtattt gctaaaatat     420
gttgagaaga aaatagagac tgcaaagaaa gccaaggaaa gtcaaggaac caaagagaac     480
caagctgaag gtcctgagag tgagcaagac aagcttgaga gtgctgataa tgagacaggg     540
aaggatggag aatcgaagat taaagaaaac atcgatattg cgaattctgc tgtcctaact     600
gatgaagaaa gggaagcaga cagagaggct atggaaaaga ttgaaactgc tattgaagaa     660
aggttaaagt ccaacccttt gcctcctcca ccaccaccac ctgctgatgg ttcaggcatg     720
gaatttgctt tcaaatctaa ggatggtgac tccaacactg acgtagctag gagtgatgcc     780
gcagcaaatg atgttgagac ttctggagaa cacaataggc ctgacacaag ctcacctgat     840
tggagtaaga gaaatgaccg aagaggcaga gaaagaggtg agaaggagca agaaatggat     900
agatacgaga gggaggctga aagagaacgg tcaaggaaag agagagagca aaggaggaaa     960
cttgaggatg cagagcgtgc ttaccagact cgtcttcgac aatgggaacg aagagaaaga    1020
gaaaaggaga aggaacgaca gtacgagaag gagaaagaga aagagaaaga gcgcaagagg    1080
aaaaaggaaa tccgctatga ggaagaagag gaagaagacg atgatgattc aagaagaaga    1140
tggcataggg ctgcattaga tgagagaaga agacgacaac taagagaaaa ggaggatgac    1200
ttagctgata gattgaaaga agaggaagag gttgctgagg cgaagaggag tgccgaggag    1260
caaaatttgc agcaacagca attagatgcc ttaagaatcc tatcgggaca ggcagctatt    1320
ggaagcgaaa cggttcagac atcacctatt gaaaatgatc acaaggcaac tctccaaact    1380
```

```
gtcggtgaat ctgccaatga gcaccatgca gcagattttg aagaaaatgg ttctggtaat      1440
gaatcgatgg ctatcgataa taatagtgga tcagaggcac atgctccctc aaagaaatta      1500
ggatttgggc ttgtgggatc cggaaagcga acttctgtgc cttctgtttt ctatgaggag      1560
gatgaagatg aagcacgtaa ggctaaaaag atgaaacctt tggttcctat agattactca      1620
accgaggaac aagaggctgt ggcccatggt ggctcaggga atacaccacc tcatttggct      1680
ttagccgctg aatttgcaaa acgaatttcg agtaccaatc ccaaggaaga acgatagaa       1740 accgaaaaac aaaggagcag acgttctcat gataaggcaa gccaccggga cagggaaagg      1800
gaaagggaaa gggacaggga caggagatga gtcagggacc gaggtgacgg catagtggt       1860 cccaccaaag acgccaaaga gtctggaaaa gcaaagataa ttgatactaa gtttctggat      1920
gcgaaacaat tgatagatac aatcccaaag acaaaggaag atttattttc ttacgagata      1980
aactgggcta tgtatgacaa gcaccaagtg cacgaaagaa tgagaccatg gatctcaaag      2040
aaaattatgg agtttctcgg agaagaggaa gccactctgg tagatttcat cgtgtcaaac      2100
actcaacaac acgtgcaggc gtctcagatg cttgagctgt tgcaatcaat tctagacgaa      2160
gaagctgaga tgtttgtgct gaagatgtgg agaacgctca tctttgagat caagcgggtt      2220
gaagctggag tcccggtaaa atccaaagcc tga                                   2253

<210> SEQ ID NO 2
<211> LENGTH: 750
<212> TYPE: PRT
<213> ORGANISM: Arabidopsis thaliana

<400> SEQUENCE: 2

Met Val Arg Pro Gly Phe Ile Met Arg Pro Gly Thr Ile Gly Ala
 1               5                  10                  15

Val Gln Leu Ala Pro Arg Pro Leu Ile Pro Gly Met Pro Gly Leu Arg
                20                  25                  30

Pro Val Met Pro Pro Met Val Arg Pro Ala Ser Leu Pro Phe Val Thr
            35                  40                  45

Pro Ala Glu Lys Pro Gln Thr Thr Ile Tyr Ile Gly Lys Ile Ala Thr
        50                  55                  60

Val Glu Asn Asp Phe Met Met Ser Ile Leu Glu Phe Cys Gly His Val
 65                  70                  75                  80

Lys Ser Cys Leu Arg Ala Glu Asp Pro Thr Thr Lys Lys Pro Lys Gly
                85                  90                  95

Phe Gly Phe Tyr Glu Phe Glu Ser Ala Glu Gly Ile Leu Arg Ala Ile
            100                 105                 110

Arg Leu Leu Thr Gln Arg Thr Ile Asp Gly Gln Glu Leu Leu Val Asn
        115                 120                 125

Val Asn Gln Ala Thr Lys Glu Tyr Leu Leu Lys Tyr Val Glu Lys Lys
    130                 135                 140

Ile Glu Thr Ala Lys Lys Ala Lys Glu Ser Gln Gly Thr Lys Glu Asn
145                 150                 155                 160

Gln Ala Glu Gly Pro Glu Ser Glu Gln Asp Lys Leu Glu Ser Ala Asp
                165                 170                 175

Asn Glu Thr Gly Lys Asp Gly Glu Ser Lys Ile Lys Glu Asn Ile Asp
            180                 185                 190

Ile Ala Asn Ser Ala Val Leu Thr Asp Glu Glu Arg Glu Ala Asp Arg
        195                 200                 205

Glu Ala Met Glu Lys Ile Glu Thr Ala Ile Glu Glu Arg Leu Lys Ser
    210                 215                 220
```

```
Asn Pro Leu Pro Pro Pro Pro Pro Ala Asp Gly Ser Gly Met
225                 230                 235                 240

Glu Phe Ala Phe Lys Ser Lys Asp Gly Asp Ser Asn Thr Asp Val Ala
            245                 250                 255

Arg Ser Asp Ala Ala Asn Asp Val Glu Thr Ser Gly Glu His Asn
        260                 265                 270

Arg Pro Asp Thr Ser Ser Pro Asp Trp Ser Lys Arg Asn Asp Arg Arg
    275                 280                 285

Gly Arg Glu Arg Gly Glu Lys Glu Gln Glu Met Asp Arg Tyr Glu Arg
        290                 295                 300

Glu Ala Glu Arg Glu Arg Ser Arg Lys Glu Arg Glu Gln Arg Lys
305                 310                 315                 320

Leu Glu Asp Ala Glu Arg Ala Tyr Gln Thr Arg Leu Arg Gln Trp Glu
            325                 330                 335

Arg Arg Glu Arg Glu Lys Glu Lys Glu Arg Gln Tyr Glu Lys Glu Lys
            340                 345                 350

Glu Lys Glu Lys Glu Arg Lys Arg Lys Glu Ile Arg Tyr Glu Glu
    355                 360                 365

Glu Glu Glu Glu Asp Asp Asp Ser Arg Arg Arg Trp His Arg Ala
370                 375                 380

Ala Leu Asp Glu Arg Arg Arg Gln Leu Arg Glu Lys Glu Asp Asp
385                 390                 395                 400

Leu Ala Asp Arg Leu Lys Glu Glu Glu Val Ala Glu Ala Lys Arg
            405                 410                 415

Ser Ala Glu Glu Gln Asn Leu Gln Gln Gln Leu Asp Ala Leu Arg
        420                 425                 430

Ile Leu Ser Gly Gln Ala Ala Ile Gly Ser Glu Thr Val Gln Thr Ser
        435                 440                 445

Pro Ile Glu Asn Asp His Lys Ala Thr Leu Thr Val Gly Glu Ser
    450                 455                 460

Ala Asn Glu His His Ala Ala Asp Phe Glu Glu Asn Gly Ser Gly Asn
465                 470                 475                 480

Glu Ser Met Ala Ile Asp Asn Asn Ser Gly Ser Glu Ala His Ala Pro
            485                 490                 495

Ser Lys Lys Leu Gly Phe Gly Leu Val Gly Ser Gly Lys Arg Thr Ser
        500                 505                 510

Val Pro Ser Val Phe Tyr Glu Glu Asp Glu Asp Glu Ala Arg Lys Ala
        515                 520                 525

Lys Lys Met Lys Pro Leu Val Pro Ile Asp Tyr Ser Thr Glu Glu Gln
        530                 535                 540

Glu Ala Val Ala His Gly Gly Ser Gly Asn Thr Pro Pro His Leu Ala
545                 550                 555                 560

Leu Ala Ala Glu Phe Ala Lys Arg Ile Ser Ser Thr Asn Pro Lys Glu
            565                 570                 575

Glu Thr Ile Glu Thr Glu Lys Gln Arg Ser Arg Ser His Asp Lys
    580                 585                 590

Ala Ser His Arg Asp Arg Glu Arg Glu Arg Asp Arg Asp
        595                 600                 605

Asp Arg Val Arg Asp Arg Gly Asp Gly His Ser Gly Pro Thr Lys Asp
    610                 615                 620

Ala Lys Glu Ser Gly Lys Ala Lys Ile Ile Asp Thr Lys Phe Leu Asp
625                 630                 635                 640
```

```
Ala Lys Gln Leu Ile Asp Thr Ile Pro Lys Thr Lys Glu Asp Leu Phe
                645                 650                 655

Ser Tyr Glu Ile Asn Trp Ala Met Tyr Asp Lys His Gln Val His Glu
        660                 665                 670

Arg Met Arg Pro Trp Ile Ser Lys Lys Ile Met Glu Phe Leu Gly Glu
    675                 680                 685

Glu Glu Ala Thr Leu Val Asp Phe Ile Val Ser Asn Thr Gln Gln His
690                 695                 700

Val Gln Ala Ser Gln Met Leu Glu Leu Leu Gln Ser Ile Leu Asp Glu
705                 710                 715                 720

Glu Ala Glu Met Phe Val Leu Lys Met Trp Arg Thr Leu Ile Phe Glu
                725                 730                 735

Ile Lys Arg Val Glu Ala Gly Val Pro Val Lys Ser Lys Ala
            740                 745                 750
```

<210> SEQ ID NO 3
<211> LENGTH: 681
<212> TYPE: DNA
<213> ORGANISM: Arabidopsis thaliana

<400> SEQUENCE: 3

```
gtgctgaaaa agaagaaacc catacttact gacgagcatt tcgtagatgg tcggtttggt      60
tcgatgttcc aaaatccgga cttccaaatt gataaggact catatgaata tggtgtccta     120
caccctgttg cttcttcgaa gaagcaacct tctctgttag atgaacactt tgaagctgta     180
tcagatgatg acgagaacag tgattctgat gcatcacagc cttcagatga cgaggccgac     240
gatggagacg caactaggcc aagcaagaaa gcgagaactc cgaagttgta tgaagtgaaa     300
gatgagcggc atgccgcagc ttatcacaac cgcacttcac tggctaaaga agatagtctt     360
cctatgggcg agcgtgtcaa ggctatagag aaccggcgtg gcaactttgg aggctcgaaa     420
gatatcaaat tcggtcctgg aggatcacgg gagttttctt tcaaggcgag agggtcatca     480
aagtacaaag aagatagaga cgatgagtat gaagatggga aaagaaacaa gaggagagga     540
gttcagtctc ttggactgaa atcaacaaat attagaggcg gtttcagagg tagaggaggt     600
ggtggtttta gagggagagg aggcggcggt tcccggggaa aaggtggccg tggtggtggg     660
cgtggaagag gccggcaatg a                                                681
```

<210> SEQ ID NO 4
<211> LENGTH: 226
<212> TYPE: PRT
<213> ORGANISM: Arabidopsis thaliana

<400> SEQUENCE: 4

```
Val Leu Lys Lys Lys Pro Ile Leu Thr Asp Glu His Phe Val Asp
 1               5                  10                  15

Gly Arg Phe Gly Ser Met Phe Gln Asn Pro Asp Phe Gln Ile Asp Lys
                20                  25                  30

Asp Ser Tyr Glu Tyr Gly Val Leu His Pro Val Ala Ser Ser Lys Lys
            35                  40                  45

Gln Pro Ser Leu Leu Asp Glu His Phe Glu Ala Val Ser Asp Asp Asp
        50                  55                  60

Glu Asn Ser Asp Ser Asp Ala Ser Gln Pro Ser Asp Asp Glu Ala Asp
65                  70                  75                  80

Asp Gly Asp Ala Thr Arg Pro Ser Lys Lys Ala Arg Thr Pro Lys Leu
                85                  90                  95
```

```
Tyr Glu Val Lys Asp Glu Arg His Ala Ala Tyr His Asn Arg Thr
                100                 105                 110
Ser Leu Ala Lys Glu Asp Ser Leu Pro Met Gly Glu Arg Val Lys Ala
            115                 120                 125
Ile Glu Asn Arg Arg Gly Asn Phe Gly Gly Ser Lys Asp Ile Lys Phe
        130                 135                 140
Gly Pro Gly Gly Ser Arg Glu Phe Ser Phe Lys Ala Arg Gly Ser Ser
145                 150                 155                 160
Lys Tyr Lys Glu Asp Arg Asp Asp Glu Tyr Glu Asp Gly Gln Arg Asn
                165                 170                 175
Lys Arg Arg Gly Val Gln Ser Leu Gly Leu Lys Ser Thr Asn Ile Arg
            180                 185                 190
Gly Gly Phe Arg Gly Arg Gly Gly Gly Phe Arg Gly Arg Gly Gly
        195                 200                 205
Gly Gly Ser Arg Gly Lys Gly Gly Arg Gly Gly Arg Gly Arg Gly
    210                 215                 220
Arg Gln
225

<210> SEQ ID NO 5
<211> LENGTH: 1815
<212> TYPE: DNA
<213> ORGANISM: Arabidopsis thaliana

<400> SEQUENCE: 5
atggagcaga tgatattcat tagaaaagac gacaaagtag aggttttttc tgaagaagaa     60
gagttaaaag ggtcttatta cagagcgatt ctggaagata tccaacgaa  atcaggacac    120 aataagctta agttcgtta  cttgacgcag ctcaatgaac accgtttggc tcctttaacg    180
gaattcgtcg atcagaggtt cattcgtcct gtcccgtcgg aggatgtgaa cgacggcgtc    240 gttttttgtag aaggcttgat ggtcgacgct tatctcaaag atgggtggtg gactggtgtg    300
gtggtaaaaa caatggagga tgagaagttt ttggtttact tcgattgccc accagacatt    360
attcagtttg agaaaaagaa attgagggtt catcttgatt ggaccggctt caaatggatc    420
cgacctgata taaggaatt  ggtcaagtct gttttagtt  gcgggacaat ggtggaattg    480
agatttgatt gtgcttggat tccggtaatt gtcattaagg agttggagaa ggacaagagg    540
tttcttgtca agtactggaa taagtccat  agctgccggg aatcgaaaaa tttaattgtt    600
gattccctaa gactaaggcc tatgcagcct cctttatctg ttggaaagta tgaattgctg    660
gatcatgtag aggcgtttag tggttttgaa tggcgtcaag gtgtggtcag ggaattgtc     720 tttgagggaa ggtacatggt aagtttcggg gcaacaaagg aggcatcgca atttaatcac    780
tctgatatta ggcctccaat ggagtgggaa gatggagttt ggcataaaag aacaaagcca    840
aaacgccaga agaaaacttc tttagacggc aacagaaatg tgcagacaaa ggaaccaccg    900
ggaaatgaga tggctgatga tgtgaaaaaa gaatctggtt tacctataac cctgggggta    960
actgcaacaa agaacaaaac ccaaggaaag gtatcccctg tgccaatgaa gaatggcttt   1020
ggaaatgagt caactcgaga gaagatgcct gaggagccta agatcaaata ttatactcga   1080
aagaggaaaa gaggaggtct aaagctcaat tcatacatca ataagactgt gttatcctcg   1140
gatcggaccc ccaatgtggt gaagaattct gcttctaatg ctgaggaaaa ccatgcaaaa   1200
cacacaataa tggttttgcc ttttgcaaag aagtcaccgg tctggaagac ttatgaatca   1260
ctggaggtct tcaaaagtgt atcacacagt cttcatttca gcccattgtt tgagactaag   1320
```

-continued

```
caagatttcc gtgaagggta tgcaataggt atgatggtga cttattttgg gttactggag    1380
aaatttaaag atcttgaagc cgacgttcct gtaagccaac taaatagcct taaagattca    1440
ttttcggagc tcgagaaaca tggcttcaat gttacaactc cattatcacg gatcgacaag    1500
ctgtcagcac tcaaagatag acaactatat ataatggagg aactaaaagg ttttgacaag    1560
gagatgacaa atgaatttag caaggctaaa caagagtttg atgacatgga acaaaagatt    1620
cttgaggtga acacaagat tatcgagctg cagaggcaag aagctgctct aaaagaacaa    1680
aaggaagcag aaaaagaaca gaaagatgca gcctggaaaa agatatgtca gatggagtca    1740
tgcgcaaaag atctcaatgt agagcttgaa gatgtggagt ttgagtttga gacaattttg    1800
tcggctcctt ggtaa                                                     1815
```

<210> SEQ ID NO 6
<211> LENGTH: 604
<212> TYPE: PRT
<213> ORGANISM: Arabidopsis thaliana

<400> SEQUENCE: 6

```
Met Glu Gln Met Ile Phe Ile Arg Lys Asp Asp Lys Val Glu Val Phe
  1               5                  10                  15

Ser Glu Glu Glu Leu Lys Gly Ser Tyr Tyr Arg Ala Ile Leu Glu
             20                  25                  30

Asp Asn Pro Thr Lys Ser Gly His Asn Lys Leu Lys Val Arg Tyr Leu
         35                  40                  45

Thr Gln Leu Asn Glu His Arg Leu Ala Pro Leu Thr Glu Phe Val Asp
     50                  55                  60

Gln Arg Phe Ile Arg Pro Val Pro Ser Glu Asp Val Asn Asp Gly Val
 65                  70                  75                  80

Val Phe Val Glu Gly Leu Met Val Asp Ala Tyr Leu Lys Asp Gly Trp
                 85                  90                  95

Trp Thr Gly Val Val Lys Thr Met Glu Asp Glu Lys Phe Leu Val
            100                 105                 110

Tyr Phe Asp Cys Pro Pro Asp Ile Ile Gln Phe Glu Lys Lys Lys Leu
        115                 120                 125

Arg Val His Leu Asp Trp Thr Gly Phe Lys Trp Ile Arg Pro Asp Asn
    130                 135                 140

Lys Glu Leu Val Lys Ser Val Phe Ser Cys Gly Thr Met Val Glu Leu
145                 150                 155                 160

Arg Phe Asp Cys Ala Trp Ile Pro Val Ile Val Ile Lys Glu Leu Glu
                165                 170                 175

Lys Asp Lys Arg Phe Leu Val Lys Tyr Trp Asn Lys Ser Tyr Ser Cys
            180                 185                 190

Arg Glu Ser Lys Asn Leu Ile Val Asp Ser Leu Arg Leu Arg Pro Met
        195                 200                 205

Gln Pro Pro Leu Ser Val Gly Lys Tyr Glu Leu Leu Asp His Val Glu
    210                 215                 220

Ala Phe Ser Gly Phe Glu Trp Arg Gln Gly Val Val Arg Gly Ile Val
225                 230                 235                 240

Phe Glu Gly Arg Tyr Met Val Ser Phe Gly Ala Thr Lys Glu Ala Ser
                245                 250                 255

Gln Phe Asn His Ser Asp Ile Arg Pro Pro Met Glu Trp Glu Asp Gly
            260                 265                 270

Val Trp His Lys Arg Thr Lys Pro Lys Arg Gln Lys Glu Thr Ser Leu
        275                 280                 285
```

| | | | | | | | | | | | |
|---|---|---|---|---|---|---|---|---|---|---|---|
| Asp | Gly | Asn | Arg | Asn | Val | Gln | Thr | Lys | Glu | Pro | Pro | Gly | Asn | Glu | Met |
| | | 290 | | | | 295 | | | | 300 | |
| Ala | Asp | Asp | Val | Lys | Lys | Glu | Ser | Gly | Leu | Pro | Ile | Thr | Leu | Gly | Val |
| 305 | | | | | 310 | | | | | 315 | | | | | 320 |
| Thr | Ala | Thr | Lys | Asn | Lys | Thr | Gln | Gly | Lys | Val | Ser | Pro | Val | Pro | Met |
| | | | | 325 | | | | | 330 | | | | | 335 |
| Lys | Asn | Gly | Phe | Gly | Asn | Glu | Ser | Thr | Arg | Glu | Lys | Met | Pro | Glu | Glu |
| | | | 340 | | | | | 345 | | | | | 350 |
| Pro | Lys | Ile | Lys | Tyr | Tyr | Thr | Arg | Lys | Arg | Lys | Arg | Gly | Gly | Leu | Lys |
| | | 355 | | | | | 360 | | | | | 365 |
| Leu | Asn | Ser | Tyr | Ile | Asn | Lys | Thr | Val | Leu | Ser | Ser | Asp | Arg | Thr | Pro |
| | 370 | | | | | 375 | | | | | 380 |
| Asn | Val | Val | Lys | Asn | Ser | Ala | Ser | Asn | Ala | Glu | Glu | Asn | His | Ala | Lys |
| 385 | | | | | 390 | | | | | 395 | | | | | 400 |
| His | Thr | Ile | Met | Val | Leu | Pro | Phe | Ala | Lys | Lys | Ser | Pro | Val | Trp | Lys |
| | | | | 405 | | | | | 410 | | | | | 415 |
| Thr | Tyr | Glu | Ser | Leu | Glu | Val | Phe | Lys | Ser | Val | Ser | His | Ser | Leu | His |
| | | | 420 | | | | | 425 | | | | | 430 |
| Phe | Ser | Pro | Leu | Phe | Glu | Thr | Lys | Gln | Asp | Phe | Arg | Glu | Gly | Tyr | Ala |
| | | 435 | | | | | 440 | | | | | 445 |
| Ile | Gly | Met | Met | Val | Thr | Tyr | Phe | Gly | Leu | Leu | Glu | Lys | Phe | Lys | Asp |
| | 450 | | | | | 455 | | | | | 460 |
| Leu | Glu | Ala | Asp | Val | Pro | Val | Ser | Gln | Leu | Asn | Ser | Leu | Lys | Asp | Ser |
| 465 | | | | | 470 | | | | | 475 | | | | | 480 |
| Phe | Ser | Glu | Leu | Glu | Lys | His | Gly | Phe | Asn | Val | Thr | Thr | Pro | Leu | Ser |
| | | | | 485 | | | | | 490 | | | | | 495 |
| Arg | Ile | Asp | Lys | Leu | Ser | Ala | Leu | Lys | Asp | Arg | Gln | Leu | Tyr | Ile | Met |
| | | | 500 | | | | | 505 | | | | | 510 |
| Glu | Glu | Leu | Lys | Gly | Phe | Asp | Lys | Glu | Met | Thr | Asn | Glu | Phe | Ser | Lys |
| | | 515 | | | | | 520 | | | | | 525 |
| Ala | Lys | Gln | Glu | Phe | Asp | Asp | Met | Glu | Gln | Lys | Ile | Leu | Glu | Val | Lys |
| | 530 | | | | | 535 | | | | | 540 |
| His | Lys | Ile | Ile | Glu | Leu | Gln | Arg | Gln | Glu | Ala | Ala | Leu | Lys | Glu | Gln |
| 545 | | | | | 550 | | | | | 555 | | | | | 560 |
| Lys | Glu | Ala | Glu | Lys | Glu | Gln | Lys | Asp | Ala | Ala | Trp | Lys | Lys | Ile | Cys |
| | | | | 565 | | | | | 570 | | | | | 575 |
| Gln | Met | Glu | Ser | Cys | Ala | Lys | Asp | Leu | Asn | Val | Glu | Leu | Glu | Asp | Val |
| | | | 580 | | | | | 585 | | | | | 590 |
| Glu | Phe | Glu | Phe | Glu | Thr | Ile | Leu | Ser | Ala | Pro | Trp |
| | | 595 | | | | | 600 |

<210> SEQ ID NO 7
<211> LENGTH: 1773
<212> TYPE: DNA
<213> ORGANISM: Arabidopsis thaliana

<400> SEQUENCE: 7

```
atggctatgg tagatgaacc gttgtatccc attgctgtgc ttatagatga gcttaagaat    60
gatgatattc agcttcgttt gaactcgatc cgtcgcttat ctactatagc tcgtgctctt   120
ggagaggagc gtacaaggaa ggagttaatc ccttttttga gtgagaatag tgacgatgac   180
gatgaggtgc ttcttgcaat ggctgaggag ttaggagttt ttattccgtt tgttggagga   240
attgagtttg cgcatgttct tcttcctcct ttggaatctc tatgtactgt tgaagagact   300
```

```
tgtgtgagag gaaaagctgt ggaatcgctt tgtaagattg gatctcagat gaaagagaat    360
gatcttgttg aatcttttgt tcctcttgtg aagaggttag cgggtggtga atggtttgca    420
gcaagagttt ctgcatgtgg tatatttcat gttgcatacc aaggttgcac tgatgttttg    480
aagactgagt tacgggctac ttatagccag ttgtgcaaag atgatatgcc aatggtgcga    540
agagctgctg catctaacct ggggaaattt gctacaactg tcgagtctac cttttgatt    600
gctgagatca tgactatgtt cgatgatctt actaaagatg accaagattc tgtgagacta    660
ttggctgttg aagggtgtgc agctcttgga aagttgttgg aacctcagga ttgtgttgca    720
cgcattttac ctgttattgt taatttctct caggataaat cttggagggt gcgctacatg    780
gttgcaaatc agctatatga actttgtaag gcagtgggtc ctgattgcac gaggacggat    840
ttggttccag catatgtaag attgctaagg acaatgagg ctgaagtgcg aatagcagca    900
gcgggaaaag tgaccaagtt ctgtcggctt ttgaatccag agcttgcgat tcagcacatc    960
cttcctgtg tgaaggaatt atcatcggat tcttctcaac atgtccgctc tgctctagct    1020
tcagtaataa tggggatggc tcctatcctt ggaaggact caaccattga gcatctgtta    1080
ccaattttc tttccctttt gaaagatgaa tttcctgatg tgcgccttaa catcataagc    1140
aagttagatc aagtcaacca ggttattgga attgatctac tatctcaatc cttgttaccg    1200
gccattgtag aacttgctga ggatcggcac tggagagtcc gacttgcaat aatagagtat    1260
gttccactgt tggccagcca gttaggtata ggattttttcg attacaagct cggagcccct    1320
tgcatgcaat ggctgcaaga caaggtctac tctatccgcg aagctgcagc tgcagcaaac    1380
aacctaaagc gcctcgcaga ggagtttggt cctgaatggg caatgcagca cttagttccc    1440
caggtattgg acatggtcaa caatccgcac tacctacaca ggatgatggt tctacgcgca    1500
atatctctca tggcgcctgt aatgggatca gaaatcacat gctctaagtt tcttcctgtg    1560
gttgttgaag catcaaaaga cagagttcca acatcaagt tcaacgttgc caaacttctg    1620
caatccctca tccccatagt cgaccaatca gtggtggaca aaacaatccg tcagtgtttg    1680
gtggacctga gcgaagaccc tgatgttgat gttcgttatt ttgcaaatca agcacttaat    1740
tccatcgatg gttccacagc agcacaatcc tga                                 1773
```

<210> SEQ ID NO 8
<211> LENGTH: 590
<212> TYPE: PRT
<213> ORGANISM: Arabidopsis thaliana

<400> SEQUENCE: 8

```
Met Ala Met Val Asp Glu Pro Leu Tyr Pro Ile Ala Val Leu Ile Asp
  1               5                  10                  15

Glu Leu Lys Asn Asp Asp Ile Gln Leu Arg Leu Asn Ser Ile Arg Arg
             20                  25                  30

Leu Ser Thr Ile Ala Arg Ala Leu Gly Glu Glu Arg Thr Arg Lys Glu
         35                  40                  45

Leu Ile Pro Phe Leu Ser Glu Asn Ser Asp Asp Asp Asp Glu Val Leu
     50                  55                  60

Leu Ala Met Ala Glu Glu Leu Gly Val Phe Ile Pro Phe Val Gly Gly
 65                  70                  75                  80

Ile Glu Phe Ala His Val Leu Leu Pro Pro Leu Glu Ser Leu Cys Thr
                 85                  90                  95

Val Glu Glu Thr Cys Val Arg Gly Lys Ala Val Glu Ser Leu Cys Lys
            100                 105                 110
```

-continued

```
Ile Gly Ser Gln Met Lys Glu Asn Asp Leu Val Glu Ser Phe Val Pro
            115                 120                 125

Leu Val Lys Arg Leu Ala Gly Gly Glu Trp Phe Ala Ala Arg Val Ser
130                 135                 140

Ala Cys Gly Ile Phe His Val Ala Tyr Gln Gly Cys Thr Asp Val Leu
145                 150                 155                 160

Lys Thr Glu Leu Arg Ala Thr Tyr Ser Gln Leu Cys Lys Asp Met
                165                 170                 175

Pro Met Val Arg Arg Ala Ala Ser Asn Leu Gly Lys Phe Ala Thr
                180                 185                 190

Thr Val Glu Ser Thr Phe Leu Ile Ala Glu Ile Met Thr Met Phe Asp
                195                 200                 205

Asp Leu Thr Lys Asp Asp Gln Asp Ser Val Arg Leu Leu Ala Val Glu
    210                 215                 220

Gly Cys Ala Ala Leu Gly Lys Leu Leu Glu Pro Gln Asp Cys Val Ala
225                 230                 235                 240

Arg Ile Leu Pro Val Ile Val Asn Phe Ser Gln Asp Lys Ser Trp Arg
                245                 250                 255

Val Arg Tyr Met Val Ala Asn Gln Leu Tyr Glu Leu Cys Lys Ala Val
                260                 265                 270

Gly Pro Asp Cys Thr Arg Thr Asp Leu Val Pro Ala Tyr Val Arg Leu
                275                 280                 285

Leu Arg Asp Asn Glu Ala Glu Val Arg Ile Ala Ala Ala Gly Lys Val
                290                 295                 300

Thr Lys Phe Cys Arg Leu Leu Asn Pro Glu Leu Ala Ile Gln His Ile
305                 310                 315                 320

Leu Pro Cys Val Lys Glu Leu Ser Ser Asp Ser Ser Gln His Val Arg
                325                 330                 335

Ser Ala Leu Ala Ser Val Ile Met Gly Met Ala Pro Ile Leu Gly Lys
                340                 345                 350

Asp Ser Thr Ile Glu His Leu Leu Pro Ile Phe Leu Ser Leu Leu Lys
                355                 360                 365

Asp Glu Phe Pro Asp Val Arg Leu Asn Ile Ile Ser Lys Leu Asp Gln
                370                 375                 380

Val Asn Gln Val Ile Gly Ile Asp Leu Leu Ser Gln Ser Leu Leu Pro
385                 390                 395                 400

Ala Ile Val Glu Leu Ala Glu Asp Arg His Trp Arg Val Arg Leu Ala
                405                 410                 415

Ile Ile Glu Tyr Val Pro Leu Leu Ala Ser Gln Leu Gly Ile Gly Phe
                420                 425                 430

Phe Asp Tyr Lys Leu Gly Ala Leu Cys Met Gln Trp Leu Gln Asp Lys
                435                 440                 445

Val Tyr Ser Ile Arg Glu Ala Ala Ala Ala Asn Asn Leu Lys Arg
    450                 455                 460

Leu Ala Glu Glu Phe Gly Pro Glu Trp Ala Met Gln His Leu Val Pro
465                 470                 475                 480

Gln Val Leu Asp Met Val Asn Asn Pro His Tyr Leu His Arg Met Met
                485                 490                 495

Val Leu Arg Ala Ile Ser Leu Met Ala Pro Val Met Gly Ser Glu Ile
                500                 505                 510

Thr Cys Ser Lys Phe Leu Pro Val Val Glu Ala Ser Lys Asp Arg
                515                 520                 525

Val Pro Asn Ile Lys Phe Asn Val Ala Lys Leu Leu Gln Ser Leu Ile
```

```
                530              535             540
    Pro Ile Val Asp Gln Ser Val Asp Lys Thr Ile Arg Gln Cys Leu
    545                 550                 555                 560

Val Asp Leu Ser Glu Asp Pro Asp Val Asp Val Arg Tyr Phe Ala Asn
                    565                 570                 575

Gln Ala Leu Asn Ser Ile Asp Gly Ser Thr Ala Ala Gln Ser
                580                 585                 590

<210> SEQ ID NO 9
<211> LENGTH: 1035
<212> TYPE: DNA
<213> ORGANISM: Arabidopsis thaliana

<400> SEQUENCE: 9
atgaccacgt tattcctcct tattgctcta ttcatcacaa ccatcctcaa cccaacaagt      60
ggagaatcag taggtgtatg ctatggaatg atggggaaca accttccttc tcaatcagac     120
acaatcgctc tctttagaca aaacaacatc gacgtgtta  gactctacga tccaaaccaa     180
gccgctttaa acgctcttag aaacacgggt atcgaagtca tcatcggcgt tccaaacacc     240
gatcttcgtt cactcactaa cccttcttcc gctagatcat ggctccaaaa caacgtcctc     300
aactattacc ccgccgttag cttcaagtac atcgccgtag gtaacgaagt atctccgtcg     360
aacggcggtg atgttgtgct ccctgccatg cgtaacgttt acgatgctct aagaggtgca     420
aatcttcaag atcgtattaa agtttctacc gccattgata tgactttgat tggaaactct     480
ttccctcctt cctccggaga gtttcgtggt gacgttagat ggtatatcga tcccgtcatc     540
gggtttctta cgagtacgaa ctcagcgtta ctagccaaca tctatcctta cttcagctac     600
gttgacaatc cacgtgacat atctctctct tacgctctct tcacttctcc ttccgtcgtc     660
gtatgggacg gctctcgtgg ctaccaaaac ctctttgacg ctttacttga cgttgtttac     720
tctgccgttg aacgctcagg cggtggatct ctcccagtgg ttgtttccga gagcggatgg     780
ccttctaacg gtggaaacgc cgcgagtttc gataacgcgc gagctttta  cacgaatctt     840 gcgtcgcgtg tgagagagaa cagaggaaca ccgaagagac ctggaagagg agtgaaaacg     900
tatttgttcg ctatgtttga tgagaatcaa aagagtcctg agatcgagaa gaattttggt     960
ttgttttttc ctaataaaca accaaaattt ccgatcacat tctctgccgc gagagacggt    1020
acggcggttg agtga                                                     1035

<210> SEQ ID NO 10
<211> LENGTH: 344
<212> TYPE: PRT
<213> ORGANISM: Arabidopsis thaliana

<400> SEQUENCE: 10

Met Thr Thr Leu Phe Leu Leu Ile Ala Leu Phe Ile Thr Thr Ile Leu
1                   5                   10                  15

Asn Pro Thr Ser Gly Glu Ser Val Gly Val Cys Tyr Gly Met Met Gly
                20                  25                  30

Asn Asn Leu Pro Ser Gln Ser Asp Thr Ile Ala Leu Phe Arg Gln Asn
            35                  40                  45

Asn Ile Arg Arg Val Arg Leu Tyr Asp Pro Asn Gln Ala Ala Leu Asn
        50                  55                  60

Ala Leu Arg Asn Thr Gly Ile Glu Val Ile Ile Gly Val Pro Asn Thr
65                  70                  75                  80

Asp Leu Arg Ser Leu Thr Asn Pro Ser Ser Ala Arg Ser Trp Leu Gln
```

|   |   | 85 |   |   |   | 90 |   |   |   | 95 |   |
|---|---|---|---|---|---|---|---|---|---|---|---|

Asn Asn Val Leu Asn Tyr Tyr Pro Ala Val Ser Phe Lys Tyr Ile Ala
                 100                 105                 110

Val Gly Asn Glu Val Ser Pro Ser Asn Gly Gly Asp Val Val Leu Pro
            115                 120                 125

Ala Met Arg Asn Val Tyr Asp Ala Leu Arg Gly Ala Asn Leu Gln Asp
    130                 135                 140

Arg Ile Lys Val Ser Thr Ala Ile Asp Met Thr Leu Ile Gly Asn Ser
145                 150                 155                 160

Phe Pro Pro Ser Ser Gly Glu Phe Arg Gly Asp Val Arg Trp Tyr Ile
                165                 170                 175

Asp Pro Val Ile Gly Phe Leu Thr Ser Thr Asn Ser Ala Leu Leu Ala
            180                 185                 190

Asn Ile Tyr Pro Tyr Phe Ser Tyr Val Asp Asn Pro Arg Asp Ile Ser
        195                 200                 205

Leu Ser Tyr Ala Leu Phe Thr Ser Pro Ser Val Val Val Trp Asp Gly
    210                 215                 220

Ser Arg Gly Tyr Gln Asn Leu Phe Asp Ala Leu Leu Asp Val Val Tyr
225                 230                 235                 240

Ser Ala Val Glu Arg Ser Gly Gly Gly Ser Leu Pro Val Val Val Ser
                245                 250                 255

Glu Ser Gly Trp Pro Ser Asn Gly Gly Asn Ala Ala Ser Phe Asp Asn
            260                 265                 270

Ala Arg Ala Phe Tyr Thr Asn Leu Ala Ser Arg Val Arg Glu Asn Arg
        275                 280                 285

Gly Thr Pro Lys Arg Pro Gly Arg Gly Val Glu Thr Tyr Leu Phe Ala
    290                 295                 300

Met Phe Asp Glu Asn Gln Lys Ser Pro Glu Ile Glu Lys Asn Phe Gly
305                 310                 315                 320

Leu Phe Phe Pro Asn Lys Gln Pro Lys Phe Pro Ile Thr Phe Ser Ala
                325                 330                 335

Ala Arg Asp Gly Thr Ala Val Glu
            340

<210> SEQ ID NO 11
<211> LENGTH: 804
<212> TYPE: DNA
<213> ORGANISM: Arabidopsis thaliana

<400> SEQUENCE: 11
gtgtccatca ctggaaaggg agtgaaagcc accgttaaag gtagagagat tatggtgggg    60
aacaagaatc tgatgaatga tcataaagtt attattccag atgatgctga agagttgcta   120
gctgactctg aagatatggc ccagaccgga attcttgtct ccataaacag tgaactgatt   180
ggagttttgt ctgtttcgga tcctctaaaa ccgagtgctc gagaagccat ctccattcta   240
aaatccatga atatcaaaag catcatggta actggtggca actggggaac agcaaactca   300
attgctagag aagtcggtat cgactctgtt atcgcagaag ctaaacctga gcaaaaagca   360
gagaaagtca aggaattaca ggctgcggga catgttgtgg caatggtagg tgacggaatc   420
aatgactcac cggctctcgt ggcagcggat gtaggtatgg cgataggtgc aggaacagac   480
attgctatag aagcagcgga tatagttctg atggaaagca acttagaaga tgtgatcaca   540
gccattgatc tttcaaggaa aacgttctca agaatccgtc tcaactacgt atgggctctc   600
gggtataacc tcatggggat accgatcgct gcgggagtgc ttttcccagg gacacgtttc   660

```
aggttgcctc catggattgc aggtgctgca atggctgctt cttctgttag tgttgtgtgt    720
tgctctctct tgcttaagaa ctacaagcga cctaagaagc ttgatcatct ggagattcgg    780
gagattcagg tggagcgagt ttaa                                           804
```

<210> SEQ ID NO 12
<211> LENGTH: 267
<212> TYPE: PRT
<213> ORGANISM: Arabidopsis thaliana

<400> SEQUENCE: 12

```
Val Ser Ile Thr Gly Lys Gly Val Lys Ala Thr Val Lys Gly Arg Glu
 1               5                  10                  15

Ile Met Val Gly Asn Lys Asn Leu Met Asn Asp His Lys Val Ile Ile
             20                  25                  30

Pro Asp Asp Ala Glu Glu Leu Leu Ala Asp Ser Glu Asp Met Ala Gln
         35                  40                  45

Thr Gly Ile Leu Val Ser Ile Asn Ser Glu Leu Ile Gly Val Leu Ser
     50                  55                  60

Val Ser Asp Pro Leu Lys Pro Ser Ala Arg Glu Ala Ile Ser Ile Leu
 65                  70                  75                  80

Lys Ser Met Asn Ile Lys Ser Ile Met Val Thr Gly Gly Asn Trp Gly
                 85                  90                  95

Thr Ala Asn Ser Ile Ala Arg Glu Val Gly Ile Asp Ser Val Ile Ala
            100                 105                 110

Glu Ala Lys Pro Glu Gln Lys Ala Glu Lys Val Lys Glu Leu Gln Ala
        115                 120                 125

Ala Gly His Val Val Ala Met Val Gly Asp Gly Ile Asn Asp Ser Pro
    130                 135                 140

Ala Leu Val Ala Ala Asp Val Gly Met Ala Ile Gly Ala Gly Thr Asp
145                 150                 155                 160

Ile Ala Ile Glu Ala Ala Asp Ile Val Leu Met Glu Ser Asn Leu Glu
                165                 170                 175

Asp Val Ile Thr Ala Ile Asp Leu Ser Arg Lys Thr Phe Ser Arg Ile
            180                 185                 190

Arg Leu Asn Tyr Val Trp Ala Leu Gly Tyr Asn Leu Met Gly Ile Pro
        195                 200                 205

Ile Ala Ala Gly Val Leu Phe Pro Gly Thr Arg Phe Arg Leu Pro Pro
    210                 215                 220

Trp Ile Ala Gly Ala Ala Met Ala Ala Ser Ser Val Ser Val Val Cys
225                 230                 235                 240

Cys Ser Leu Leu Leu Lys Asn Tyr Lys Arg Pro Lys Lys Leu Asp His
                245                 250                 255

Leu Glu Ile Arg Glu Ile Gln Val Glu Arg Val
            260                 265
```

<210> SEQ ID NO 13
<211> LENGTH: 273
<212> TYPE: DNA
<213> ORGANISM: Arabidopsis thaliana

<400> SEQUENCE: 13

```
gtggccatgg aaggagaatt tcaggatgag cttgtggttg ttggagatgg agtggattca     60
gcttctttga ttatggcctt aaggaagaaa gcatgtcatg tcactcttga gactcttgaa    120
gaagtgaaga agccacaggt cgaagagaag tctattacac cgcattgctg catagctcaa    180
```

```
tgtcctgtgg ttagcaatga gcagccaagg cctgaggttt atagaatagt gcatgattct    240
tatggtccaa ccactgggtg cttagttatg taa                                  273

<210> SEQ ID NO 14
<211> LENGTH: 90
<212> TYPE: PRT
<213> ORGANISM: Arabidopsis thaliana

<400> SEQUENCE: 14

Val Ala Met Glu Gly Glu Phe Gln Asp Glu Leu Val Val Val Gly Asp
 1               5                  10                  15

Gly Val Asp Ser Ala Ser Leu Ile Met Ala Leu Arg Lys Lys Ala Cys
                20                  25                  30

His Val Thr Leu Glu Thr Leu Glu Glu Val Lys Lys Pro Gln Val Glu
            35                  40                  45

Glu Lys Ser Ile Thr Pro His Cys Cys Ile Ala Gln Cys Pro Val Val
        50                  55                  60

Ser Asn Glu Gln Pro Arg Pro Glu Val Tyr Arg Ile Val His Asp Ser
65                  70                  75                  80

Tyr Gly Pro Thr Thr Gly Cys Leu Val Met
                85                  90

<210> SEQ ID NO 15
<211> LENGTH: 603
<212> TYPE: DNA
<213> ORGANISM: Arabidopsis thaliana

<400> SEQUENCE: 15
atggtcttga ttactaagat gtctctctct ttctacatca ttcatcttct catttctcc     60 ttgatttcca cttgtgttgt ctccaaccag gccgaggata atcttcttca aggcctaaac   120
agctaccgaa ctgctcaaag agttcctcca tttgccaaga atgagaaggc tgattgtgtg   180
gctgatgaga tcgccgacaa gctcgaagat cagccatgca caaccacac acagcgagc    240 acggttactc ctggctcggt acctccacgg ctgacgaact accaggacat tctctctgaa   300
tgcaaaatcg acccaaacac tacccgtgac ggattgatct tacctgtctg tatccctaac   360
cggatcccga ctttggcttt aactaattac acccaaactg ttatgctcg gtatcttaat    420 gattcgaggt atgtcgggc tggtgttggg tcggagaaag agtggatggt ggttgtattg    480
acgacaagta ctccaggtgg aagctttaca gctggtgttg ctgctggcaa ggcgacgtct   540
gtgagagtaa tggctggttt agggctaatg gggttgttgt ttagttgcct tgtgctcttc   600
tga                                                                603

<210> SEQ ID NO 16
<211> LENGTH: 200
<212> TYPE: PRT
<213> ORGANISM: Arabidopsis thaliana

<400> SEQUENCE: 16

Met Val Leu Ile Thr Lys Met Ser Leu Ser Phe Tyr Ile Ile His Leu
 1               5                  10                  15

Leu Ile Phe Ser Leu Ile Ser Thr Cys Val Val Ser Asn Gln Ala Glu
                20                  25                  30

Asp Asn Leu Leu Gln Gly Leu Asn Ser Tyr Arg Thr Ala Gln Arg Val
            35                  40                  45

Pro Pro Phe Ala Lys Asn Glu Lys Ala Asp Cys Val Ala Asp Glu Ile
```

```
            50                  55                  60
Ala Asp Lys Leu Glu Asp Gln Pro Cys Thr Asn His Thr Thr Ala Ser
         65                  70                  75                  80

Thr Val Thr Pro Gly Ser Val Pro Pro Arg Leu Thr Asn Tyr Gln Asp
                     85                  90                  95

Ile Leu Ser Glu Cys Lys Ile Asp Pro Asn Thr Thr Arg Asp Gly Leu
                100                 105                 110

Ile Leu Pro Val Cys Ile Pro Asn Arg Ile Pro Thr Leu Ala Leu Thr
            115                 120                 125

Asn Tyr Thr Gln Thr Gly Tyr Ala Arg Tyr Leu Asn Asp Ser Arg Tyr
        130                 135                 140

Val Gly Ala Gly Val Gly Ser Glu Lys Glu Trp Met Val Val Val Leu
145                 150                 155                 160

Thr Thr Ser Thr Pro Gly Gly Ser Phe Thr Ala Gly Val Ala Ala Gly
                165                 170                 175

Lys Ala Thr Ser Val Arg Val Met Ala Gly Leu Gly Leu Met Gly Leu
            180                 185                 190

Leu Phe Ser Cys Leu Val Leu Phe
        195                 200

<210> SEQ ID NO 17
<211> LENGTH: 1746
<212> TYPE: DNA
<213> ORGANISM: Arabidopsis thaliana

<400> SEQUENCE: 17
atggagaaag tgaccaactc agacttgaaa tcctctgttg atggtggcgt tgttgatgtg      60
tatgagaaag attcagccac cattgagcac aacataactc cttggtctct ctctgtttct     120
agtggatatt cattgctgag agatcctcgc tacaacaaag gacttgcttt cactgagaaa     180
gagagagaca ctcattactt gcgtggtctt ctccctccag ttgttcttga tcaaaagctt     240
caggagaaga ggctgttgaa caatatccga caatatcaat tcccattaca aaagtacatg     300
gctctgacag aacttcagga agaaacgag agactgtttt acgagctatt gatagataat      360
gttgaggagc tacttcctat tgtttatact ccaactgttg tgaagcttg tcagaaattt      420 ggaagtattt tcaggcgacc tcagggttta ttcatcagtt taaaagacaa gggaaagatt     480
ctagatgtgt taagaactg gcctgaaagg aacatacagg ttattgttgt tactgacggt      540
gaaaggattt taggattagg agatcttgga tgtcagggga tgggtatacc ggttggtaag     600
ttggcgttat attcagcact ggaggtgtt cgtccttcag cgtgtttacc tgtcaccatt      660
gatgtgggaa caacaatga aaactgttg aatgatgagt tctacatagg actcaggcaa      720
aagagagcaa cgggacagga atatagtgaa ctcttgaatg aattcatgag tgctgtgaaa     780
cagaactatg gtgaaaaagt tcttattcag tttgaagatt ttgctaatca taatgccttt     840
gagttgcttg caaaatacag cgatactcat ctcgtcttca acgatgatat acaggggaca     900
gcatcagttg ttttagcagg attagtttcc gcacagaagt taacgaatag cccacttgca     960
gagcatacct tcctctttct tggtgctggt gaagctggaa ctggaatagc agaactcata    1020
gctctctata tgtcaaaaca gatgaatgct tcggtagagg aaagccgcaa gaaaatctgg    1080
cttgttgatt ccaagggatt gattgttaac tcccgcaaag attcacttca agactttaag    1140
aaaccatggg ctcatgaaca tgaaccagtc aaagacctct taggtgctat caaggcaata    1200
aaaccgactg ttctgattgg atcttctggc gttggacggt cttttacaaa agaagtgata    1260
```

```
gaagccatgt cctccattaa tgagagacca ctgataatgg ctctctctaa ccccacaaca    1320
caatctgaat gtacagccga agaagcttat acttggagta agggccgtgc cattttttgct   1380 agtggaagcc cttttgatcc agttgagtat gaaggaaagg tgtttgtatc tacacaggcg    1440
aacaatgcgt acatattccc gggctttgga cttggtttgg ttatctctgg agcaatacgg    1500
gtacatgacg atatgcttct agctgctgct gaggcattag ctggacaagt aagcaaagag    1560
aactatgaga aaggaatgat atatccttca ttctcttcca tccggaaaat atcagctcag    1620
attgcagcca atgtagcaac taaggcgtat gaactaggat tggcagggcg gcttccacgg    1680
ccgaaagata ttgtcaaatg tgcagagagt agcatgtaca gccccacata ccgtctctac    1740
cgttga                                                              1746
```

<210> SEQ ID NO 18
<211> LENGTH: 581
<212> TYPE: PRT
<213> ORGANISM: Arabidopsis thaliana

<400> SEQUENCE: 18

```
Met Glu Lys Val Thr Asn Ser Asp Leu Lys Ser Val Asp Gly Gly
 1               5                  10                  15

Val Val Asp Val Tyr Gly Glu Asp Ser Ala Thr Ile Glu His Asn Ile
                20                  25                  30

Thr Pro Trp Ser Leu Ser Val Ser Gly Tyr Ser Leu Leu Arg Asp
         35                  40                  45

Pro Arg Tyr Asn Lys Gly Leu Ala Phe Thr Glu Lys Glu Arg Asp Thr
     50                  55                  60

His Tyr Leu Arg Gly Leu Leu Pro Pro Val Val Leu Asp Gln Lys Leu
 65                  70                  75                  80

Gln Glu Lys Arg Leu Leu Asn Asn Ile Arg Gln Tyr Gln Phe Pro Leu
                 85                  90                  95

Gln Lys Tyr Met Ala Leu Thr Glu Leu Gln Glu Arg Asn Glu Arg Leu
            100                 105                 110

Phe Tyr Glu Leu Leu Ile Asp Asn Val Glu Glu Leu Leu Pro Ile Val
        115                 120                 125

Tyr Thr Pro Thr Val Gly Glu Ala Cys Gln Lys Phe Gly Ser Ile Phe
    130                 135                 140

Arg Arg Pro Gln Gly Leu Phe Ile Ser Leu Lys Asp Lys Gly Lys Ile
145                 150                 155                 160

Leu Asp Val Leu Lys Asn Trp Pro Glu Arg Asn Ile Gln Val Ile Val
                165                 170                 175

Val Thr Asp Gly Glu Arg Ile Leu Gly Leu Gly Asp Leu Gly Cys Gln
            180                 185                 190

Gly Met Gly Ile Pro Val Gly Lys Leu Ala Leu Tyr Ser Ala Leu Gly
        195                 200                 205

Gly Val Arg Pro Ser Ala Cys Leu Pro Val Thr Ile Asp Val Gly Thr
    210                 215                 220

Asn Asn Glu Lys Leu Leu Asn Asp Glu Phe Tyr Ile Gly Leu Arg Gln
225                 230                 235                 240

Lys Arg Ala Thr Gly Gln Glu Tyr Ser Glu Leu Leu Asn Glu Phe Met
                245                 250                 255

Ser Ala Val Lys Gln Asn Tyr Gly Glu Lys Val Leu Ile Gln Phe Glu
            260                 265                 270

Asp Phe Ala Asn His Asn Ala Phe Glu Leu Leu Ala Lys Tyr Ser Asp
        275                 280                 285
```

```
Thr His Leu Val Phe Asn Asp Asp Ile Gln Gly Thr Ala Ser Val Val
    290                 295                 300
Leu Ala Gly Leu Val Ser Ala Gln Lys Leu Thr Asn Ser Pro Leu Ala
305                 310                 315                 320
Glu His Thr Phe Leu Phe Leu Gly Ala Gly Glu Ala Gly Thr Gly Ile
                325                 330                 335
Ala Glu Leu Ile Ala Leu Tyr Met Ser Lys Gln Met Asn Ala Ser Val
                340                 345                 350
Glu Glu Ser Arg Lys Lys Ile Trp Leu Val Asp Ser Lys Gly Leu Ile
                355                 360                 365
Val Asn Ser Arg Lys Asp Ser Leu Gln Asp Phe Lys Lys Pro Trp Ala
    370                 375                 380
His Glu His Glu Pro Val Lys Asp Leu Leu Gly Ala Ile Lys Ala Ile
385                 390                 395                 400
Lys Pro Thr Val Leu Ile Gly Ser Ser Val Gly Arg Ser Phe Thr
                405                 410                 415
Lys Glu Val Ile Glu Ala Met Ser Ser Ile Asn Glu Arg Pro Leu Ile
                420                 425                 430
Met Ala Leu Ser Asn Pro Thr Thr Gln Ser Glu Cys Thr Ala Glu Glu
                435                 440                 445
Ala Tyr Thr Trp Ser Lys Gly Arg Ala Ile Phe Ala Ser Gly Ser Pro
    450                 455                 460
Phe Asp Pro Val Glu Tyr Glu Gly Lys Val Phe Val Ser Thr Gln Ala
465                 470                 475                 480
Asn Asn Ala Tyr Ile Phe Pro Gly Phe Gly Leu Gly Leu Val Ile Ser
                485                 490                 495
Gly Ala Ile Arg Val His Asp Asp Met Leu Leu Ala Ala Ala Glu Ala
                500                 505                 510
Leu Ala Gly Gln Val Ser Lys Glu Asn Tyr Glu Lys Gly Met Ile Tyr
                515                 520                 525
Pro Ser Phe Ser Ser Ile Arg Lys Ile Ser Ala Gln Ile Ala Ala Asn
    530                 535                 540
Val Ala Thr Lys Ala Tyr Glu Leu Gly Leu Ala Gly Arg Leu Pro Arg
545                 550                 555                 560
Pro Lys Asp Ile Val Lys Cys Ala Glu Ser Ser Met Tyr Ser Pro Thr
                565                 570                 575
Tyr Arg Leu Tyr Arg
            580

<210> SEQ ID NO 19
<211> LENGTH: 1347
<212> TYPE: DNA
<213> ORGANISM: Arabidopsis thaliana

<400> SEQUENCE: 19
atggcgtcag acaaacaaaa ggcggagaga gccgaggttg cggcgaggct agcggctgag      60
gacttgcatg acattaacaa atccggtggt gctgatgtca caatgtataa ggtgacggag     120
agaacaactg aacatccacc ggagcaagat aggcccggtg tgataggttc agtgttcagg     180
gctgtccaag gaacgtatga gcatgcgaga gacgctgtag ttggaaaaac ccacgaagcg     240
gctgagtcta ccaagaagg agctcagata gcttcagaga aagcggttgg agcaaaggac     300
gcaaccgtcg agaagctaa ggaaccgct gattatactg cggagaaggt gggtgagtat      360
aaagactata cggttgataa agctaaagag gctaaggaca caactgcaga gaaggcgaag     420
```

```
gagactgcta attatactgc ggataaggcg gtggaagcaa aggataagac ggcggagaag    480
attggtgagt acaaagacta tgcggtggat aaggcagtag aagctaaaga taagacagcg    540
gagaaggcga aggagacttc gaattatacg gcggataagg ctaaagaggc taaggacaag    600
acggctgaga aggttggtga gtataaggat tacacggtgg acaaggccgt ggaagctagg    660
gattacacag cggagaaggc tattgaagca aaggataaga cagctgagaa gactggagag    720
tataaggact atacggtgga gaaggcgacg gaggggaaaa tgttacggt gagtaagcta    780 ggagagctga aggatagtgc cgttgagaca gcgaagagag ctatgggttt cttgtcgggg    840
aagacagagg aggccaaagg aaaagctgtg gagaccaaag atactgccaa ggaaaacatg    900
gagaaagctg agaagtaac aagacaaaag atggaggaaa tgagattgga aggtaaagag    960
ctcaaagaag aagctggagc aaaagcccaa gaggcatctc aaaagactag ggagagtact   1020
gagtcgggag ctcaaaaagc cgaagagacc aaagattctc ctgccgtgag gggaaatgaa   1080
gcgaaaggga ctattttttgg tgcattaggg aatgtaacgg aagcaataaa gagcaaactg   1140
acaatgccat cagacattgt ggaggaaaca cgcgcggcac gtgagcatgg agggacgggt   1200
aggactgtgg ttgaagtcaa ggtcgaggat tcaaagccgg gtaaggtggc gacttcactg   1260
aaggcgtcgg atcaaatgac cggtcaaaca ttcaacgacg ttggacggat ggatgatgat   1320
gctcggaaag ataagggaaa gctgtga                                      1347

<210> SEQ ID NO 20
<211> LENGTH: 448
<212> TYPE: PRT
<213> ORGANISM: Arabidopsis thaliana

<400> SEQUENCE: 20

Met Ala Ser Asp Lys Gln Lys Ala Glu Arg Ala Glu Val Ala Ala Arg
 1               5                  10                  15

Leu Ala Ala Glu Asp Leu His Asp Ile Asn Lys Ser Gly Gly Ala Asp
             20                  25                  30

Val Thr Met Tyr Lys Val Thr Glu Arg Thr Thr Glu His Pro Pro Glu
         35                  40                  45

Gln Asp Arg Pro Gly Val Ile Gly Ser Val Phe Arg Ala Val Gln Gly
     50                  55                  60

Thr Tyr Glu His Ala Arg Asp Ala Val Val Gly Lys Thr His Glu Ala
 65                  70                  75                  80

Ala Glu Ser Thr Lys Glu Gly Ala Gln Ile Ala Ser Glu Lys Ala Val
                 85                  90                  95

Gly Ala Lys Asp Ala Thr Val Glu Lys Ala Lys Glu Thr Ala Asp Tyr
            100                 105                 110

Thr Ala Glu Lys Val Gly Glu Tyr Lys Asp Tyr Thr Val Asp Lys Ala
        115                 120                 125

Lys Glu Ala Lys Asp Thr Thr Ala Glu Lys Ala Lys Glu Thr Ala Asn
    130                 135                 140

Tyr Thr Ala Asp Lys Ala Val Glu Ala Lys Asp Lys Thr Ala Glu Lys
145                 150                 155                 160

Ile Gly Glu Tyr Lys Asp Tyr Ala Val Asp Ala Val Glu Ala Lys
                165                 170                 175

Asp Lys Thr Ala Glu Lys Ala Lys Glu Thr Ser Asn Tyr Thr Ala Asp
            180                 185                 190

Lys Ala Lys Glu Ala Lys Asp Lys Thr Ala Glu Lys Val Gly Glu Tyr
        195                 200                 205
```

```
Lys Asp Tyr Thr Val Asp Lys Ala Val Glu Ala Arg Asp Tyr Thr Ala
            210                 215                 220
Glu Lys Ala Ile Glu Ala Lys Asp Lys Thr Ala Glu Lys Thr Gly Glu
225                 230                 235                 240
Tyr Lys Asp Tyr Thr Val Glu Lys Ala Thr Glu Gly Lys Asp Val Thr
                245                 250                 255
Val Ser Lys Leu Gly Glu Leu Lys Asp Ser Ala Val Glu Thr Ala Lys
            260                 265                 270
Arg Ala Met Gly Phe Leu Ser Gly Lys Thr Glu Glu Ala Lys Gly Lys
        275                 280                 285
Ala Val Glu Thr Lys Asp Thr Ala Lys Glu Asn Met Glu Lys Ala Gly
    290                 295                 300
Glu Val Thr Arg Gln Lys Met Glu Glu Met Arg Leu Glu Gly Lys Glu
305                 310                 315                 320
Leu Lys Glu Glu Ala Gly Ala Lys Ala Gln Glu Ala Ser Gln Lys Thr
                325                 330                 335
Arg Glu Ser Thr Glu Ser Gly Ala Gln Lys Ala Glu Thr Lys Asp
            340                 345                 350
Ser Pro Ala Val Arg Gly Asn Glu Ala Lys Gly Thr Ile Phe Gly Ala
        355                 360                 365
Leu Gly Asn Val Thr Glu Ala Ile Lys Ser Lys Leu Thr Met Pro Ser
    370                 375                 380
Asp Ile Val Glu Glu Thr Arg Ala Ala Arg Glu His Gly Gly Thr Gly
385                 390                 395                 400
Arg Thr Val Val Glu Val Lys Val Glu Asp Ser Lys Pro Gly Lys Val
                405                 410                 415
Ala Thr Ser Leu Lys Ala Ser Asp Gln Met Thr Gly Gln Thr Phe Asn
            420                 425                 430
Asp Val Gly Arg Met Asp Asp Asp Ala Arg Lys Asp Lys Gly Lys Leu
        435                 440                 445

<210> SEQ ID NO 21
<211> LENGTH: 564
<212> TYPE: DNA
<213> ORGANISM: Arabidopsis thaliana

<400> SEQUENCE: 21
atgctctctg acgccggggg tggttccgat tgccggcgtc gggacttatc aactcccatc      60
aaccttcatg tgttctatat aagctttatc ttcattgaat cttcctccgt tatctcaaat     120
ctctcaaaat atctaaatct ccttttttat gtgagcttct tcactgaaag ttttctttgt     180
gacggaagag tatatcgatg ctctattggc tccgatctga ctcagatctt ggatgcatct     240
ctgtcttcga acccaaaaca agaaaattca caacagtcca acagctcctc ttctcaaaca     300
tcagagcaag acttcatcaa cttatcaaaa agctctagat ctggactagc accaacacca     360
cctttggttt cttctcaccg gttttcgttg atggcaggag tatctcttgg accatcagat     420
gtgcttcttc cgctgggaac gtcgacggca cacgacgagc tcaaacgctg caatggtca      480 ccctatatga ttcacagtcg cccatcattc caattcttca gaatgacgga ggcgctttcc     540
ttatcccgac aacatcaacc ctag                                            564

<210> SEQ ID NO 22
<211> LENGTH: 187
<212> TYPE: PRT
<213> ORGANISM: Arabidopsis thaliana
```

<400> SEQUENCE: 22

```
Met Leu Ser Asp Ala Gly Gly Ser Asp Cys Arg Arg Asp Leu
 1               5                  10                  15
Ser Thr Pro Ile Asn Leu His Val Phe Tyr Ile Ser Phe Ile Phe Ile
            20                  25                  30
Glu Ser Ser Val Ile Ser Asn Leu Ser Lys Tyr Leu Asn Leu Leu
        35                  40                  45
Phe Tyr Val Ser Phe Phe Thr Glu Ser Phe Leu Cys Asp Gly Arg Val
    50                  55                  60
Tyr Arg Cys Ser Ile Gly Ser Asp Leu Thr Gln Ile Leu Asp Ala Ser
 65                  70                  75                  80
Leu Ser Ser Asn Pro Lys Gln Glu Asn Ser Gln Gln Ser Asn Ser Ser
                85                  90                  95
Ser Ser Gln Thr Ser Glu Gln Asp Phe Ile Asn Leu Ser Lys Ser Ser
            100                 105                 110
Arg Ser Gly Leu Ala Pro Thr Pro Pro Leu Val Ser Ser His Arg Phe
        115                 120                 125
Ser Leu Met Ala Gly Val Ser Leu Gly Pro Ser Asp Val Leu Leu Pro
    130                 135                 140
Leu Gly Thr Ser Thr Ala His Asp Glu Leu Lys Arg Trp Gln Trp Ser
145                 150                 155                 160
Pro Tyr Met Ile His Ser Arg Pro Ser Phe Gln Phe Phe Arg Met Thr
                165                 170                 175
Glu Ala Leu Ser Leu Ser Arg Gln His Gln Pro
            180                 185
```

<210> SEQ ID NO 23
<211> LENGTH: 753
<212> TYPE: DNA
<213> ORGANISM: Arabidopsis thaliana

<400> SEQUENCE: 23

```
atggaaggtg gagctgctct ctacaatcct cgaactgtcg aagaagtttt caaggatttc    60
aaaggtcgtc gtactgccat tgtcaaagct ctcaccaccg atgttcaaga gttttaccaa   120
caatgtgacc ctgagaagga gaatctttgc ttgtatgggt taccgaatga agaatgggaa   180
gtgaatttac cagctgaaga agtgcctcct gagttaccag agccagctct tggtattaac   240
tttgctaggg atgggctctc tgaaaaggaa tggctttcgc ttgttgctat tcacagtgac   300
gcttggttac tgtctgtctc gttttacttt ggctcaaggt tttctttcca caaggaagag   360
aggaagcgtt tgttcaacat gatcaatgat gttcctacta tatttgaagt agtgactgga   420
atggctaaag caaggacaa gtcatctgct gcaaatcaaa acggaaacaa atccaagtct   480
aactctaaag ttagaacttc agggggaaaa agctcaaaga ccaagcagcc aaaagaggag   540
gacgaagaaa tagatgaaga tgatgaggat gaccacgggg aaacccttg tggagcctgt   600
ggagacagtg atggtgctga tgaattctgg atctgctgtg acctttgtga aagtggttc    660
catggcaagt gtgtgaagat cactccagct agagctgagc atatcaaaca atacaagtgc   720
ccttcatgca gcaacaaaag agctcgagct taa                               753
```

<210> SEQ ID NO 24
<211> LENGTH: 250
<212> TYPE: PRT
<213> ORGANISM: Arabidopsis thaliana

<400> SEQUENCE: 24

Met Glu Gly Gly Ala Ala Leu Tyr Asn Pro Arg Thr Val Glu Val
1               5                   10                  15

Phe Lys Asp Phe Lys Gly Arg Arg Thr Ala Ile Val Lys Ala Leu Thr
            20                  25                  30

Thr Asp Val Gln Glu Phe Tyr Gln Gln Cys Asp Pro Glu Lys Glu Asn
        35                  40                  45

Leu Cys Leu Tyr Gly Leu Pro Asn Glu Glu Trp Glu Val Asn Leu Pro
    50                  55                  60

Ala Glu Glu Val Pro Pro Glu Leu Pro Glu Pro Ala Leu Gly Ile Asn
65              70                  75                  80

Phe Ala Arg Asp Gly Leu Ser Glu Lys Glu Trp Leu Ser Leu Val Ala
                85                  90                  95

Ile His Ser Asp Ala Trp Leu Leu Ser Val Ser Phe Tyr Phe Gly Ser
                100                 105                 110

Arg Phe Ser Phe His Lys Glu Glu Arg Lys Arg Leu Phe Asn Met Ile
            115                 120                 125

Asn Asp Val Pro Thr Ile Phe Glu Val Val Thr Gly Met Ala Lys Ala
    130                 135                 140

Lys Asp Lys Ser Ser Ala Ala Asn Gln Asn Gly Asn Lys Ser Lys Ser
145                 150                 155                 160

Asn Ser Lys Val Arg Thr Ser Gly Gly Lys Ser Ser Lys Thr Lys Gln
                165                 170                 175

Pro Lys Glu Glu Asp Glu Glu Ile Asp Glu Asp Glu Asp His
            180                 185                 190

Gly Glu Thr Leu Cys Gly Ala Cys Gly Asp Ser Asp Gly Ala Asp Glu
            195                 200                 205

Phe Trp Ile Cys Cys Asp Leu Cys Glu Lys Trp Phe His Gly Lys Cys
    210                 215                 220

Val Lys Ile Thr Pro Ala Arg Ala Glu His Ile Lys Gln Tyr Lys Cys
225                 230                 235                 240

Pro Ser Cys Ser Asn Lys Arg Ala Arg Ala
                245                 250

<210> SEQ ID NO 25
<211> LENGTH: 1218
<212> TYPE: DNA
<213> ORGANISM: Arabidopsis thaliana

<400> SEQUENCE: 25 atgggtcat cacagtcttc gcaattactc gatgaagaag aagaagaaga agatgaagca    60
gagagcgaag gtgaagaagt agaagaagaa gaagatgaag cagagagcga attgaataac    120
agaagaatcg agctggataa tctcttggtc aagaaagttc tcgagcaaga gcctgagatg    180
cttccttgtc acgcctctgc ttctccactc tctcctcagc tctcttctct tggaactcct    240
cgaatcggac cttccattaa agtctgggat ccttacaacg tcctcgcgcc acctcctcct    300
tcttctccgc ctcttttctc tcgtatctcc tccgccgcgg aacacgatcg ctccgccgtg    360
acggaagtct atttcatcag ccacggcgag tgtgatctca atctcaggcc tgatctgatt    420
ggaggtagat gccacgtggc tactctcaca cccaacggga acgtcaggc gagagctcta    480 gccgtatttt taaactctga aggtgttcga ttcacctccg tcttctcttc gcctctggat    540
cgagctagat ccatggctgt ttctgtttgc caggaaatga atttcctga ggagcatttg    600 caagtctcgg atgctgtggt tgagatgagt ttaggggact gggaaagctg tcatcggtca    660

```
gagatttaca cacctgaaac tctaagttta atagaaagat gccaacctga tttctcagct    720
ccatctggtg aatcactcag acaagtagag tttcggatgg ttcagtttct gaatgggaca    780
gtctcaggac tttcggagaa gctcaggtca gaacttcttc catctacaca gcacacaaat    840
tccagagggt tctcgttagc tacttctatt catcgcccaa ttcttacaag gaagaaatct    900
gggaagagcc ggtttcaggt gatgaatgca actggtgatc acgagggtag tgaagagata    960
tttagtaatc acaatgatga acaacaccta ggtgatataa acatcaagag ttcttcttct   1020
caactctcaa cctgcattgg agttttcact cactctttac ctataaagtg tcttcttacc   1080
ggtatccttg gatgcagccc ggtaatgaca cataagatct gtgtggagga ttcctctgtg   1140
accgtattac agcattcgtg gaaaaccggg tggcaggtaa agcggttaaa tgacaccgct   1200
catcttagac tgttgtag                                                 1218
```

<210> SEQ ID NO 26
<211> LENGTH: 405
<212> TYPE: PRT
<213> ORGANISM: Arabidopsis thaliana

<400> SEQUENCE: 26

```
Met Gly Ser Ser Gln Ser Ser Gln Leu Leu Asp Glu Glu Glu Glu
1               5                   10                  15

Glu Asp Glu Ala Glu Ser Glu Gly Glu Glu Val Glu Glu Glu Asp
            20                  25                  30

Glu Ala Glu Ser Glu Leu Asn Asn Arg Arg Ile Glu Leu Asp Asn Leu
        35                  40                  45

Leu Val Lys Lys Val Leu Glu Gln Glu Pro Glu Met Leu Pro Cys His
    50                  55                  60

Ala Ser Ala Ser Pro Leu Ser Pro Gln Leu Ser Ser Leu Gly Thr Pro
65                  70                  75                  80

Arg Ile Gly Pro Ser Ile Lys Val Trp Asp Pro Tyr Asn Val Leu Ala
                85                  90                  95

Pro Pro Pro Pro Ser Ser Pro Pro Leu Phe Ser Arg Ile Ser Ser Ala
            100                 105                 110

Ala Glu His Asp Arg Ser Ala Val Thr Glu Val Tyr Phe Ile Ser His
        115                 120                 125

Gly Glu Cys Asp Leu Asn Leu Arg Pro Asp Leu Ile Gly Gly Arg Cys
    130                 135                 140

His Val Ala Thr Leu Thr Pro Asn Gly Lys Arg Gln Ala Arg Ala Leu
145                 150                 155                 160

Ala Val Phe Leu Asn Ser Glu Gly Val Arg Phe Thr Ser Val Phe Ser
                165                 170                 175

Ser Pro Leu Asp Arg Ala Arg Ser Met Ala Val Ser Val Cys Gln Glu
            180                 185                 190

Met Asn Phe Pro Glu Glu His Leu Gln Val Ser Asp Ala Val Val Glu
        195                 200                 205

Met Ser Leu Gly Asp Trp Glu Ser Cys His Arg Ser Glu Ile Tyr Thr
    210                 215                 220

Pro Glu Thr Leu Ser Leu Ile Glu Arg Cys Gln Pro Asp Phe Ser Ala
225                 230                 235                 240

Pro Ser Gly Glu Ser Leu Arg Gln Val Glu Phe Arg Met Val Gln Phe
                245                 250                 255

Leu Asn Gly Thr Val Ser Gly Leu Ser Glu Lys Leu Arg Ser Glu Leu
            260                 265                 270
```

Leu Pro Ser Thr Gln His Thr Asn Ser Arg Gly Phe Ser Leu Ala Thr
            275                 280                 285

Ser Ile His Arg Pro Ile Leu Thr Arg Lys Lys Ser Gly Lys Ser Arg
        290                 295                 300

Phe Gln Val Met Asn Ala Thr Gly Asp His Glu Gly Ser Glu Glu Ile
305                 310                 315                 320

Phe Ser Asn His Asn Asp Glu Gln His Leu Gly Asp Ile Asn Ile Lys
                325                 330                 335

Ser Ser Ser Ser Gln Leu Ser Thr Cys Ile Gly Val Phe Thr His Ser
                340                 345                 350

Leu Pro Ile Lys Cys Leu Leu Thr Gly Ile Leu Gly Cys Ser Pro Val
            355                 360                 365

Met Thr His Lys Ile Cys Val Glu Asp Ser Ser Val Thr Val Leu Gln
        370                 375                 380

His Ser Trp Lys Thr Gly Trp Gln Val Lys Arg Leu Asn Asp Thr Ala
385                 390                 395                 400

His Leu Arg Leu Leu
            405

<210> SEQ ID NO 27
<211> LENGTH: 420
<212> TYPE: DNA
<213> ORGANISM: Arabidopsis thaliana

<400> SEQUENCE: 27
atgctagatc acagtgaaaa ggtcttattg gttgattcag aaaccatgaa aacaagagct      60
gaagatatga tcgaacagaa caacactagt gttaacgaca agaagaagac ttgtgctgat     120
tgtggaacca gtaaaactcc tctttggcgt ggtggtcctg ttggtccaaa gtcgttgtgt     180
aacgcgtgtg ggatcagaaa cagaaagaag agaagaggag aacagaagga taataagaaa     240
ttaaagaaat cgagttctgg cggcggaaac cgtaaatttg gtgaatcgtt aaaacagagt     300
ttgatggatt tggggataag gaagagatca acggtggaga agcaacgaca gaagcttggt     360
gaagaagaac aagccgctgt gttactcatg gctctttctt atggctctgt ttacgcttag     420

<210> SEQ ID NO 28
<211> LENGTH: 139
<212> TYPE: PRT
<213> ORGANISM: Arabidopsis thaliana

<400> SEQUENCE: 28

Met Leu Asp His Ser Glu Lys Val Leu Leu Val Asp Ser Glu Thr Met
1               5                   10                  15

Lys Thr Arg Ala Glu Asp Met Ile Glu Gln Asn Asn Thr Ser Val Asn
            20                  25                  30

Asp Lys Lys Lys Thr Cys Ala Asp Cys Gly Thr Ser Lys Thr Pro Leu
        35                  40                  45

Trp Arg Gly Gly Pro Val Gly Pro Lys Ser Leu Cys Asn Ala Cys Gly
    50                  55                  60

Ile Arg Asn Arg Lys Lys Arg Arg Gly Gly Thr Glu Asp Asn Lys Lys
65                  70                  75                  80

Leu Lys Lys Ser Ser Ser Gly Gly Gly Asn Arg Lys Phe Gly Glu Ser
                85                  90                  95

Leu Lys Gln Ser Leu Met Asp Leu Gly Ile Arg Lys Arg Ser Thr Val
            100                 105                 110

Glu Lys Gln Arg Gln Lys Leu Gly Glu Glu Gln Ala Ala Val Leu
            115                 120                 125

Leu Met Ala Leu Ser Tyr Gly Ser Val Tyr Ala
    130                 135

<210> SEQ ID NO 29
<211> LENGTH: 522
<212> TYPE: DNA
<213> ORGANISM: Arabidopsis thaliana

<400> SEQUENCE: 29

```
atggcaacac actcttcctt caccgcaaca acacctctct ttctcatcgt tcttctatcc    60
ctatcctccg tctcagttct cggcgcatct caccaccacg caacggcgcc ggctccgtct   120
gtagactgtt cgactctcat actcaacatg gctgactgtt tatccttcgt ttcgagcgga   180
ggcacggtgg cgaaaccgga aggtacatgt tgctctggtc ttaagacggt gcttaaagct   240
gactctcagt gtctatgtga agcgtttaag agcagtgctt ctcttggagt tactttgaat   300
atcactaagg cttctactct tcccgccgca tgcaagcttc acgctccttc tatcgctact   360
tgtggatgtc ttgctccagg agtagctgct gctggacctg agacagccgg atttctagct   420
ccaaatcctt cttcagggaa cgatggatct tctttgattc cgacctcgtt cacaactgta   480
ctcagtgccg tactgttcgt tttgttcttc tctagtgcgt aa                      522
```

<210> SEQ ID NO 30
<211> LENGTH: 182
<212> TYPE: PRT
<213> ORGANISM: Arabidopsis thaliana

<400> SEQUENCE: 30

Met Ala Thr His Ser Ser Phe Thr Ala Thr Thr Pro Leu Phe Leu Ile
  1               5                  10                  15

Val Leu Leu Ser Leu Ser Ser Val Ser Val Leu Gly Ala Ser His His
             20                  25                  30

His Ala Thr Ala Pro Ala Pro Ser Val Asp Cys Ser Thr Leu Ile Leu
         35                  40                  45

Asn Met Ala Asp Cys Leu Ser Phe Val Ser Ser Gly Gly Thr Val Ala
     50                  55                  60

Lys Pro Glu Gly Thr Cys Cys Ser Gly Leu Lys Thr Val Leu Lys Ala
 65                  70                  75                  80

Asp Ser Gln Cys Leu Cys Glu Ala Phe Lys Ser Ser Ala Ser Leu Gly
                 85                  90                  95

Val Thr Leu Asn Ile Thr Lys Ala Ser Thr Leu Pro Ala Ala Cys Lys
            100                 105                 110

Leu His Ala Pro Ser Ile Ala Thr Cys Gly Leu Ser Val Ala Pro Ser
            115                 120                 125

Thr Ala Pro Gly Leu Ala Pro Gly Val Ala Ala Gly Pro Glu Thr
        130                 135                 140

Ala Gly Phe Leu Ala Pro Asn Pro Ser Ser Gly Asn Asp Gly Ser Ser
145                 150                 155                 160

Leu Ile Pro Thr Ser Phe Thr Thr Val Leu Ser Ala Val Leu Phe Val
                165                 170                 175

Leu Phe Phe Ser Ser Ala
            180

<210> SEQ ID NO 31
<211> LENGTH: 987

<212> TYPE: DNA
<213> ORGANISM: Arabidopsis thaliana

<400> SEQUENCE: 31

```
atggaccctt tagcttccca acatcaacac aaccatctgg aagataataa ccaaaccta      60
acccataata atcctcaatc cgattccacc accgactcat caacttcctc cgctcaacgc     120
aaacgcaaag gcaaaggtgg tccggacaac tccaagttcc gttaccgtgg cgttcgacaa     180
agaagctggg gcaaatgggt cgccgagatc cgagagccac gtaagcgcac tgcaagtgg      240
cttggtactt tcgcaaccgc cgaagacgcc gcacgtgcct acgaccgggc tgccgtttac     300
ctatacgggt cacgtgctca gctcaactta accccttcgt ctccttcctc cgtctcttcc     360
tcttcctcct ccgtctccgc cgcttcttct ccttccacct cctcttcctc cactcaaacc     420
ctaagacctc tcctccctcg ccccgccgcc gccaccgtag gaggaggagc aactttggt      480
ccgtacggta tcccttttaa caacaacatc ttccttaatg gtgggacctc tatgttatgc     540
cctagttatg gttttttccc tcaacaacaa caacaacaaa atcagatggt ccagatggga     600
caattccaac accaacagta tcagaatctt cattctaata ctaacaataa caagatttct     660
gacatcgagc tcactgatgt tccggtaact aattcgactt cgtttcatca tgaggtggcg     720
ttagggcagg aacaaggagg aagtgggtgt aataataata gttcgatgga ggatttgaac     780
tctctagctg gttcggtggg ttcgagtcta tcaataactc atccaccgcc gttggttgat     840
ccggtatgtt ctatgggtct ggatccgggt tatatggttg agatggatc ttcgaccatt      900
tggccttttg gaggagaaga agaatatagt cataattggg ggagtatttg ggattttatt     960
gatcccatct tgggggaatt ctattaa                                        987
```

<210> SEQ ID NO 32
<211> LENGTH: 328
<212> TYPE: PRT
<213> ORGANISM: Arabidopsis thaliana

<400> SEQUENCE: 32

```
Met Asp Pro Leu Ala Ser Gln His Gln His Asn His Leu Glu Asp Asn
  1               5                  10                  15

Asn Gln Thr Leu Thr His Asn Asn Pro Gln Ser Asp Ser Thr Thr Asp
             20                  25                  30

Ser Ser Thr Ser Ser Ala Gln Arg Lys Arg Lys Gly Lys Gly Gly Pro
         35                  40                  45

Asp Asn Ser Lys Phe Arg Tyr Arg Gly Val Arg Gln Arg Ser Trp Gly
     50                  55                  60

Lys Trp Val Ala Glu Ile Arg Glu Pro Arg Lys Arg Thr Arg Lys Trp
 65                  70                  75                  80

Leu Gly Thr Phe Ala Thr Ala Glu Asp Ala Ala Arg Ala Tyr Asp Arg
                 85                  90                  95

Ala Ala Val Tyr Leu Tyr Gly Ser Arg Ala Gln Leu Asn Leu Thr Pro
            100                 105                 110

Ser Ser Pro Ser Ser Val Ser Ser Ser Ser Val Ser Ala Ala
        115                 120                 125

Ser Ser Pro Ser Thr Ser Ser Ser Thr Gln Thr Leu Arg Pro Leu
    130                 135                 140

Leu Pro Arg Pro Ala Ala Thr Val Gly Gly Ala Asn Phe Gly
145                 150                 155                 160

Pro Tyr Gly Ile Pro Phe Asn Asn Asn Ile Phe Leu Asn Gly Gly Thr
                165                 170                 175
```

```
Ser Met Leu Cys Pro Ser Tyr Gly Phe Phe Pro Gln Gln Gln Gln
            180                 185                 190

Gln Asn Gln Met Val Gln Met Gly Gln Phe Gln His Gln Gln Tyr Gln
        195                 200                 205

Asn Leu His Ser Asn Thr Asn Asn Lys Ile Ser Asp Ile Glu Leu
    210                 215                 220

Thr Asp Val Pro Val Thr Asn Ser Thr Ser Phe His His Glu Val Ala
225                 230                 235                 240

Leu Gly Gln Glu Gln Gly Gly Ser Gly Cys Asn Asn Ser Ser Met
            245                 250                 255

Glu Asp Leu Asn Ser Leu Ala Gly Ser Val Gly Ser Ser Leu Ser Ile
            260                 265                 270

Thr His Pro Pro Pro Leu Val Asp Pro Val Cys Ser Met Gly Leu Asp
        275                 280                 285

Pro Gly Tyr Met Val Gly Asp Gly Ser Ser Thr Ile Trp Pro Phe Gly
        290                 295                 300

Gly Glu Glu Glu Tyr Ser His Asn Trp Gly Ser Ile Trp Asp Phe Ile
305                 310                 315                 320

Asp Pro Ile Leu Gly Glu Phe Tyr
                325

<210> SEQ ID NO 33
<211> LENGTH: 2322
<212> TYPE: DNA
<213> ORGANISM: Arabidopsis thaliana

<400> SEQUENCE: 33
atggttaaag aaatagcttc ttggttattg atactatcaa tggtggtgtt tgtttctccg      60
gttttagcta taaacggcgg tggttatcca cgatgtaact gcgaagacga aggaaacagt     120
ttctggagta cagagaacat tctagaaact caaagagtaa gcgatttctt aatcgcagta     180
gcttatttct caatccctat tgagttactt tacttcgtga gttgttccaa tgttccattc     240
aaatgggttc tctttgagtt tatcgccttc attgttcttt gtggtatgac tcatcttctt     300
catggttgga cttactctgc tcatccattt agattaatga tggcgtttac tgttttcaag     360
atgttgactg ctttagtctc ttgtgctact gcgattacgc ttattacttt gattcctctg     420
cttttgaaag ttaagttag agagtttatg cttaagaaga agctcatga gcttggtcgt     480
gaagttggtt tgattttgat taagaaagag actggctttc atgttcgtat gcttactcaa     540
gagattcgta gtctttgga tcgtcatacg attctttata ctactttggt tgagctttcg     600
aagactttag ggttgcagaa ttttgcggtt tggatgccga tgacggtgg aacggagatg     660
gatttgactc atgagttgag agggagaggt ggttatggtg ttgttctgt ttctatggag     720
gatttggatg ttgttaggat tagggagagt gatgaagtga atgtgttgag tgttgactcg     780
tccattgctc gagctagtgg tggtggtggg gatgttagtg agattggtgc cgtggctgct     840
attagaatgc cgatgcttcg tgtttcggat tttaatggag agctaagtta tgcgatactt     900
gtttgtgttt taccgggcgg gacgcctcgg gattggactt atcaggagat tgagattgtt     960
aaagttgtgg cggatcaagt aaccgttgcg ttagatcatg cagcggttct tgaagagtct    1020
cagcttatga gggagaagct ggcggaacag aacagggcgt tgcagatggc gaagagagac    1080
gcgttgagag cgagccaagc gaggaatgcg tttcagaaaa cgatgagcga agggatgagg    1140
cgtcctatgc attcgatact cggtcttttg tcgatgattc aggacgagaa gttgagtgac    1200
```

```
gagcagaaaa tgattgttga tacgatggtt aaaacaggga atgttatgtc gaatttggtg    1260 gggactcta tggatgtgcc tgacggtaga tttggtacgg agatgaaacc atttagtctg    1320
catcgtacga tccatgaagc agcttgtatg gcgagatgtt tgtgtctatg caatggaatt    1380
aggttcttgg ttgacgcgga gaagtctcta cctgataatg tagtaggtga tgaaagaagg    1440
gtctttcaag tgatacttca tatagttggt agtttagtaa agcctagaaa acgtcaagaa    1500
ggatcttcat tgatgtttaa ggttttgaaa gaaagaggaa gcttggatag gagtgatcat    1560
agatgggctg cttggagatc accggcttct tcagcagatg gagatgtgta tataagattt    1620
gaaatgaatg tagagaatga tgattcaagt tctcaatcat ttgcttctgt ttcctccaga    1680
gatcaagaag ttggtgatgt tagattctcc ggcggctatg ggttaggaca agatctaagc    1740
tttggtgttt gtaagaaagt ggtgcagttg attcatggga atatctcggt ggtccctggc    1800
tcggatggtt caccggagac catgtcgttg ctccctcggt ttcgacgtag accctccata    1860
tctgtccatg gatccagcga gtcgccagcc cctgaccacc acgctcaccc acattcgaat    1920
tctctgttac gtggcttaca agtttattg gtagacacca acgattcgaa ccgggcagtt    1980
acacgtaaac tcttagagaa actcgggtgc gatgtaaccg cggtttcctc tggattcgat    2040
tgccttaccg ccattgctcc cggctcgtcc tcgccttcta cttcgtttca gtggtggtg    2100 cttgatcttc aaatggcaga gatggacggt tatgaagtgg ccatgaggat caggagtcga    2160
tcttggccgt tgattgtggc gacgacagtg ggcttggatg aagaaatgtg ggacaagtgt    2220
gcacagattg gaatcaatgg agttgtgaga aagccagtgg tgttaagagc tatggagagt    2280
gagctccgaa gagtattgtt gcaagctgac caacttctct aa                      2322
```

<210> SEQ ID NO 34
<211> LENGTH: 773
<212> TYPE: PRT
<213> ORGANISM: Arabidopsis thaliana

<400> SEQUENCE: 34

```
Met Val Lys Glu Ile Ala Ser Trp Leu Leu Ile Leu Ser Met Val Val
  1               5                  10                  15

Phe Val Ser Pro Val Leu Ala Ile Asn Gly Gly Gly Tyr Pro Arg Cys
             20                  25                  30

Asn Cys Glu Asp Glu Gly Asn Ser Phe Trp Ser Thr Glu Asn Ile Leu
         35                  40                  45

Glu Thr Gln Arg Val Ser Asp Phe Leu Ile Ala Val Ala Tyr Phe Ser
     50                  55                  60

Ile Pro Ile Glu Leu Leu Tyr Phe Val Ser Cys Ser Asn Val Pro Phe
 65                  70                  75                  80

Lys Trp Val Leu Phe Glu Phe Ile Ala Phe Ile Val Leu Cys Gly Met
                 85                  90                  95

Thr His Leu Leu His Gly Trp Thr Tyr Ser Ala His Pro Phe Arg Leu
            100                 105                 110

Met Met Ala Phe Thr Val Phe Lys Met Leu Thr Ala Leu Val Ser Cys
        115                 120                 125

Ala Thr Ala Ile Thr Leu Ile Thr Leu Ile Pro Leu Leu Leu Lys Val
    130                 135                 140

Lys Val Arg Glu Phe Met Leu Lys Lys Ala His Glu Leu Gly Arg
145                 150                 155                 160

Glu Val Gly Leu Ile Leu Ile Lys Lys Glu Thr Gly Phe His Val Arg
                165                 170                 175
```

-continued

```
Met Leu Thr Gln Glu Ile Arg Lys Ser Leu Asp Arg His Thr Ile Leu
                180                 185                 190

Tyr Thr Thr Leu Val Glu Leu Ser Lys Thr Leu Gly Leu Gln Asn Phe
            195                 200                 205

Ala Val Trp Met Pro Asn Asp Gly Gly Thr Glu Met Asp Leu Thr His
        210                 215                 220

Glu Leu Arg Gly Arg Gly Gly Tyr Gly Gly Cys Ser Val Ser Met Glu
225                 230                 235                 240

Asp Leu Asp Val Val Arg Ile Arg Glu Ser Asp Glu Val Asn Val Leu
                245                 250                 255

Ser Val Asp Ser Ser Ile Ala Arg Ala Ser Gly Gly Gly Gly Asp Val
            260                 265                 270

Ser Glu Ile Gly Ala Val Ala Ala Ile Arg Met Pro Met Leu Arg Val
        275                 280                 285

Ser Asp Phe Asn Gly Glu Leu Ser Tyr Ala Ile Leu Val Cys Val Leu
290                 295                 300

Pro Gly Gly Thr Pro Arg Asp Trp Thr Tyr Gln Glu Ile Glu Ile Val
305                 310                 315                 320

Lys Val Val Ala Asp Gln Val Thr Val Ala Leu Asp His Ala Ala Val
                325                 330                 335

Leu Glu Glu Ser Gln Leu Met Arg Glu Lys Leu Ala Glu Gln Asn Arg
            340                 345                 350

Ala Leu Gln Met Ala Lys Arg Asp Ala Leu Arg Ala Ser Gln Ala Arg
        355                 360                 365

Asn Ala Phe Gln Lys Thr Met Ser Glu Gly Met Arg Arg Pro Met His
370                 375                 380

Ser Ile Leu Gly Leu Leu Ser Met Ile Gln Asp Glu Lys Leu Ser Asp
385                 390                 395                 400

Glu Gln Lys Met Ile Val Asp Thr Met Val Lys Thr Gly Asn Val Met
                405                 410                 415

Ser Asn Leu Val Gly Asp Ser Met Asp Val Pro Asp Gly Arg Phe Gly
            420                 425                 430

Thr Glu Met Lys Pro Phe Ser Leu His Arg Thr Ile His Glu Ala Ala
        435                 440                 445

Cys Met Ala Arg Cys Leu Cys Leu Cys Asn Gly Ile Arg Phe Leu Val
450                 455                 460

Asp Ala Glu Lys Ser Leu Pro Asp Asn Val Val Gly Asp Glu Arg Arg
465                 470                 475                 480

Val Phe Gln Val Ile Leu His Ile Val Gly Ser Leu Val Lys Pro Arg
                485                 490                 495

Lys Arg Gln Glu Gly Ser Ser Leu Met Phe Lys Val Leu Lys Glu Arg
            500                 505                 510

Gly Ser Leu Asp Arg Ser Asp His Arg Trp Ala Ala Trp Arg Ser Pro
        515                 520                 525

Ala Ser Ser Ala Asp Gly Asp Val Tyr Ile Arg Phe Glu Met Asn Val
530                 535                 540

Glu Asn Asp Asp Ser Ser Ser Gln Ser Phe Ala Ser Val Ser Ser Arg
545                 550                 555                 560

Asp Gln Glu Val Gly Asp Val Arg Phe Ser Gly Gly Tyr Gly Leu Gly
                565                 570                 575

Gln Asp Leu Ser Phe Gly Val Cys Lys Lys Val Val Gln Leu Ile His
            580                 585                 590

Gly Asn Ile Ser Val Val Pro Gly Ser Asp Gly Ser Pro Glu Thr Met
```

```
                    595                 600                 605
Ser Leu Leu Pro Arg Phe Arg Arg Pro Ser Ile Ser Val His Gly
    610                 615                 620

Ser Ser Glu Ser Pro Ala Pro Asp His His Ala His Pro His Ser Asn
625                 630                 635                 640

Ser Leu Leu Arg Gly Leu Gln Val Leu Leu Val Asp Thr Asn Asp Ser
                645                 650                 655

Asn Arg Ala Val Thr Arg Lys Leu Leu Glu Lys Leu Gly Cys Asp Val
            660                 665                 670

Thr Ala Val Ser Ser Gly Phe Asp Cys Leu Thr Ala Ile Ala Pro Gly
        675                 680                 685

Ser Ser Ser Pro Ser Thr Ser Phe Gln Val Val Leu Asp Leu Gln
    690                 695                 700

Met Ala Glu Met Asp Gly Tyr Glu Val Ala Met Arg Ile Arg Ser Arg
705                 710                 715                 720

Ser Trp Pro Leu Ile Val Ala Thr Thr Val Gly Leu Asp Glu Glu Met
                725                 730                 735

Trp Asp Lys Cys Ala Gln Ile Gly Ile Asn Gly Val Val Arg Lys Pro
            740                 745                 750

Val Val Leu Arg Ala Met Glu Ser Glu Leu Arg Arg Val Leu Leu Gln
        755                 760                 765

Ala Asp Gln Leu Leu
    770

<210> SEQ ID NO 35
<211> LENGTH: 2217
<212> TYPE: DNA
<213> ORGANISM: Arabidopsis thaliana

<400> SEQUENCE: 35
atggaagtct gcaattgtat tgaaccgcaa tggccagcgg atgaattgtt aatgaaatac      60
caatacatct ccgatttctt cattgcgatt gcgtattttt cgattcctct tgagttgatt     120
tactttgtga agaaatcagc cgtgtttccg tatagatggg tacttgttca gtttggtgct     180
tttatcgttc tttgtggagc aactcatctt attaacttat ggactttcac tacgcattcg     240
agaaccgtgg cgcttgtgat gactaccgcg aaggtgttaa ccgctgttgt ctcgtgtgct     300
actgcgttga tgcttgttca tattattcct gatcttttga gtgttaagac tcgggagctt     360
ttcttgaaaa ataaagctgc tgagctcgat agagaaatgg gattgattcg aactcaggaa     420
gaaaccggaa ggcatgtgag aatgttgact catgagatta gaagcacttt agatagacat     480
actattttaa agactacact tgttgagctt ggtaggacat tagctttgga ggagtgtgca     540
ttgtggatgc ctactagaac tgggttagag ctacagcttt cttatacact tcgtcatcaa     600
catcccgtgg agtatacggt tcctattcaa ttaccggtga ttaaccaagt gtttggtact     660
agtagggctg taaaaatatc tcctaattct cctgtggcta ggttgagacc tgtttctggg     720
aaatatatgc taggggaggt ggtcgctgtg agggttccgc ttctccacct ttctaatttt     780
cagattaatg actggcctga gctttcaaca aagagatatg ctttgatggt tttgatgctt     840
ccttcagata gtgcaaggca atggcatgtc catgagttgg aactcgttga agtcgtcgct     900
gatcaggtgg ctgtagctct ctcacatgct gcgatcctag aagagtcgat gcgagctagg     960
gaccttctca tggagcagaa tgttgctctt gatctagcta gacgagaagc agaaacagca    1020
atccgtgccc gcaatgattt cctagcggtt atgaaccatg aaatgcgaac accgatgcat    1080
```

-continued

```
gcgattattg cactctcttc cttactccaa gaaacggaac taaccccctga acaaagactg   1140 atggtggaaa caatacttaa aagtagtaac cttttggcaa ctttgatgaa tgatgtctta   1200
gatctttcaa ggttagaaga tggaagtctt caacttgaac ttgggacatt caatcttcat   1260
acattattta gagaggtcct caatctgata aagcctatag cggttgttaa gaaattaccc   1320
atcacactaa atcttgcacc agatttgcca gaatttgttg ttggggatga gaaacggcta   1380
atgcagataa tattaaatat agttggtaat gctgtgaaat tctccaaaca aggtagtatc   1440
tccgtaaccg ctcttgtcac caagtcagac acacgagctg ctgactttt tgtcgtgcca   1500 actgggagtc atttctactt gagagtgaag gtaaaagact ctggagcagg aataaatcct   1560
caagacattc caaagatttt cactaaattt gctcaaacac aatctttagc gacgagaagc   1620
tcgggtggta gtgggcttgg cctcgccatc tccaagaggt ttgtgaatct gatggagggt   1680
aacatttgga ttgagagcga tggtcttgga aaaggatgca cggctatctt tgatgttaaa   1740
cttgggatct cagaacgttc aaacgaatct aaacagtcgg gcataccgaa agttccagcc   1800
attccccgac attcaaattt cactggactt aaggttcttg tcatggatga aacggggta   1860 agtagaatgg tgacgaaggg acttcttgta caccttgggt gcgaagtgac cacggtgagt   1920
tcaaacgagg agtgtctccg agttgtgtcc catgagcaca aagtggtctt catggacgtg   1980
tgcatgcccg gggtcgaaaa ctaccaaatc gctctccgta ttcacgagaa attcacaaaa   2040
caacgccacc aacggccact acttgtggca ctcagtggta acactgacaa atccacaaaa   2100
gagaaatgca tgagctttgg tctagacggt gtgttgctca aacccgtatc actagacaac   2160
ataagagatg ttctgtctga tcttctcgag ccccgggtac tgtacgaggg catgtaa     2217
```

<210> SEQ ID NO 36
<211> LENGTH: 738
<212> TYPE: PRT
<213> ORGANISM: Arabidopsis thaliana

<400> SEQUENCE: 36

```
Met Glu Val Cys Asn Cys Ile Glu Pro Gln Trp Pro Ala Asp Glu Leu
 1               5                  10                  15

Leu Met Lys Tyr Gln Tyr Ile Ser Asp Phe Phe Ile Ala Ile Ala Tyr
            20                  25                  30

Phe Ser Ile Pro Leu Glu Leu Ile Tyr Phe Val Lys Lys Ser Ala Val
        35                  40                  45

Phe Pro Tyr Arg Trp Val Leu Val Gln Phe Gly Ala Phe Ile Val Leu
    50                  55                  60

Cys Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175
```

```
Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240

Lys Tyr Met Leu Gly Glu Val Val Ala Arg Val Pro Leu Leu His
                245                 250                 255

Leu Ser Asn Phe Gln Ile Asn Asp Trp Pro Glu Leu Ser Thr Lys Arg
        260                 265                 270

Tyr Ala Leu Met Val Leu Met Leu Pro Ser Asp Ser Ala Arg Gln Trp
        275                 280                 285

His Val His Glu Leu Glu Leu Val Glu Val Val Ala Asp Gln Val Ala
        290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
            340                 345                 350

His Glu Met Arg Thr Pro Met His Ala Ile Ile Ala Leu Ser Ser Leu
                355                 360                 365

Leu Gln Glu Thr Glu Leu Thr Pro Glu Gln Arg Leu Met Val Glu Thr
370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
            405                 410                 415

Phe Asn Leu His Thr Leu Phe Arg Glu Val Leu Asn Leu Ile Lys Pro
            420                 425                 430

Ile Ala Val Val Lys Lys Leu Pro Ile Thr Leu Asn Leu Ala Pro Asp
        435                 440                 445

Leu Pro Glu Phe Val Val Gly Asp Glu Lys Arg Leu Met Gln Ile Ile
450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
                500                 505                 510

Asp Ser Gly Ala Gly Ile Asn Pro Gln Asp Ile Pro Lys Ile Phe Thr
        515                 520                 525

Lys Phe Ala Gln Thr Gln Ser Leu Ala Thr Arg Ser Ser Gly Gly Ser
        530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
```

```
            595                 600                 605
Gly Leu Lys Val Leu Val Met Asp Glu Asn Gly Val Ser Arg Met Val
        610                 615                 620
Thr Lys Gly Leu Leu Val His Leu Gly Cys Glu Val Thr Thr Val Ser
625                 630                 635                 640
Ser Asn Glu Glu Cys Leu Arg Val Val Ser His Glu His Lys Val Val
                645                 650                 655
Phe Met Asp Val Cys Met Pro Gly Val Glu Asn Tyr Gln Ile Ala Leu
            660                 665                 670
Arg Ile His Glu Lys Phe Thr Lys Gln Arg His Gln Arg Pro Leu Leu
        675                 680                 685
Val Ala Leu Ser Gly Asn Thr Asp Lys Ser Thr Lys Glu Lys Cys Met
690                 695                 700
Ser Phe Gly Leu Asp Gly Val Leu Leu Lys Pro Val Ser Leu Asp Asn
705                 710                 715                 720
Ile Arg Asp Val Leu Ser Asp Leu Leu Glu Pro Arg Val Leu Tyr Glu
                725                 730                 735
Gly Met
```

<210> SEQ ID NO 37
<211> LENGTH: 2154
<212> TYPE: DNA
<213> ORGANISM: Arabidopsis thaliana

<400> SEQUENCE: 37

```
atggaagtct gcaattgtat tgaaccgcaa tggccagcgg atgaattgtt aatgaaatac      60
caatacatct ccgatttctt cattgcgatt gcgtatttt cgattcctct tgagttgatt     120
tactttgtga agaaatcagc cgtgtttccg tatagatggg tacttgttca gtttggtgct     180
tttatcgttc tttgtggagc aactcatctt attaacttat ggactttcac tacgcattcg     240
agaaccgtgg cgcttgtgat gactaccgcg aaggtgttaa ccgctgttgt ctcgtgtgct     300
actgcgttga tgcttgttca tattattcct gatctttga gtgttaagac tcgggagctt     360
ttcttgaaaa ataaagctgc tgagctcgat agagaaatgg gattgattcg aactcaggaa     420
gaaaccggaa ggcatgtgag aatgttgact catgagatta aagcacttt agatagacat     480
actatttaa agactacact tgttgagctt ggtaggacat agctttgga ggagtgtgca     540
tgtggatgc ctactagaac tgggttagag ctacagcttt cttatacact tcgtcatcaa     600
catcccgtgg agtatacggt tcctattcaa ttaccggtga ttaaccaagt gtttggtact     660
agtagggctg taaaaatatc tcctaattct cctgtggcta ggttgagacc tgtttctggg     720
aaatatatgc taggggaggt ggtcgctgtg agggttccgc ttctccacct ttctaatttt     780
cagattaatg actggcctga gctttcaaca aagagatatg ctttgatggt tttgatgctt     840
ccttcagata gtgcaaggca atggcatgtc gatgagttgg aactcgttga agtcgtcgct     900
gatcaggtgg ctgtagctct ctcacatgct gcgatcctag aagagtcgat gcgagctagg     960
gaccttctca tggagcagaa tgttgctctt gatctagcta acgagaagc agaaacagca    1020
atccgtgccc gcaatgattt cctagcggtt atgaaccatg aaatgcgaac accgatgcat    1080
gcgattattg cactctcttc cttactccaa gaaacggaac taacccctga caaagactg     1140
atggtggaaa caatacttaa aagtagtaac ctttggcaa cttttgatgaa tgatgtctta    1200
gatctttcaa ggttagaaga tggaagtctt caacttgaac ttgggacatt caatcttcat    1260
acattatttta gagaggtcct caatctgata aagcctatag cggttgttaa gaaattaccc    1320
```

-continued

| | |
|---|---|
| atcacactaa atcttgcacc agatttgcca gaatttgttg ttggggatga gaaacggcta | 1380 |
| atgcagataa tattaaatat agttggtaat gctgtgaaat tctccaaaca aggtagtatc | 1440 |
| tccgtaaccg ctcttgtcac caagtcagac acacgagctg ctgactttt tgtcgtgcca | 1500 |
| actgggagtc atttctactt gagagtgaag gtaaaagact ctggagcagg aataaatcct | 1560 |
| caagacattc caaagatttt cactaaattt gctcaaacac aatctttagc gacgagaagc | 1620 |
| tcgggtggta gtgggcttgg cctcgccatc tccaagaggt tgtgaatct gatggagggt | 1680 |
| aacatttgga ttgagagcga tggtcttgga aaaggatgca cggctatctt tgatgttaaa | 1740 |
| cttgggatct cagaacgttc aaacgaatct aaacagtcgg gcataccgaa agttccagcc | 1800 |
| attccccgac attcaaattt cactggactt aaggttcttg tcatggatga aacgggta | 1860 |
| agtagaatgg tgacgaaggg acttcttgta caccttgggt gcgaagtgac cacggtgagt | 1920 |
| tcaaacgagg agtgtctccg agttgtgtcc catgagcaca aagtggtctt catggacgtg | 1980 |
| tgcatgcccg gggtcgaaaa ctaccaaatc gctctccgta ttcacgagaa attcacaaaa | 2040 |
| caacgccacc aacggccact acttgtggca ctcagtggta acactgacaa atccacaaaa | 2100 |
| gagaaatgca tgagctttgg tctagacgtg tgttgctcaa acccgtatca ctag | 2154 |

<210> SEQ ID NO 38
<211> LENGTH: 717
<212> TYPE: PRT
<213> ORGANISM: Arabidopsis thaliana

<400> SEQUENCE: 38

Met Glu Val Cys Asn Cys Ile Glu Pro Gln Trp Pro Ala Asp Glu Leu
1               5                   10                  15

Leu Met Lys Tyr Gln Tyr Ile Ser Asp Phe Phe Ile Ala Ile Ala Tyr
            20                  25                  30

Phe Ser Ile Pro Leu Glu Leu Ile Tyr Phe Val Lys Lys Ser Ala Val
        35                  40                  45

Phe Pro Tyr Arg Trp Val Leu Val Gln Phe Gly Ala Phe Ile Val Leu
    50                  55                  60

Cys Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

```
Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
            245                 250                 255

Leu Ser Asn Phe Gln Ile Asn Asp Trp Pro Glu Leu Ser Thr Lys Arg
        260                 265                 270

Tyr Ala Leu Met Val Leu Met Leu Pro Ser Asp Ser Ala Arg Gln Trp
    275                 280                 285

His Val Asp Glu Leu Glu Leu Val Glu Val Val Ala Asp Gln Val Ala
290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
            325                 330                 335

Ala Glu Thr Ala Ile Arg Ala Arg Asn Asp Phe Leu Ala Val Met Asn
        340                 345                 350

His Glu Met Arg Thr Pro Met His Ala Ile Ile Ala Leu Ser Ser Leu
    355                 360                 365

Leu Gln Glu Thr Glu Leu Thr Pro Gln Arg Leu Met Val Glu Thr
370                 375                 380

Ile Leu Lys Ser Ser Asn Leu Leu Ala Thr Leu Met Asn Asp Val Leu
385                 390                 395                 400

Asp Leu Ser Arg Leu Glu Asp Gly Ser Leu Gln Leu Glu Leu Gly Thr
            405                 410                 415

Phe Asn Leu His Thr Leu Phe Arg Glu Val Leu Asn Leu Ile Lys Pro
        420                 425                 430

Ile Ala Val Val Lys Lys Leu Pro Ile Thr Leu Asn Leu Ala Pro Asp
    435                 440                 445

Leu Pro Glu Phe Val Val Gly Asp Glu Lys Arg Leu Met Gln Ile Ile
450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
            485                 490                 495

Phe Val Val Pro Thr Gly Ser His Phe Tyr Leu Arg Val Lys Val Lys
        500                 505                 510

Asp Ser Gly Ala Gly Ile Asn Pro Gln Asp Ile Pro Lys Ile Phe Thr
    515                 520                 525

Lys Phe Ala Gln Thr Gln Ser Leu Ala Thr Arg Ser Ser Gly Gly Ser
530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
            565                 570                 575

Phe Asp Val Lys Leu Gly Ile Ser Glu Arg Ser Asn Glu Ser Lys Gln
        580                 585                 590

Ser Gly Ile Pro Lys Val Pro Ala Ile Pro Arg His Ser Asn Phe Thr
    595                 600                 605

Gly Leu Lys Val Leu Val Met Asp Glu Asn Gly Val Ser Arg Met Val
610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
```

```
                      645                 650                 655
Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
            675                 680                 685

Val Ala Leu Ser Gly Asn Thr Asp Lys Ser Thr Lys Glu Lys Cys Met
            690                 695                 700

Ser Phe Gly Leu Asp Val Cys Cys Ser Asn Pro Tyr His
705                 710                 715

<210> SEQ ID NO 39
<211> LENGTH: 690
<212> TYPE: DNA
<213> ORGANISM: Arabidopsis thaliana

<400> SEQUENCE: 39
atgatgggca gtgtcgagct gaatctgagg gagactgagc tgtgtcttgg tcttcccggt    60
ggagatacag tggctccggt aaccggaaac aagagagggt ctcagagac ggttgatctg    120 aagctaaatc tgaataatga gcctgcaaac aaggaaggat ctacgactca tgacgtcgtg   180
acttttgatt ccaaggagaa gagtgcttgt cctaaagatc agccaaaacc tccggccaag   240
gcacaagttg tgggatggcc accggtgaga tcataccgga gaacgtgat ggtttcctgc     300 caaaaatcaa gcggtggccc ggaggcggcg gcgttcgtga aggtatcaat ggacggagca   360
ccgtacttga ggaaaatcga tttgaggatg tataaaagct acgatgagct ttctaatgct   420
ttgtccaaca tgttcagctc ttttaccatg gcaaacatg gaggagaaga aggaatgata    480
gacttcatga atgagaggaa attgatggat ttggtgaata gctgggacta tgttccctct   540
tatgaagaca aagacggtga ttggatgctc gtcggcgacg ttccttggcc aatgttcgtc   600
gatacatgca agcgtttacg tctcatgaaa ggatcggatg ccattggtct cgctccgagg   660
gcgatggaga agtgcaagag cagagcttga                                    690

<210> SEQ ID NO 40
<211> LENGTH: 229
<212> TYPE: PRT
<213> ORGANISM: Arabidopsis thaliana

<400> SEQUENCE: 40

Met Met Gly Ser Val Glu Leu Asn Leu Arg Glu Thr Glu Leu Cys Leu
1               5                   10                  15

Gly Leu Pro Gly Gly Asp Thr Val Ala Pro Val Thr Gly Asn Lys Arg
            20                  25                  30

Gly Phe Ser Glu Thr Val Asp Leu Lys Leu Asn Leu Asn Asn Glu Pro
        35                  40                  45

Ala Asn Lys Glu Gly Ser Thr Thr His Asp Val Val Thr Phe Asp Ser
    50                  55                  60

Lys Glu Lys Ser Ala Cys Pro Lys Asp Pro Ala Lys Pro Pro Ala Lys
65                  70                  75                  80

Ala Gln Val Val Gly Trp Pro Pro Val Arg Ser Tyr Arg Lys Asn Val
            85                  90                  95

Met Val Ser Cys Gln Lys Ser Ser Gly Gly Pro Glu Ala Ala Ala Phe
            100                 105                 110

Val Lys Val Ser Met Asp Gly Ala Pro Tyr Leu Arg Lys Ile Asp Leu
        115                 120                 125

Arg Met Tyr Lys Ser Tyr Asp Glu Leu Ser Asn Ala Leu Ser Asn Met
```

```
                130               135               140
Phe Ser Ser Phe Thr Met Gly Lys His Gly Gly Glu Gly Met Ile
145                 150                 155                 160

Asp Phe Met Asn Glu Arg Lys Leu Met Asp Leu Val Asn Ser Trp Asp
                    165                 170                 175

Tyr Val Pro Ser Tyr Glu Asp Lys Asp Gly Asp Trp Met Leu Val Gly
                180                 185                 190

Asp Val Pro Trp Pro Met Phe Val Asp Thr Cys Lys Arg Leu Arg Leu
                    195                 200                 205

Met Lys Gly Ser Asp Ala Ile Gly Leu Ala Pro Arg Ala Met Glu Lys
                210                 215                 220

Cys Lys Ser Arg Ala
225

<210> SEQ ID NO 41
<211> LENGTH: 732
<212> TYPE: DNA
<213> ORGANISM: Arabidopsis thaliana

<400> SEQUENCE: 41
atgatcggcc aacttatgaa cctcaaggcc acggagctct gtctcggcct ccccggcggc      60
gctgaagcag ttgagagtcc tgccaaatcg gcggtgggaa gcaagagagg cttctccgaa     120
accgttgatc tcatgctcaa tcttcaatct aacaaagaag ctccgttga tctcaaaaac     180
gtttctgctg ttcccaagga agactaccc ttaaagatc cttctaagcc tcctgctaaa      240
gcacaagtgg tgggatggcc acctgtgagg aactacagga gaacatgat gactcagcag     300
aagaccagta gtggtgcgga ggaggccagc agtgagaagg ccgggaactt tggtggagga     360
gcagccggag ccggcttggt gaaggtctcc atggacggtg ctccatatct gaggaaagtt     420
gacctcaaga tgtacaaaag ctaccaggat ctttctgatg cattggccaa atgttcagc     480
tcctttacta tgggaaacta tggagcacaa ggaatgatag atttcatgaa cgagagcaag     540
ctaatgaatc tgctgaatag ctctgagtat gtgccaagct acgaggacaa agatggtgac     600
tggatgctcg ttggcgatgt cccatgggaa atgtttgtcg agtcttgcaa cgtttgcgc     660
attatgaagg atctgaagc agttggactt gctccgagag caatggagaa gtactgcaag     720
aacagatctt ga                                                        732

<210> SEQ ID NO 42
<211> LENGTH: 243
<212> TYPE: PRT
<213> ORGANISM: Arabidopsis thaliana

<400> SEQUENCE: 42

Met Ile Gly Gln Leu Met Asn Leu Lys Ala Thr Glu Leu Cys Leu Gly
1               5                   10                  15

Leu Pro Gly Gly Ala Glu Ala Val Glu Ser Pro Ala Lys Ser Ala Val
            20                  25                  30

Gly Ser Lys Arg Gly Phe Ser Glu Thr Val Asp Leu Met Leu Asn Leu
        35                  40                  45

Gln Ser Asn Lys Glu Gly Ser Val Asp Leu Lys Asn Val Ser Ala Val
    50                  55                  60

Pro Lys Glu Lys Thr Thr Leu Lys Asp Pro Ser Lys Pro Pro Ala Lys
65                  70                  75                  80

Ala Gln Val Val Gly Trp Pro Pro Val Arg Asn Tyr Arg Lys Asn Met
                85                  90                  95
```

```
Met Thr Gln Gln Lys Thr Ser Ser Gly Ala Glu Ala Ser Ser Glu
            100                 105                 110
Lys Ala Gly Asn Phe Gly Gly Ala Ala Gly Ala Gly Leu Val Lys
        115                 120                 125
Val Ser Met Asp Gly Ala Pro Tyr Leu Arg Lys Val Asp Leu Lys Met
130                 135                 140
Tyr Lys Ser Tyr Gln Asp Leu Ser Asp Ala Leu Ala Lys Met Phe Ser
145                 150                 155                 160
Ser Phe Thr Met Gly Asn Tyr Gly Ala Gln Gly Met Ile Asp Phe Met
                165                 170                 175
Asn Glu Ser Lys Leu Met Asn Leu Leu Asn Ser Ser Glu Tyr Val Pro
            180                 185                 190
Ser Tyr Glu Asp Lys Asp Gly Asp Trp Met Leu Val Gly Asp Val Pro
        195                 200                 205
Trp Glu Met Phe Val Glu Ser Cys Lys Arg Leu Arg Ile Met Lys Gly
    210                 215                 220
Ser Glu Ala Val Gly Leu Ala Pro Arg Ala Met Glu Lys Tyr Cys Lys
225                 230                 235                 240
Asn Arg Ser

<210> SEQ ID NO 43
<211> LENGTH: 2148
<212> TYPE: DNA
<213> ORGANISM: Arabidopsis thaliana

<400> SEQUENCE: 43
atgaaaagct tgcatgtggc ggccaacgcc ggagatctgg ctgaggattg tggaatactc      60
ggtggagacg ctgatgatac tgttttgatg gatggaattg atgaagttgg tagagagatc     120
tggttagatg accatggagg agataataat catgttcatg gtcatcaaga tgatgatttg     180
attgttcatc atgacccttc aatcttctat ggagatctcc caacgcttcc tgatttccca     240
tgcatgtcgt cttcatcatc gtcttcaaca tctccagctc ctgtcaacgc aatcgtctcc     300
tcagcctctt cttcttcggc agcttcttcc tccacttcct cagctgcttc ttgggctata     360
ttgagatcag atggagaaga tccgactcca aaccaaaacc aatacgcatc aggaaactgt     420
gacgactctt ctggtgcatt gcaatccaca gcttccatgg agattccatt agacagcagt     480
caaggttttg gttgcggcga aggcggtggt gattgcattg atatgatgga cttttcggg     540
tacatggatc tacttgatag caacgagttc tttgacacct cagctatatt agccaagac     600
gacgacacgc aaaaccctaa cttgatggac caaacccttg agacaagag agaccaggtc     660
gttgttccga tgttggagaa taacagtggt ggagacatgc aaatgatgaa ttcttccttg     720
gaacaggacg atgatctcgc tgctgtgttt ttggagtggc taaagaacaa caaggagact     780
gtgtcggctg aggatttgag gaaagtaaag ataaagaaag ctacgattga atcagcggca     840
agaagactag gcggtggtaa agaagcgatg aagcagcttt taaagctgat tcttgaatgg     900
gtccaaacta atcacttaca aagaagacgc accaccacca ccaccaccaa cctctcttat     960
caacaatcat ccaacaaga tccatttcaa aaccctaacc ctaataacaa caacctaatc    1020
ccaccgtccg accaaacctg tttctcacct tcaacatggg ttcctccacc accacaacaa    1080
caagcttttg tctcggaccc gggttttgga tacatgcctg ctccaaacta tccgccacag    1140
ccagagttcc ttcctttact tgaatctcca ccgtcatggc caccaccacc acagtctggt    1200
cccatgccac atcaacaatt ccccatgccg ccaacctcgc agtataatca atttggagat    1260
```

-continued

```
ccaacaggtt tcaatggata caacatgaat ccgtaccaat atccttatgt tcctgcagga   1320
caaatgagag atcagagatt actccgtttg tgttcctcag caactaaaga ggcaagaaag   1380
aaacggatgg cgagacagag gaggttcttg tctcatcacc acagacataa caacaacaac   1440
aacaacaaca ataatcagca gaaccaaacc caaatcggag aaacctgtgc cgcggtggct   1500
ccacaactta accccgtggc acaaccgcc acgggaggga cctggatgta ttggcctaat   1560
gtcccggcag tgccgcctca attaccgcca gtgatggaga ctcagttacc caccatggac   1620
cgagctggct cagcttctgc tatgccacgt cagcaggtgg taccagatcg ccggcaggga   1680
tggaaaccag aaaagaattt gcggtttctc ttgcagaaag tcttgaagca aagcgacgtg   1740
ggtaacctcg gaaggatcgt tttgccaaaa aagaagctg agacacactt gccggagcta   1800
gaggcaagag acggcatctc tctggccatg gaagacatcg gaacctctcg tgtttggaac   1860
atgcgctaca ggttttggcc taacaacaaa agcaggatgt atctcctcga gaacaccggc   1920
gattttgtga aaccaatgg gctccaagaa ggtgatttca tagtcatata ctccgacgtc   1980
aaattgatac gaggggttaa agtaagacaa ccgagcggac aaaagccgga ggctccaccg   2040
tcgtcagcag ctacgaagag acaaaacaag tcgcaaagga acataaacaa taactctccg   2100
tcggcgaatg tggtggtcgc ttcaccaact tctcaaactg ttaaatga               2148
```

```
<210> SEQ ID NO 44
<211> LENGTH: 715
<212> TYPE: PRT
<213> ORGANISM: Arabidopsis thaliana

<400> SEQUENCE: 44
```

Met Lys Ser Leu His Val Ala Ala Asn Ala Gly Asp Leu Ala Glu Asp
 1               5                  10                  15

Cys Gly Ile Leu Gly Gly Asp Ala Asp Asp Thr Val Leu Met Asp Gly
                20                  25                  30

Ile Asp Glu Val Gly Arg Glu Ile Trp Leu Asp His Gly Gly Asp
            35                  40                  45

Asn Asn His Val His Gly His Gln Asp Asp Leu Ile Val His His
        50                  55                  60

Asp Pro Ser Ile Phe Tyr Gly Asp Leu Pro Thr Leu Pro Asp Phe Pro
 65                  70                  75                  80

Cys Met Ser Ser Ser Ser Ser Ser Thr Ser Pro Ala Pro Val Asn
                    85                  90                  95

Ala Ile Val Ser Ser Ala Ser Ser Ser Ala Ser Ser Ser Thr
                100                 105                 110

Ser Ser Ala Ala Ser Trp Ala Ile Leu Arg Ser Asp Gly Glu Asp Pro
            115                 120                 125

Thr Pro Asn Gln Asn Gln Tyr Ala Ser Gly Asn Cys Asp Asp Ser Ser
        130                 135                 140

Gly Ala Leu Gln Ser Thr Ala Ser Met Glu Ile Pro Leu Asp Ser Ser
145                 150                 155                 160

Gln Gly Phe Gly Cys Gly Glu Gly Gly Asp Cys Ile Asp Met Met
                165                 170                 175

Glu Thr Phe Gly Tyr Met Asp Leu Leu Asp Ser Asn Glu Phe Phe Asp
                180                 185                 190

Thr Ser Ala Ile Phe Ser Gln Asp Asp Thr Gln Asn Pro Asn Leu
            195                 200                 205

Met Asp Gln Thr Leu Glu Arg Gln Glu Asp Gln Val Val Val Pro Met

-continued

```
            210                 215                 220
Leu Glu Asn Asn Ser Gly Gly Asp Met Gln Met Met Asn Ser Ser Leu
225                 230                 235                 240

Glu Gln Asp Asp Leu Ala Ala Val Phe Leu Glu Trp Leu Lys Asn
                245                 250                 255

Asn Lys Glu Thr Val Ser Ala Glu Asp Leu Arg Lys Val Lys Ile Lys
                    260                 265                 270

Lys Ala Thr Ile Glu Ser Ala Ala Arg Arg Leu Gly Gly Gly Lys Glu
                275                 280                 285

Ala Met Lys Gln Leu Leu Lys Leu Ile Leu Glu Trp Val Gln Thr Asn
290                 295                 300

His Leu Gln Arg Arg Arg Thr Thr Thr Thr Thr Thr Asn Leu Ser Tyr
305                 310                 315                 320

Gln Gln Ser Phe Gln Gln Asp Pro Phe Gln Asn Pro Asn Pro Asn Asn
                    325                 330                 335

Asn Asn Leu Ile Pro Pro Ser Asp Gln Thr Cys Phe Ser Pro Ser Thr
                340                 345                 350

Trp Val Pro Pro Pro Gln Gln Gln Ala Phe Val Ser Asp Pro Gly
                355                 360                 365

Phe Gly Tyr Met Pro Ala Pro Asn Tyr Pro Pro Gln Pro Glu Phe Leu
                370                 375                 380

Pro Leu Leu Glu Ser Pro Pro Ser Trp Pro Pro Pro Gln Ser Gly
385                 390                 395                 400

Pro Met Pro His Gln Gln Phe Pro Met Pro Pro Thr Ser Gln Tyr Asn
                    405                 410                 415

Gln Phe Gly Asp Pro Thr Gly Phe Asn Gly Tyr Asn Met Asn Pro Tyr
                420                 425                 430

Gln Tyr Pro Tyr Val Pro Ala Gly Gln Met Arg Asp Gln Arg Leu Leu
                435                 440                 445

Arg Leu Cys Ser Ser Ala Thr Lys Glu Ala Arg Lys Lys Arg Met Ala
                450                 455                 460

Arg Gln Arg Arg Phe Leu Ser His His His Arg His Asn Asn Asn Asn
465                 470                 475                 480

Asn Asn Asn Asn Asn Gln Gln Asn Gln Thr Gln Ile Gly Glu Thr Cys
                    485                 490                 495

Ala Ala Val Ala Pro Gln Leu Asn Pro Val Ala Thr Ala Thr Gly
                500                 505                 510

Gly Thr Trp Met Tyr Trp Pro Asn Val Pro Ala Val Pro Pro Gln Leu
                515                 520                 525

Pro Pro Val Met Glu Thr Gln Leu Pro Thr Met Asp Arg Ala Gly Ser
530                 535                 540

Ala Ser Ala Met Pro Arg Gln Gln Val Val Pro Asp Arg Arg Gln Gly
545                 550                 555                 560

Trp Lys Pro Glu Lys Asn Leu Arg Phe Leu Leu Gln Lys Val Leu Lys
                    565                 570                 575

Gln Ser Asp Val Gly Asn Leu Gly Arg Ile Val Leu Pro Lys Lys Glu
                580                 585                 590

Ala Glu Thr His Leu Pro Glu Leu Glu Ala Arg Asp Gly Ile Ser Leu
                595                 600                 605

Ala Met Glu Asp Ile Gly Thr Ser Arg Val Trp Asn Met Arg Tyr Arg
610                 615                 620

Phe Trp Pro Asn Asn Lys Ser Arg Met Tyr Leu Leu Glu Asn Thr Gly
625                 630                 635                 640
```

Asp Phe Val Lys Thr Asn Gly Leu Gln Glu Gly Asp Phe Ile Val Ile
                645                 650                 655

Tyr Ser Asp Val Lys Leu Ile Arg Gly Val Lys Val Arg Gln Pro Ser
            660                 665                 670

Gly Gln Lys Pro Glu Ala Pro Pro Ser Ser Ala Ala Thr Lys Arg Gln
        675                 680                 685

Asn Lys Ser Gln Arg Asn Ile Asn Asn Asn Ser Pro Ser Ala Asn Val
    690                 695                 700

Val Val Ala Ser Pro Thr Ser Gln Thr Val Lys
705                 710                 715

<210> SEQ ID NO 45
<211> LENGTH: 1305
<212> TYPE: DNA
<213> ORGANISM: Arabidopsis thaliana

<400> SEQUENCE: 45
atggaggaag tatctccggc gatcgcaggt cctttcaggc cattctccga aacccagatg      60
gatttcaccg ggatcagatt gggtaaaggt tactgcaata accaatactc aaatcaagat     120
tccgagaacg gagatctaat ggtttcgtta ccggagactt catcatgctc tgtttctggg     180
tcacatggtt ctgaatctag gaaagttttg atttctcgga tcaattctcc taatttaaac     240
atgaaggaat cagcagctgc tgatatagtc gtcgttgata tctccgccgg agatgagatc     300
aacggctcag atgttactag cgagaagaag atgatcagca acagagag taggagtttg      360 tttgaattca gagtgtgcc tttgtatggt ttcacttcga tttgtggaag aagaccagag     420
atggaagatg ctgtttcgac tataccaaga ttccttcaat cttcttctgg ttccatgtta     480
gatggtcggt tgatcctca atccgccgct catttcttcg gtgtttacga cggccatggc     540
ggttctcagg tagcgaacta ttgtagagag aggatgcatt tggctttggc ggaggagata     600
gctaaggaga aaccgatgct ctgcgatggt gatacgtggc tggagaagtg gaagaaagct     660
cttttcaact cgttcctgag agttgactcg gagattgagt cagttgcgcc ggagacggtt     720
gggtcaacgt cggtggttgc cgttgttttc ccgtctcaca tcttcgtcgc taactgcggt     780
gactctagag ccgttctttg ccgcggcaaa actgcacttc cattatccgt tgaccataaa     840
ccggatagaa agatgaagc tgcgaggatt gaagccgcag agggaaagt gattcagtgg      900 aatggagctc gtgttttcgg tgttctcgcc atgtcgagat ccattggcga tagatacttg     960
aaaccatcca tcattcctga tccggaagtg acggctgtga agagagtaaa agaagatgat    1020
tgtctgattt tggcgagtga cggggttgg gatgtaatga cggatgaaga agcgtgtgag     1080
atggcaagga agcggattct cttgtggcac aagaaaaacg cggtggctgg ggatgcatcg    1140
ttgctcgcgg atgagcggag aaaggaaggg aaagatcctg cggcgatgtc cgcggctgag    1200
tatttgtcaa agctggcgat acagagagga agcaaagaca acataagtgt ggtggtggtt    1260
gatttgaagc ctcggaggaa actcaagagc aaacccttga actga                   1305

<210> SEQ ID NO 46
<211> LENGTH: 434
<212> TYPE: PRT
<213> ORGANISM: Arabidopsis thaliana

<400> SEQUENCE: 46

Met Glu Glu Val Ser Pro Ala Ile Ala Gly Pro Phe Arg Pro Phe Ser
 1               5                   10                  15

-continued

```
Glu Thr Gln Met Asp Phe Thr Gly Ile Arg Leu Gly Lys Gly Tyr Cys
             20                  25                  30

Asn Asn Gln Tyr Ser Asn Gln Asp Ser Glu Asn Gly Asp Leu Met Val
         35                  40                  45

Ser Leu Pro Glu Thr Ser Ser Cys Ser Val Ser Gly Ser His Gly Ser
     50                  55                  60

Glu Ser Arg Lys Val Leu Ile Ser Arg Ile Asn Ser Pro Asn Leu Asn
 65                  70                  75                  80

Met Lys Glu Ser Ala Ala Ala Asp Ile Val Val Asp Ile Ser Ala
                 85                  90                  95

Gly Asp Glu Ile Asn Gly Ser Asp Val Thr Ser Glu Lys Lys Met Ile
             100                 105                 110

Ser Arg Thr Glu Ser Arg Ser Leu Phe Glu Phe Lys Ser Val Pro Leu
         115                 120                 125

Tyr Gly Phe Thr Ser Ile Cys Gly Arg Arg Pro Glu Met Glu Asp Ala
     130                 135                 140

Val Ser Thr Ile Pro Arg Phe Leu Gln Ser Ser Gly Ser Met Leu
145                 150                 155                 160

Asp Gly Arg Phe Asp Pro Gln Ser Ala Ala His Phe Phe Gly Val Tyr
                 165                 170                 175

Asp Gly His Gly Gly Ser Gln Val Ala Asn Tyr Cys Arg Glu Arg Met
             180                 185                 190

His Leu Ala Leu Ala Glu Glu Ile Ala Lys Glu Lys Pro Met Leu Cys
         195                 200                 205

Asp Gly Asp Thr Trp Leu Glu Lys Trp Lys Lys Ala Leu Phe Asn Ser
     210                 215                 220

Phe Leu Arg Val Asp Ser Glu Ile Glu Ser Val Ala Pro Glu Thr Val
225                 230                 235                 240

Gly Ser Thr Ser Val Val Ala Val Val Phe Pro Ser His Ile Phe Val
                 245                 250                 255

Ala Asn Cys Gly Asp Ser Arg Ala Val Leu Cys Arg Gly Lys Thr Ala
             260                 265                 270

Leu Pro Leu Ser Val Asp His Lys Pro Asp Arg Glu Asp Glu Ala Ala
         275                 280                 285

Arg Ile Glu Ala Ala Gly Gly Lys Val Ile Gln Trp Asn Gly Ala Arg
     290                 295                 300

Val Phe Gly Val Leu Ala Met Ser Arg Ser Ile Gly Asp Arg Tyr Leu
305                 310                 315                 320

Lys Pro Ser Ile Ile Pro Asp Pro Glu Val Thr Ala Val Lys Arg Val
                 325                 330                 335

Lys Glu Asp Asp Cys Leu Ile Leu Ala Ser Asp Gly Val Trp Asp Val
             340                 345                 350

Met Thr Asp Glu Glu Ala Cys Glu Met Ala Arg Lys Arg Ile Leu Leu
         355                 360                 365

Trp His Lys Lys Asn Ala Val Ala Gly Asp Ala Ser Leu Leu Ala Asp
     370                 375                 380

Glu Arg Arg Lys Glu Gly Lys Asp Pro Ala Ala Met Ser Ala Ala Glu
385                 390                 395                 400

Tyr Leu Ser Lys Leu Ala Ile Gln Arg Gly Ser Lys Asp Asn Ile Ser
                 405                 410                 415

Val Val Val Val Asp Leu Lys Pro Arg Arg Lys Leu Lys Ser Lys Pro
             420                 425                 430

Leu Asn
```

<210> SEQ ID NO 47
<211> LENGTH: 2466
<212> TYPE: DNA
<213> ORGANISM: Arabidopsis thaliana

<400> SEQUENCE: 47

| | | | | | |
|---|---|---|---|---|---|
| atggaaatgc | ccggtagaag | atctaattac | actttgctta | gtcaattttc | tgacgatcag | 60 |
| gtgtcagttt | ccgtcaccgg | agctcctccg | cctcactatg | attccttgtc | gagcgaaaac | 120 |
| aggagcaacc | ataacagcgg | gaacaccggg | aaagctaagg | cggagagagg | cggatttgat | 180 |
| tgggatccta | gcggtggtgg | tggtggtgat | cataggttga | ataatcaacc | gaatcgggtt | 240 |
| gggaataata | tgtatgcttc | gtctctaggg | ttgcaaaggc | aatccagtgg | gagtagtttc | 300 |
| ggtgagagct | ctttgtctgg | ggattattac | atgcctacgc | tttctgcggc | ggctaacgag | 360 |
| atcgaatctg | ttggatttcc | tcaagatgat | gggtttaggc | ttggatttgg | tggtggtgga | 420 |
| ggagatttga | ggatacagat | ggcggcggac | tccgctggag | ggtcttcatc | tgggaagagc | 480 |
| tgggcgcagc | agacggagga | gagttatcag | ctgcagcttg | cattggcgtt | aaggctttcg | 540 |
| tcggaggcta | cttgtgccga | cgatccgaac | tttctggatc | ctgtaccgga | cgagtctgct | 600 |
| ttacggactt | cgccaagttc | agccgaaacc | gtttcacatc | gtttctgggt | taatggctgc | 660 |
| ttatcgtact | atgataaagt | tcctgatggg | ttttatatga | tgaatggtct | ggatccctat | 720 |
| atttggacct | tatgcatcga | cctgcatgaa | agtggtcgca | tcccttcaat | tgaatcatta | 780 |
| agagctgttg | attctggtgt | tgattcttcg | cttgaagcga | tcatagttga | taggcgtagt | 840 |
| gatccagcct | tcaaggaact | tcacaataga | gtccacgaca | tatcttgtag | ctgcattacc | 900 |
| acaaaagagg | ttgttgatca | gctggcaaag | cttatctgca | atcgtatggg | gggtccagtt | 960 |
| atcatggggg | aagatgagtt | ggttcccatg | tggaaggagt | gcattgatgg | tctaaaagaa | 1020 |
| atctttaaag | tggtggttcc | cataggtagc | ctctctgttg | gactctgcag | acatcgagct | 1080 |
| ttactcttca | aagtactggc | tgacataatt | gatttaccct | gtcgaattgc | caaaggatgt | 1140 |
| aaatattgta | atagagacga | tgccgcttcg | tgccttgtca | ggtttgggct | tgatagggag | 1200 |
| tacctggttg | atttagtagg | aaagccaggt | cacttatggg | agcctgattc | cttgctaaat | 1260 |
| ggtccttcat | ctatctcaat | ttcttctcct | ctgcggtttc | cacgaccaaa | gccagttgaa | 1320 |
| cccgcagtcg | attttaggtt | actagccaaa | caatatttct | ccgatagcca | gtctcttaat | 1380 |
| cttgttttcg | atcctgcatc | agatgatatg | ggattctcaa | tgtttcatag | gcaatatgat | 1440 |
| aatccgggtg | gagagaatga | cgcattggca | gaaaatggtg | gtgggtcttt | gccacccagt | 1500 |
| gctaatatgc | ctccacagaa | catgatgcgt | gcgtcaaatc | aaattgaagc | agcacctatg | 1560 |
| aatgccccac | caatcagtca | gccagttcca | aacagggcaa | ataggaaact | tggacttgat | 1620 |
| ggtgatgata | tggacatccc | gtggtgtgat | cttaatataa | agaaaagat | tggagcaggt | 1680 |
| tcctttggca | ctgtccaccg | tgctgagtgg | catggctcgg | atgttgctgt | gaaaattctc | 1740 |
| atggagcaag | acttccatgc | tgagcgtgtt | aatgagttct | taagagaggt | tgcgataatg | 1800 |
| aaacgccttc | gccaccctaa | cattgttctc | ttcatgggtg | cggtcactca | acctccaaat | 1860 |
| ttgtcaatag | tgacagaata | tttgtcaaga | ggtagtttat | acagactttt | gcataaaagt | 1920 |
| ggagcaaggg | agcaattaga | tgagagacgt | cgcctgagta | tggcttatga | tgtggctaag | 1980 |
| ggaatgaatt | atcttcacaa | tcgcaatcct | ccaattgtgc | atagagatct | aaaatctcca | 2040 |
| aacttattgg | ttgacaaaaa | atatacagtc | aaggtttgtg | attttggtct | ctcgcgattg | 2100 |

-continued

```
aaggccagca cgtttctttc ctcgaagtca gcagctggaa cccccgagtg gatggcacca   2160
gaagtcctgc gagatgagcc gtctaatgaa aagtcagatg tgtacagctt cggggtcatc   2220 tgtgggagc ttgctacatt gcaacaacca tggggtaact taaatccggc tcaggttgta    2280
gctgcggttg gtttcaagtg taaacggctg gagatcccgc gtaatctgaa tcctcaggtt   2340
gcagccataa tcgagggttg ttggaccaat gagccatgga agcgtccatc atttgcaact   2400
ataatggact tgctaagacc attgatcaaa tcagcggttc ctccgcccaa ccgctcggat   2460
ttgtaa                                                              2466

<210> SEQ ID NO 48
<211> LENGTH: 821
<212> TYPE: PRT
<213> ORGANISM: Arabidopsis thaliana

<400> SEQUENCE: 48

Met Glu Met Pro Gly Arg Arg Ser Asn Tyr Thr Leu Leu Ser Gln Phe
 1               5                  10                  15

Ser Asp Asp Gln Val Ser Val Ser Val Thr Gly Ala Pro Pro His
             20                  25                  30

Tyr Asp Ser Leu Ser Ser Glu Asn Arg Ser Asn His Asn Ser Gly Asn
         35                  40                  45

Thr Gly Lys Ala Lys Ala Glu Arg Gly Gly Phe Asp Trp Asp Pro Ser
     50                  55                  60

Gly Gly Gly Gly Gly Asp His Arg Leu Asn Asn Gln Pro Asn Arg Val
 65                  70                  75                  80

Gly Asn Asn Met Tyr Ala Ser Ser Leu Gly Leu Gln Arg Gln Ser Ser
                 85                  90                  95

Gly Ser Ser Phe Gly Glu Ser Ser Leu Ser Gly Asp Tyr Tyr Met Pro
            100                 105                 110

Thr Leu Ser Ala Ala Ala Asn Glu Ile Glu Ser Val Gly Phe Pro Gln
        115                 120                 125

Asp Asp Gly Phe Arg Leu Gly Phe Gly Gly Gly Gly Gly Asp Leu Arg
    130                 135                 140

Ile Gln Met Ala Ala Asp Ser Ala Gly Gly Ser Ser Ser Gly Lys Ser
145                 150                 155                 160

Trp Ala Gln Gln Thr Glu Glu Ser Tyr Gln Leu Gln Leu Ala Leu Ala
                165                 170                 175

Leu Arg Leu Ser Ser Glu Ala Thr Cys Ala Asp Asp Pro Asn Phe Leu
            180                 185                 190

Asp Pro Val Pro Asp Glu Ser Ala Leu Arg Thr Ser Pro Ser Ser Ala
        195                 200                 205

Glu Thr Val Ser His Arg Phe Trp Val Asn Gly Cys Leu Ser Tyr Tyr
    210                 215                 220

Asp Lys Val Pro Asp Gly Phe Tyr Met Met Asn Gly Leu Asp Pro Tyr
225                 230                 235                 240

Ile Trp Thr Leu Cys Ile Asp Leu His Glu Ser Gly Arg Ile Pro Ser
                245                 250                 255

Ile Glu Ser Leu Arg Ala Val Asp Ser Gly Val Asp Ser Ser Leu Glu
            260                 265                 270

Ala Ile Ile Val Asp Arg Arg Ser Asp Pro Ala Phe Lys Glu Leu His
        275                 280                 285

Asn Arg Val His Asp Ile Ser Cys Ser Cys Ile Thr Thr Lys Glu Val
    290                 295                 300
```

```
Val Asp Gln Leu Ala Lys Leu Ile Cys Asn Arg Met Gly Gly Pro Val
305                 310                 315                 320

Ile Met Gly Glu Asp Glu Leu Val Pro Met Trp Lys Glu Cys Ile Asp
            325                 330                 335

Gly Leu Lys Glu Ile Phe Lys Val Val Val Pro Ile Gly Ser Leu Ser
            340                 345                 350

Val Gly Leu Cys Arg His Arg Ala Leu Leu Phe Lys Val Leu Ala Asp
            355                 360                 365

Ile Ile Asp Leu Pro Cys Arg Ile Ala Lys Gly Cys Lys Tyr Cys Asn
        370                 375                 380

Arg Asp Asp Ala Ala Ser Cys Leu Val Arg Phe Gly Leu Asp Arg Glu
385                 390                 395                 400

Tyr Leu Val Asp Leu Val Gly Lys Pro Gly His Leu Trp Glu Pro Asp
                405                 410                 415

Ser Leu Leu Asn Gly Pro Ser Ser Ile Ser Ile Ser Ser Pro Leu Arg
            420                 425                 430

Phe Pro Arg Pro Lys Pro Val Glu Pro Ala Val Asp Phe Arg Leu Leu
        435                 440                 445

Ala Lys Gln Tyr Phe Ser Asp Ser Gln Ser Leu Asn Leu Val Phe Asp
450                 455                 460

Pro Ala Ser Asp Asp Met Gly Phe Ser Met Phe His Arg Gln Tyr Asp
465                 470                 475                 480

Asn Pro Gly Gly Glu Asn Asp Ala Leu Ala Glu Asn Gly Gly Gly Ser
                485                 490                 495

Leu Pro Pro Ser Ala Asn Met Pro Pro Gln Asn Met Met Arg Ala Ser
            500                 505                 510

Asn Gln Ile Glu Ala Ala Pro Met Asn Ala Pro Pro Ile Ser Gln Pro
        515                 520                 525

Val Pro Asn Arg Ala Asn Arg Glu Leu Gly Leu Asp Gly Asp Asp Met
        530                 535                 540

Asp Ile Pro Trp Cys Asp Leu Asn Ile Lys Glu Lys Ile Gly Ala Gly
545                 550                 555                 560

Ser Phe Gly Thr Val His Arg Ala Glu Trp His Gly Ser Asp Val Ala
                565                 570                 575

Val Lys Ile Leu Met Glu Gln Asp Phe His Ala Glu Arg Val Asn Glu
            580                 585                 590

Phe Leu Arg Glu Val Ala Ile Met Lys Arg Leu Arg His Pro Asn Ile
        595                 600                 605

Val Leu Phe Met Gly Ala Val Thr Gln Pro Pro Asn Leu Ser Ile Val
        610                 615                 620

Thr Glu Tyr Leu Ser Arg Gly Ser Leu Tyr Arg Leu Leu His Lys Ser
625                 630                 635                 640

Gly Ala Arg Glu Gln Leu Asp Glu Arg Arg Arg Leu Ser Met Ala Tyr
                645                 650                 655

Asp Val Ala Lys Gly Met Asn Tyr Leu His Asn Arg Asn Pro Pro Ile
            660                 665                 670

Val His Arg Asp Leu Lys Ser Pro Asn Leu Leu Val Asp Lys Lys Tyr
        675                 680                 685

Thr Val Lys Val Cys Asp Phe Gly Leu Ser Arg Leu Lys Ala Ser Thr
        690                 695                 700

Phe Leu Ser Ser Lys Ser Ala Ala Gly Thr Pro Glu Trp Met Ala Pro
705                 710                 715                 720

Glu Val Leu Arg Asp Glu Pro Ser Asn Glu Lys Ser Asp Val Tyr Ser
```

```
                    725                 730                 735
Phe Gly Val Ile Leu Trp Glu Leu Ala Thr Leu Gln Gln Pro Trp Gly
            740                 745                 750
Asn Leu Asn Pro Ala Gln Val Val Ala Val Gly Phe Lys Cys Lys
        755                 760                 765
Arg Leu Glu Ile Pro Arg Asn Leu Asn Pro Gln Val Ala Ala Ile Ile
    770                 775                 780
Glu Gly Cys Trp Thr Asn Glu Pro Trp Lys Arg Pro Ser Phe Ala Thr
785                 790                 795                 800
Ile Met Asp Leu Leu Arg Pro Leu Ile Lys Ser Ala Val Pro Pro Pro
                805                 810                 815
Asn Arg Ser Asp Leu
            820

<210> SEQ ID NO 49
<211> LENGTH: 35
<212> TYPE: DNA
<213> ORGANISM: Artificial Sequence
<220> FEATURE:
<223> OTHER INFORMATION: Primer

<400> SEQUENCE: 49
atggcgcgcc atggttcgtc ctggattcat tatgc                            35

<210> SEQ ID NO 50
<211> LENGTH: 34
<212> TYPE: DNA
<213> ORGANISM: Artificial Sequence
<220> FEATURE:
<223> OTHER INFORMATION: Primer

<400> SEQUENCE: 50
gcttaattaa tcaggctttg gattttaccg ggac                             34

<210> SEQ ID NO 51
<211> LENGTH: 34
<212> TYPE: DNA
<213> ORGANISM: Artificial Sequence
<220> FEATURE:
<223> OTHER INFORMATION: Primer

<400> SEQUENCE: 51
atggcgcgcc ggggaggcca ccaagaaagt gctg                             34

<210> SEQ ID NO 52
<211> LENGTH: 34
<212> TYPE: DNA
<213> ORGANISM: Artificial Sequence
<220> FEATURE:
<223> OTHER INFORMATION: Primer

<400> SEQUENCE: 52
tcttaattaa gctacattta tcattgccgg cctc                             34

<210> SEQ ID NO 53
<211> LENGTH: 37
<212> TYPE: DNA
<213> ORGANISM: Artificial Sequence
<220> FEATURE:
<223> OTHER INFORMATION: Primer

<400> SEQUENCE: 53
atggcgcgcc gagccgttat tagttttcat tcaaggg                          37
```

<210> SEQ ID NO 54
<211> LENGTH: 36
<212> TYPE: DNA
<213> ORGANISM: Artificial Sequence
<220> FEATURE:
<223> OTHER INFORMATION: Primer

<400> SEQUENCE: 54
agttaattaa tcttaactta ccaaggagcc gacaaa                                    36

<210> SEQ ID NO 55
<211> LENGTH: 33
<212> TYPE: DNA
<213> ORGANISM: Artificial Sequence
<220> FEATURE:
<223> OTHER INFORMATION: Primer

<400> SEQUENCE: 55
attggcgcgc ctggtgttgc agtgatttga ttc                                       33

<210> SEQ ID NO 56
<211> LENGTH: 33
<212> TYPE: DNA
<213> ORGANISM: Artificial Sequence
<220> FEATURE:
<223> OTHER INFORMATION: Primer

<400> SEQUENCE: 56
gcgttaatta agcagttcat agccagcaac caa                                       33

<210> SEQ ID NO 57
<211> LENGTH: 36
<212> TYPE: DNA
<213> ORGANISM: Artificial Sequence
<220> FEATURE:
<223> OTHER INFORMATION: Primer

<400> SEQUENCE: 57
atggcgcgcc atgaccacgt tattcctcct tattgc                                    36

<210> SEQ ID NO 58
<211> LENGTH: 33
<212> TYPE: DNA
<213> ORGANISM: Artificial Sequence
<220> FEATURE:
<223> OTHER INFORMATION: Primer

<400> SEQUENCE: 58
gcttaattaa catcactcaa ccgccgtacc gtc                                       33

<210> SEQ ID NO 59
<211> LENGTH: 31
<212> TYPE: DNA
<213> ORGANISM: Artificial Sequence
<220> FEATURE:
<223> OTHER INFORMATION: Primer

<400> SEQUENCE: 59
atggcgcgcc gggcaaaggc cattgtcgag t                                         31

<210> SEQ ID NO 60
<211> LENGTH: 34
<212> TYPE: DNA
<213> ORGANISM: Artificial Sequence
<220> FEATURE:

-continued

<223> OTHER INFORMATION: Primer

<400> SEQUENCE: 60
gcttaattaa ccggtactcg gtttagttca attt                          34

<210> SEQ ID NO 61
<211> LENGTH: 35
<212> TYPE: DNA
<213> ORGANISM: Artificial Sequence
<220> FEATURE:
<223> OTHER INFORMATION: Primer

<400> SEQUENCE: 61
atggcgcgcc catggatgtc ttgtttctcg atctg                         35

<210> SEQ ID NO 62
<211> LENGTH: 35
<212> TYPE: DNA
<213> ORGANISM: Artificial Sequence
<220> FEATURE:
<223> OTHER INFORMATION: Primer

<400> SEQUENCE: 62
gcttaattaa gatttctgac tttgaatgga aatgg                         35

<210> SEQ ID NO 63
<211> LENGTH: 33
<212> TYPE: DNA
<213> ORGANISM: Artificial Sequence
<220> FEATURE:
<223> OTHER INFORMATION: Primer

<400> SEQUENCE: 63
atggcgcgcc gaatcagaaa ttgggcgaag aag                           33

<210> SEQ ID NO 64
<211> LENGTH: 36
<212> TYPE: DNA
<213> ORGANISM: Artificial Sequence
<220> FEATURE:
<223> OTHER INFORMATION: Primer

<400> SEQUENCE: 64
gcttaattaa cacaacaatc actagctcag aagagc                        36

<210> SEQ ID NO 65
<211> LENGTH: 35
<212> TYPE: DNA
<213> ORGANISM: Artificial Sequence
<220> FEATURE:
<223> OTHER INFORMATION: Primer

<400> SEQUENCE: 65
atggcgcgcc atggagaaag tgaccaactc agact                         35

<210> SEQ ID NO 66
<211> LENGTH: 35
<212> TYPE: DNA
<213> ORGANISM: Artificial Sequence
<220> FEATURE:
<223> OTHER INFORMATION: Primer

<400> SEQUENCE: 66
gcttaattaa ttcaacggta gagacggtat gtggg                         35

```
<210> SEQ ID NO 67
<211> LENGTH: 33
<212> TYPE: DNA
<213> ORGANISM: Artificial Sequence
<220> FEATURE:
<223> OTHER INFORMATION: Primer

<400> SEQUENCE: 67
atggcgcgcc agaaaaaagc aatggcgtca gac                          33

<210> SEQ ID NO 68
<211> LENGTH: 34
<212> TYPE: DNA
<213> ORGANISM: Artificial Sequence
<220> FEATURE:
<223> OTHER INFORMATION: Primer

<400> SEQUENCE: 68
gcttaattaa ctcacagctt tcccttatct ttcc                         34

<210> SEQ ID NO 69
<211> LENGTH: 31
<212> TYPE: DNA
<213> ORGANISM: Artificial Sequence
<220> FEATURE:
<223> OTHER INFORMATION: Primer

<400> SEQUENCE: 69
atggcgcgcc gccagaggac gagacaaggg g                            31

<210> SEQ ID NO 70
<211> LENGTH: 34
<212> TYPE: DNA
<213> ORGANISM: Artificial Sequence
<220> FEATURE:
<223> OTHER INFORMATION: Primer

<400> SEQUENCE: 70
gcttaattaa ccattgggga tggtctaagt ttcc                         34

<210> SEQ ID NO 71
<211> LENGTH: 31
<212> TYPE: DNA
<213> ORGANISM: Artificial Sequence
<220> FEATURE:
<223> OTHER INFORMATION: Primer

<400> SEQUENCE: 71
atggcgcgcc atggaaggtg gagctgctct c                            31

<210> SEQ ID NO 72
<211> LENGTH: 33
<212> TYPE: DNA
<213> ORGANISM: Artificial Sequence
<220> FEATURE:
<223> OTHER INFORMATION: Primer

<400> SEQUENCE: 72
gcttaattaa gccaaataaa gacagatcga ggg                          33

<210> SEQ ID NO 73
<211> LENGTH: 32
<212> TYPE: DNA
<213> ORGANISM: Artificial Sequence
<220> FEATURE:
<223> OTHER INFORMATION: Primer
```

```
<400> SEQUENCE: 73
atggcgcgcc atggggtcat cacagtcttc gc                                    32

<210> SEQ ID NO 74
<211> LENGTH: 40
<212> TYPE: DNA
<213> ORGANISM: Artificial Sequence
<220> FEATURE:
<223> OTHER INFORMATION: Primer

<400> SEQUENCE: 74
gcttaattaa tcaatagtgt agaaacctaa caagtattgg                            40

<210> SEQ ID NO 75
<211> LENGTH: 32
<212> TYPE: DNA
<213> ORGANISM: Artificial Sequence
<220> FEATURE:
<223> OTHER INFORMATION: Primer

<400> SEQUENCE: 75
atggcgcgcc caaggggggt ctctgtcggt tc                                    32

<210> SEQ ID NO 76
<211> LENGTH: 33
<212> TYPE: DNA
<213> ORGANISM: Artificial Sequence
<220> FEATURE:
<223> OTHER INFORMATION: Primer

<400> SEQUENCE: 76
gcttaattaa catcatcatt gctctccaaa ccc                                   33

<210> SEQ ID NO 77
<211> LENGTH: 36
<212> TYPE: DNA
<213> ORGANISM: Artificial Sequence
<220> FEATURE:
<223> OTHER INFORMATION: Primer

<400> SEQUENCE: 77
atggcgcgcc gagaagaaga atcaaaatcc cacaca                                36

<210> SEQ ID NO 78
<211> LENGTH: 34
<212> TYPE: DNA
<213> ORGANISM: Artificial Sequence
<220> FEATURE:
<223> OTHER INFORMATION: Primer

<400> SEQUENCE: 78
gcttaattaa gcgatagatc gaataaaagg acca                                  34

<210> SEQ ID NO 79
<211> LENGTH: 34
<212> TYPE: DNA
<213> ORGANISM: Artificial Sequence
<220> FEATURE:
<223> OTHER INFORMATION: Primer

<400> SEQUENCE: 79
atggcgcgcc ccttcttgat tcgtcctctc cact                                  34

<210> SEQ ID NO 80
<211> LENGTH: 34
```

```
<212> TYPE: DNA
<213> ORGANISM: Artificial Sequence
<220> FEATURE:
<223> OTHER INFORMATION: Primer

<400> SEQUENCE: 80
gcttaattaa ccaccatctc ctccgattct cttc                                    34

<210> SEQ ID NO 81
<211> LENGTH: 36
<212> TYPE: DNA
<213> ORGANISM: Artificial Sequence
<220> FEATURE:
<223> OTHER INFORMATION: Primer

<400> SEQUENCE: 81
atggcgcgcc atggttaaag aaatagcttc ttggtt                                  36

<210> SEQ ID NO 82
<211> LENGTH: 35
<212> TYPE: DNA
<213> ORGANISM: Artificial Sequence
<220> FEATURE:
<223> OTHER INFORMATION: Primer

<400> SEQUENCE: 82
gcttaattaa ttagagaagt tggtcagctt gcaac                                   35

<210> SEQ ID NO 83
<211> LENGTH: 36
<212> TYPE: DNA
<213> ORGANISM: Artificial Sequence
<220> FEATURE:
<223> OTHER INFORMATION: Primer

<400> SEQUENCE: 83
atggcgcgcc atggaagtct gcaattgtat tgaacc                                  36

<210> SEQ ID NO 84
<211> LENGTH: 34
<212> TYPE: DNA
<213> ORGANISM: Artificial Sequence
<220> FEATURE:
<223> OTHER INFORMATION: Primer

<400> SEQUENCE: 84
gcttaattaa ttacatgccc tcgtacagta cccg                                    34

<210> SEQ ID NO 85
<211> LENGTH: 36
<212> TYPE: DNA
<213> ORGANISM: Artificial Sequence
<220> FEATURE:
<223> OTHER INFORMATION: Primer

<400> SEQUENCE: 85
atggcgcgcc atggaagtct gcaattgtat tgaacc                                  36

<210> SEQ ID NO 86
<211> LENGTH: 34
<212> TYPE: DNA
<213> ORGANISM: Artificial Sequence
<220> FEATURE:
<223> OTHER INFORMATION: Primer

<400> SEQUENCE: 86
```

```
gcttaattaa ttacatgccc tcgtacagta cccg                                34
```

<210> SEQ ID NO 87
<211> LENGTH: 31
<212> TYPE: DNA
<213> ORGANISM: Artificial Sequence
<220> FEATURE:
<223> OTHER INFORMATION: Primer

<400> SEQUENCE: 87

```
atggcgcgcc atgatgggca gtgtcgagct g                                   31
```

<210> SEQ ID NO 88
<211> LENGTH: 33
<212> TYPE: DNA
<213> ORGANISM: Artificial Sequence
<220> FEATURE:
<223> OTHER INFORMATION: Primer

<400> SEQUENCE: 88

```
gcttaattaa tcaagctctg ctcttgcact tct                                 33
```

<210> SEQ ID NO 89
<211> LENGTH: 33
<212> TYPE: DNA
<213> ORGANISM: Artificial Sequence
<220> FEATURE:
<223> OTHER INFORMATION: Primer

<400> SEQUENCE: 89

```
atggcgcgcc atgatcggcc aacttatgaa cct                                 33
```

<210> SEQ ID NO 90
<211> LENGTH: 37
<212> TYPE: DNA
<213> ORGANISM: Artificial Sequence
<220> FEATURE:
<223> OTHER INFORMATION: Primer

<400> SEQUENCE: 90

```
gcttaattaa tcaagatctg ttcttgcagt acttctc                             37
```

<210> SEQ ID NO 91
<211> LENGTH: 35
<212> TYPE: DNA
<213> ORGANISM: Artificial Sequence
<220> FEATURE:
<223> OTHER INFORMATION: Primer

<400> SEQUENCE: 91

```
atggcgcgcc ggagaaaata gttagctttg gtcgg                               35
```

<210> SEQ ID NO 92
<211> LENGTH: 33
<212> TYPE: DNA
<213> ORGANISM: Artificial Sequence
<220> FEATURE:
<223> OTHER INFORMATION: Primer

<400> SEQUENCE: 92

```
gcttaattaa ccaaacgagt ggtgcaatta cac                                 33
```

<210> SEQ ID NO 93
<211> LENGTH: 34
<212> TYPE: DNA
<213> ORGANISM: Artificial Sequence

```
<220> FEATURE:
<223> OTHER INFORMATION: Primer

<400> SEQUENCE: 93
atggcgcgcc atggaggaag tatctccggc gatc                           34

<210> SEQ ID NO 94
<211> LENGTH: 34
<212> TYPE: DNA
<213> ORGANISM: Artificial Sequence
<220> FEATURE:
<223> OTHER INFORMATION: Primer

<400> SEQUENCE: 94
gcttaattaa tcagttcaag ggtttgctct tgag                           34

<210> SEQ ID NO 95
<211> LENGTH: 33
<212> TYPE: DNA
<213> ORGANISM: Artificial Sequence
<220> FEATURE:
<223> OTHER INFORMATION: Primer

<400> SEQUENCE: 95
atggcgcgcc atggaaatgc ccggtagaag atc                            33

<210> SEQ ID NO 96
<211> LENGTH: 33
<212> TYPE: DNA
<213> ORGANISM: Artificial Sequence
<220> FEATURE:
<223> OTHER INFORMATION: Primer

<400> SEQUENCE: 96
gcttaattaa ttacaaatcc gagcggttgg gcg                            33

<210> SEQ ID NO 97
<211> LENGTH: 18
<212> TYPE: DNA
<213> ORGANISM: Artificial Sequence
<220> FEATURE:
<223> OTHER INFORMATION: Primer

<400> SEQUENCE: 97
caggaaacag ctatgacc                                             18

<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98
ctaaagggaa caaaagctg                                            19

<210> SEQ ID NO 99
<211> LENGTH: 18
<212> TYPE: DNA
<213> ORGANISM: Artificial Sequence
<220> FEATURE:
<223> OTHER INFORMATION: Primer

<400> SEQUENCE: 99
tgtaaaacga cggccagt                                             18
```

SUGAR AND LIPID METABOLISM REGULATORS IN PLANTS II

CROSS REFERENCE TO RELATED APPLICATIONS

This application is a divisional application of U.S. application Ser. No. 13/103,572 filed May 9, 2011, which is a divisional application of U.S. application Ser. No. 11/998,203 filed Nov. 29, 2007, which is a continuation of U.S. patent application Ser. No. 10/171,404, filed Jun. 4, 2002, which claims the priority benefit of U.S. Provisional Patent Application Ser. No. 60/295,680 filed Jun. 4, 2001, the entire contents of each above-mentioned application are hereby incorporated by reference in entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13987_00207_US. The size of the text file is 137 KB, and the text file was created on Sep. 19, 2012.

FIELD OF THE INVENTION

This invention relates generally to nucleic acid sequences encoding proteins that are related to the presence of seed storage compounds in plants. More specifically, the present invention relates to nucleic acid sequences encoding sugar and lipid metabolism regulator proteins and the use of these sequences in transgenic plants.

BACKGROUND ART

The study and genetic manipulation of plants has a long history that began even before the framed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al. 1995, Science 268:681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164) and rapeseed (Töpfer et al. 1995, Science 268:681-686), and non-traditional oil seed plants such as tobacco (Cahoon et al. 1992, Proc. Natl. Acad. Sci. USA 89:11184-11188).

Plant seed oils comprise both neutral and polar lipids (see Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes and the cell membrane. The neutral and polar lipids contain several common fatty acids (see Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo F. J. et al. 1993, Unusual Fatty Acids in Lipid Metabolism in Plants pp. 91-126, editor TS Moore Jr. CRC Press; Millar et al. 2000, Trends Plant Sci. 5:95-101).

TABLE 1

Plant Lipid Classes

| | |
|---|---|
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

Common Plant Fatty Acids

| | |
|---|---|
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| □-18:3 | Gamma-linolenic acid* |
| 20:0 | Arachidic acid |
| 22:6 | Docosahexanoic acid (DHA)* |
| 20:2 | Eicosadienoic acid |
| 20:4 | Arachidonic acid (AA)* |
| 20:5 | Eicosapentaenoic acid (EPA)* |
| 22:1 | Erucic acid |

*These fatty acids do not normally occur in plant seed oils, but their production in transgenic plant seed oil is of importance in plant biotechnology.

Lipids are synthesized from fatty acids and their synthesis may be divided into two parts: the prokaryotic pathway and the eukaryotic pathway (Browse et al. 1986, Biochemical J. 235:25-31; Ohlrogge & Browse 1995, Plant Cell 7:957-970). The prokaryotic pathway is located in plastids that are the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-keto-acyl-ACP-synthase III (KAS III) catalyzes a condensation reaction in which the acyl group from acetyl-CoA is transferred to malonyl-ACP to form 3-ketobutyryl-ACP. In a subsequent series of condensation, reduction and dehydration reactions the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first unsaturated double bond into the fatty acid. Thioesterases cleave the fatty acids from the ACP cofactor and free fatty acids are exported to the cytoplasm where they participate as fatty acyl-CoA esters in the eukaryotic pathway. In this pathway the fatty acids are esterified by glycerol-3-phosphate acyltransferase and lysophosphatidic acid acyltransferase to the sn-1 and sn-2 positions of glycerol-3-phosphate, respectively, to yield phosphatidic acid (PA). The PA is the precursor for other polar and neutral lipids, the latter being formed in the Kennedy pathway (Voelker 1996, Genetic Engineering ed.:Setlow 18:111-113; Shanklin & Cahoon 1998, Annu. Rev. Plant Physiol. Plant Mol. Biol. 49:611-641; Frentzen 1998, Lipids 100:161-166; Millar et al. 2000, Trends Plant Sci. 5:95-101).

Storage lipids in seeds are synthesized from carbohydrate-derived precursors. Plants have a complete glycolytic pathway in the cytosol (Plaxton 1996, Annu. Rev. Plant Physiol. Plant Mol. Biol. 47:185-214) and it has been shown that a complete pathway also exists in the plastids of rapeseeds (Kang & Rawsthorne 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions and the exact contribution of each reaction is still being debated (Ohlrogge & Browse 1995, Plant Cell 7:957-970). It is however accepted that a large part of the acetyl-CoA is derived from glucose-6-phospate and pyruvate that are imported from the cytoplasm into the plastids. Sucrose is produced in the source organs (leaves, or anywhere that photosynthesis occurs) and is transported to the developing seeds that are also termed sink organs. In the developing seeds, the sucrose is the precursor for all the storage compounds, i.e. starch, lipids and partly the seed storage proteins. Therefore, it is clear that carbohydrate metabolism in which sucrose plays a central role is very important to the accumulation of seed storage compounds.

Although lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (see, e.g., Töpfer et al. 1995, Science 268:681-686). For example, introduction of a $\Delta^{12}$-hydroxylase nucleic acid sequence into transgenic tobacco resulted in the introduction of a novel fatty acid, ricinoleic acid, into the tobacco seed oil (Van de Loo et al. 1995, Proc. Natl. Acad. Sci. USA 92:6743-6747). Tobacco plants have also been engineered to produce low levels of petroselinic acid by the introduction and expression of an acyl-ACP desaturase from coriander (Cahoon et al. 1992, Proc. Natl. Acad. Sci. USA 89:11184-11188).

The modification of seed oil content in plants has significant medical, nutritional and economic ramifications. With regard to the medical ramifications, the long chain fatty acids (C18 and longer) found in many seed oils have been linked to reductions in hypercholesterolemia and other clinical disorders related to coronary heart disease (Brenner 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid and acyl-ACP desaturase nucleic acid have been cloned and demonstrated to encode enzymes required for fatty acid synthesis in various plant species. Oleosin nucleic acid sequences from such different species as Brassica, soybean, carrot, pine and Arabidopsis thaliana have also been cloned and determined to encode proteins associated with the phospholipid monolayer membrane of oil bodies in those plants.

It has also been determined that two phytohormones, gibberellic acid (GA) and absisic acid (ABA), are involved in overall regulatory processes in seed development (e.g. Ritchie & Gilroy 1998, Plant Physiol. 116:765-776; Arenas-Huertero et al. 2000, Genes Dev. 14:2085-2096). Both the GA and ABA pathways are affected by okadaic acid, a protein phosphatase inhibitor (Kuo et al. 1996, Plant Cell. 8:259-269). The regulation of protein phosphorylation by kinases and phosphatases is accepted as a universal mechanism of cellular control (Cohen 1992, Trends Biochem. Sci. 17:408-413. Likewise, the plant hormones ethylene (e.g. Zhou et al. 1998, Proc. Natl. Acad. Sci. USA 95:10294-10299; Beaudoin et al. 2000, Plant Cell 2000:1103-1115) and auxin (e.g. Colon-Carmona et al. 2000, Plant Physiol. 124:1728-1738) are involved in controlling plant development as well.

Although several compounds are known that generally affect plant and seed development, there is a clear need to specifically identify factors that are more specific for the developmental regulation of storage compound accumulation and to identify genes which have the capacity to confer altered or increased oil production to its host plant and to other plant species. This invention discloses a large number of nucleic acid sequences from *Arabidopsis thaliana*. These nucleic acid sequences can be used to alter or increase the levels of seed storage compounds such as proteins, sugars and oils, in plants, including transgenic plants, such as rapeseed, canola, linseed, soybean, sunflower maize, oat, rye, barley, wheat, pepper, tagetes, cotton, oil palm, coconut palm, flax, castor and peanut, which are oilseed plants containing high amounts of lipid compounds.

SUMMARY OF THE INVENTION

The present invention provides novel isolated nucleic acid and amino acid sequences associated with the metabolism of seed storage compounds in plants.

The present invention also provides an isolated nucleic acid from *Arabidopsis* encoding a Lipid Metabolism Protein (LMP), or a portion thereof. These sequences may be used to modify or increase lipids and fatty acids, cofactors and enzymes in microorganisms and plants.

*Arabidopsis* plants are known to produce considerable amounts of fatty acids like linoleic and linolenic acid (see, e.g., Table 2) and for their close similarity in many aspects (gene homology etc.) to the oil crop plant *Brassica*. Therefore nucleic acid molecules originating from a plant like *Arabidopsis thaliana* are especially suited to modify the lipid and fatty acid metabolism in a host, especially in microorganisms and plants. Furthermore, nucleic acids from the plant *Arabidopsis thaliana* can be used to identify those DNA sequences and enzymes in other species which are useful to modify the biosynthesis of precursor molecules of fatty acids in the respective organisms.

The present invention further provides an isolated nucleic acid comprising a fragment of at least 15 nucleotides of a nucleic acid from a plant (*Arabidopsis thaliana*) encoding a Lipid Metabolism Protein (LMP), or a portion thereof.

Also provided by the present invention are polypeptides encoded by the nucleic acids, and heterologous polypeptides comprising polypeptides encoded by the nucleic acids, and antibodies to those polypeptides.

Additionally, the present invention relates to and provides the use of LMP nucleic acids in the production of transgenic plants having a modified level of a seed storage compound. A method of producing a transgenic plant with a modified level of a seed storage compound includes the steps of transforming a plant cell with an expression vector comprising a LMP nucleic acid, and generating a plant with a modified level of the seed storage compound from the plant cell. In a preferred embodiment, the plant is an oil producing species selected from the group consisting of rapeseed, canola, linseed, soybean, sunflower, maize, oat, rye, barley, wheat, pepper, tagetes, cotton, oil palm, coconut palm, flax, castor and peanut, for example.

According to the present invention, the compositions and methods described herein can be used to increase or decrease the level of a LMP in a transgenic plant comprising increasing or decreasing the expression of a LMP nucleic acid in the plant. Increased or decreased expression of the LMP nucleic acid can be achieved through in vivo mutagenesis of the LMP nucleic acid. The present invention can also be used to increase or decrease the level of a lipid in a seed oil, to increase or decrease the level of a fatty acid in a seed oil, or to increase or decrease the level of a starch in a seed or plant.

Also included herein is a seed produced by a transgenic plant transformed by a LMP DNA sequence, wherein the seed contains the LMP DNA sequence and wherein the plant is true breeding for a modified level of a seed storage compound. The present invention additionally includes a seed oil produced by the aforementioned seed.

Further provided by the present invention are vectors comprising the nucleic acids, host cells containing the vectors, and descendent plant materials produced by transforming a plant cell with the nucleic acids and/or vectors.

According to the present invention, the compounds, compositions, and methods described herein can be used to increase or decrease the level of a lipid in a seed oil, or to increase or decrease the level of a fatty acid in a seed oil, or to increase or decrease the level of a starch or other carbohydrate in a seed or plant. A method of producing a higher or lower than normal or typical level of storage compound in a transgenic plant, comprises expressing a LMP nucleic acid from *Arabidopsis thaliana* in the transgenic plant, wherein the transgenic plant is *Arabidopsis thaliana* or a species different from *Arabidopsis thaliana*. Also included herein are compositions and methods of the modification of the efficiency of production of a seed storage compound.

Accordingly, it is an object of the present invention to provide novel isolated LMP nucleic acids and isolated LMP amino acid sequences from *Arabidopsis thaliana*, as well as active fragments, analogs and orthologs thereof.

It is another object of the present invention to provide transgenic plants having modified levels of seed storage compounds, and in particular, modified levels of a lipid, a fatty acid or a sugar.

It is a further object of the present invention to provide methods for producing such aforementioned transgenic plants.

It is another object of the present invention to provide seeds and seed oils from such aforementioned transgenic plants.

These and other objects, features and advantages of the present invention will become apparent after a review of the following detailed description of the disclosed embodiments and the appended claims.

BRIEF DESCRIPTION OF THE FIGURES

FIGS. 1A-B: FIG. 1A shows the polynucleotide sequences of the open reading frame of Clone ID NO: pk002b from *Arabidopsis thaliana* (SEQ ID NO:1) of the present invention. The polynucleotide sequence contains 2253 nucleotides. FIG. 1B shows the deduced amino acid sequence of SEQ ID NO:1 (SEQ ID NO:2) (Clone ID NO: pk002b) of the present invention. The polypeptide sequence contains 750 amino acids. The standard one-letter abbreviation for amino acids is used to illustrate the deduced amino acid sequence.

FIG. 2A-B: FIG. 2A shows the polynucleotide sequences of the open reading frame of Clone ID NO: pk020b from *Arabidopsis thaliana* (SEQ ID NO:3) of the present invention. The polynucleotide sequence contains 681 nucleotides. FIG. 2B shows the deduced amino acid sequence of SEQ ID NO:3 (SEQ ID NO:4) (Clone ID NO: pk020b) of the present invention. The polypeptide sequence contains 226 amino acids. The standard one-letter abbreviation for amino acids is used to illustrate the deduced amino acid sequence.

FIGS. 3A-B: FIG. 3A shows the polynucleotide sequences of the open reading frame of Clone ID NO: pk033 from *Arabidopsis thaliana* (SEQ ID NO:5) of the present invention. The polynucleotide sequence contains 1815 nucleotides. FIG. 3B shows the deduced amino acid sequence of SEQ ID NO:5 (SEQ ID NO:6) (Clone ID NO: pk033) of the present invention. The polypeptide sequence contains 604 amino acids. The standard one-letter abbreviation for amino acids is used to illustrate the deduced amino acid sequence.

FIGS. 4A-13: FIG. 4A shows the polynucleotide sequences of the open reading frame of Clone ID NO: pk037 from *Arabidopsis thaliana* (SEQ ID NO:7) of the present invention. The polynucleotide sequence contains 1773 nucleotides. FIG. 4B shows the deduced amino acid sequence of SEQ ID NO:7 (SEQ ID NO:8) (Clone ID NO: pk037) of the present invention. The polypeptide sequence contains 590 amino acids. The standard one-letter abbreviation for amino acids is used to illustrate the deduced amino acid sequence.

FIGS. 5A-B: FIG. 5A shows the polynucleotide sequences of the open reading frame of Clone ID NO: pk038 from *Arabidopsis thaliana* (SEQ ID NO:9) of the present invention. The polynucleotide sequence contains 1035 nucleotides. FIG. 5B shows the deduced amino acid sequence of SEQ ID NO:9 (SEQ ID NO:10) (Clone ID NO: pk038) of the present invention. The polypeptide sequence contains 344 amino acids. The standard one-letter abbreviation for amino acids is used to illustrate the deduced amino acid sequence.

FIGS. 6A-B: FIG. 6A shows the polynucleotide sequences of the open reading frame of Clone ID NO: pk042a from *Arabidopsis thaliana* (SEQ ID NO:11) of the present invention. The polynucleotide sequence contains 804 nucleotides. FIG. 6B shows the deduced amino acid sequence of SEQ ID NO:11 (SEQ ID NO:12) (Clone ID NO: pk042a) of the present invention. The polypeptide sequence contains 267 amino acids. The standard one-letter abbreviation for amino acids is used to illustrate the deduced amino acid sequence.

FIGS. 7A-B: FIG. 7A shows the polynucleotide sequences of the open reading frame of Clone ID NO: pk053b from *Arabidopsis thaliana* (SEQ ID NO:13) of the present invention. The polynucleotide sequence contains 272 nucleotides. FIG. 7B shows the deduced amino acid sequence of SEQ ID NO:13 (SEQ ID NO:14) (Clone ID NO: pk053b) of the present invention. The polypeptide sequence contains 90 amino acids. The standard one-letter abbreviation for amino acids is used to illustrate the deduced amino acid sequence.

FIGS. 8A-B: FIG. 8A shows the polynucleotide sequences of the open reading frame of Clone ID NO: pk060 from *Arabidopsis thaliana* (SEQ ID NO:15) of the present invention. The polynucleotide sequence contains 603 nucleotides. FIG. 8B shows the deduced amino acid sequence of SEQ ID NO:15 (SEQ ID NO:16) (Clone ID NO: pk060) of the present invention. The polypeptide sequence contains 200 amino FIGS. 9A-B: FIG. 9A shows the polynucleotide sequences of the open reading frame of Clone ID NO: pk063b from *Arabidopsis thaliana* (SEQ ID NO:17) of the present invention. The polynucleotide sequence contains 1746 nucleotides. FIG. 9B shows the deduced amino acid sequence of SEQ ID NO:17 (SEQ ID NO:18) (Clone ID NO: pk063b) of the present invention. The polypeptide sequence contains 581 amino acids. The standard one-letter abbreviation for amino acids is used to illustrate the deduced amino acid sequence.

FIGS. 10A-B: FIG. 10A shows the polynucleotide sequences of the open reading frame of Clone ID NO: pk064 from *Arabidopsis thaliana* (SEQ ID NO:19) of the present invention. The polynucleotide sequence contains 1347 nucleotides. FIG. 10B shows the deduced amino acid sequence of SEQ ID NO:19 (SEQ ID NO:20) (Clone ID NO: pk064) of the present invention. The polypeptide sequence contains 448 amino acids. The standard one-letter abbreviation for amino acids is used to illustrate the deduced amino acid sequence.

FIGS. 11A-B. FIG. 11A shows the polynucleotide sequences of the open reading frame of Clone ID NO: pk073 from *Arabidopsis thaliana* (SEQ ID NO:21) of the present invention. The polynucleotide sequence contains 564 nucleotides. FIG. 11B shows the deduced amino acid sequence of SEQ ID NO:21 (SEQ ID NO:22) (Clone ID NO: pk073) of the present invention. The polypeptide sequence contains 187 amino acids. The standard one-letter abbreviation for amino acids is used to illustrate the deduced amino acid sequence.

FIGS. 12A-B. FIG. 12A shows the polynucleotide sequences of the open reading frame of Clone ID NO: pk082 from *Arabidopsis thaliana* (SEQ ID NO:23) of the present invention. The polynucleotide sequence contains 753 nucleotides. FIG. 12B shows the deduced amino acid sequence of SEQ ID NO:23 (SEQ ID NO:24) (Clone ID NO: pk082) of the present invention. The polypeptide sequence contains 250 amino acids. The standard one-letter abbreviation for amino acids is used to illustrate the deduced amino acid sequence.

FIGS. 13A-B. FIG. 13A shows the polynucleotide sequences of the open reading frame of Clone ID NO: pk084 from *Arabidopsis thaliana* (SEQ ID NO:25) of the present invention. The polynucleotide sequence contains 1218 nucleotides. FIG. 13B shows the deduced amino acid sequence of SEQ ID NO:25 (SEQ ID NO:26) (Clone ID NO: pk084) of the present invention. The polypeptide sequence contains 405 amino acids. The standard one-letter abbreviation for amino acids is used to illustrate the deduced amino acid sequence.

FIGS. 14A-B. FIG. 14A shows the polynucleotide sequences of the open reading frame of Clone ID NO: pk086 from *Arabidopsis thaliana* (SEQ ID NO:27) of the present invention. The polynucleotide sequence contains 420 nucleotides. FIG. 14B shows the deduced amino acid sequence of SEQ ID NO:27 (SEQ ID NO:28) (Clone ID NO: pk086) of the present invention. The polypeptide sequence contains 139 amino acids. The standard one-letter abbreviation for amino acids is used to illustrate the deduced amino acid sequence.

FIGS. 15A-B. FIG. 15A shows the polynucleotide sequences of the open reading frame of Clone ID NO: pk088 from *Arabidopsis thaliana* (SEQ ID NO:29) of the present invention. The polynucleotide sequence contains 549 nucleotides. FIG. 15B shows the deduced amino acid sequence of SEQ ID NO:29 (SEQ ID NO:30) (Clone ID NO: pk088) of the present invention. The polypeptide sequence contains 182 amino acids. The standard one-letter abbreviation for amino acids is used to illustrate the deduced amino acid sequence.

FIGS. 16A-B. FIG. 16A shows the polynucleotide sequences of the open reading frame of Clone ID NO: pk095 from *Arabidopsis thaliana* (SEQ ID NO:31) of the present invention. The polynucleotide sequence contains 987 nucleotides. FIG. 16B shows the deduced amino acid sequence of SEQ ID NO:31 (SEQ ID NO:32) (Clone ID NO: pk095) of the present invention. The polypeptide sequence contains 328 amino acids. The standard one-letter abbreviation for amino acids is used to illustrate the deduced amino acid sequence.

FIGS. 17A-B. FIG. 17A shows the polynucleotide sequences of the open reading frame of Clone ID NO: pk096 from *Arabidopsis thaliana* (SEQ ID NO:33) of the present invention. The polynucleotide sequence contains 2322 nucleotides. FIG. 17B shows the deduced amino acid sequence of SEQ ID NO:33 (SEQ ID NO:34) (Clone ID NO: pk096) of the present invention. The polypeptide sequence contains 773 amino acids. The standard one-letter abbreviation for amino acids is used to illustrate the deduced amino acid sequence.

FIGS. 18A-D. FIG. 18A shows the polynucleotide sequences of the open reading frame of Clone ID NO: pk097a from *Arabidopsis thaliana* (SEQ ID NO:35) of the present invention. The polynucleotide sequence contains 2217 nucleotides. FIG. 18B shows the deduced amino acid sequence of SEQ ID NO:35 (SEQ ID NO:36) (Clone ID NO: pk097a) of the present invention. The polypeptide sequence contains 738 amino acids. The standard one-letter abbreviation for amino acids is used to illustrate the deduced amino acid sequence. FIG. 18C shows the polynucleotide sequences of the open reading frame of Clone ID NO: pk097b from *Arabidopsis thaliana* (SEQ ID NO:37) of the present invention. The polynucleotide sequence contains 2154 nucleotides. FIG. 18D shows the deduced amino acid sequence of SEQ ID NO:37 (SEQ ID NO:38) (Clone ID NO: pk097b) of the present invention. The polypeptide sequence contains 717 amino acids. The standard one-letter abbreviation for amino acids is used to illustrate the deduced amino acid sequence.

FIGS. 19A-B. FIG. 19A shows the polynucleotide sequences of the open reading frame of Clone ID NO: pk098 from *Arabidopsis thaliana* (SEQ ID NO:39) of the present invention. The polynucleotide sequence contains 690 nucleotides. FIG. 19B shows the deduced amino acid sequence of SEQ ID NO:39 (SEQ ID NO:40) (Clone ID NO: pk098) of the present invention. The polypeptide sequence contains 229 amino acids. The standard one-letter abbreviation for amino acids is used to illustrate the deduced amino acid sequence.

FIGS. 20A-B. FIG. 20A shows the polynucleotide sequences of the open reading frame of Clone ID NO: pk099 from *Arabidopsis thaliana* (SEQ ID NO:41) of the present invention. The polynucleotide sequence contains 732 nucleotides. FIG. 20B shows the deduced amino acid sequence of SEQ ID NO:41 (SEQ ID NO:42) (Clone ID NO: pk099) of the present invention. The polypeptide sequence contains 243 amino acids. The standard one-letter abbreviation for amino acids is used to illustrate the deduced amino acid sequence.

FIGS. 21A-B. FIG. 21A shows the polynucleotide sequences of the open reading frame of Clone ID NO: pk100 from *Arabidopsis thaliana* (SEQ ID NO:43) of the present invention. The polynucleotide sequence contains 2148 nucleotides. FIG. 21B shows the deduced amino acid sequence of SEQ ID NO:43 (SEQ ID NO:44) (Clone ID NO: pk100) of the present invention. The polypeptide sequence contains 715 amino acids. The standard one-letter abbreviation for amino acids is used to illustrate the deduced amino acid sequence.

FIGS. 22A-B. FIG. 22A shows the polynucleotide sequences of the open reading frame of Clone ID NO: pk105 from *Arabidopsis thaliana* (SEQ ID NO:45) of the present invention. The polynucleotide sequence contains 1305 nucleotides. FIG. 22B shows the deduced amino acid sequence of SEQ ID NO:45 (SEQ ID NO:46) (Clone ID NO: pk105) of the present invention. The polypeptide sequence contains 434 amino acids. The standard one-letter abbreviation for amino acids is used to illustrate the deduced amino acid sequence.

FIGS. 23A-B. FIG. 23A shows the polynucleotide sequences of the open reading frame of Clone ID NO: pk107 from *Arabidopsis thaliana* (SEQ ID NO:47) of the present invention. The polynucleotide sequence contains 2466 nucleotides. FIG. 23B shows the deduced amino acid sequence of SEQ ID NO:47 (SEQ ID NO:48) (Clone ID NO: pk107) of the present invention. The polypeptide sequence contains 821 amino acids. The standard one-letter abbreviation for amino acids is used to illustrate the deduced amino acid sequence.

DETAILED DESCRIPTION OF THE PREFERRED EMBODIMENTS

The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

In accordance with the purpose(s) of this invention, as embodied and broadly described herein, this invention, in one aspect, provides an isolated nucleic acid from a plant (*Arabidopsis thaliana*) encoding a Lipid Metabolism Protein (LMP), or a portion thereof.

One aspect of the invention pertains to isolated nucleic acid molecules that encode LMP polypeptides or biologically active portions thereof, as well as nucleic acid fragments sufficient for use as hybridization probes or primers for the identification or amplification of an LMP-encoding nucleic acid (e.g., LMP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one which is substantially separated from other nucleic acid molecules which are present in the natural source of the nucleic acid. Preferably, an "isolated" nucleic acid is substantially free of sequences which naturally flank the nucleic acid (i.e., sequences located at the 5' and 3' ends of the nucleic acid) in the genomic DNA of the organism from which the nucleic acid is derived. For example, in various embodiments, the isolated LMP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Arabidopsis thaliana* cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence of the Figures, or a portion thereof, can be isolated using standard molecular biology techniques and the sequence information provided herein. For example, an *Arabidopsis thaliana* LMP cDNA can be isolated from an *Arabidopsis thaliana* library using all or portion of one of the sequences of the Figures as a hybridization probe and standard hybridization techniques (e.g., as described in Sambrook et al. 1989, *Molecular Cloning: A Laboratory Manual*. 2nd, ed., Cold Spring Harbor Laboratory, Cold Spring Harbor Laboratory Press, Cold Spring Harbor, N.Y.). Moreover, a nucleic acid molecule encompassing all or a portion of one of the sequences of the Figures can be isolated by the polymerase chain reaction using oligonucleotide primers designed based upon this sequence (e.g., a nucleic acid molecule encompassing all or a portion of one of the sequences of the Figures can be isolated by the polymerase chain reaction using oligonucleotide primers designed based upon this same sequence the Figures). For example, mRNA can be isolated from plant cells (e.g., by the guanidinium-thiocyanate extraction procedure of Chirgwin et al. 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in the Figures. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a LMP nucleotide sequence can be prepared by standard synthetic techniques, e.g., using an automated DNA synthesizer.

In a preferred embodiment, an isolated nucleic acid of the invention comprises one of the polynucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47. These polynucleotide correspond to the *Arabidopsis thaliana* LMP cDNAs of the invention. These cDNAs comprise sequences encoding LMPs (i.e., the "coding region"), as well as 5' untranslated sequences and 3' untranslated sequences. Alternatively, the nucleic acid molecules can comprise only the coding region of any of the polynucleotide sequences described herein. Examples of polynucleotides comprising only the coding region or open reading frame (ORF) are shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47.

For the purposes of this application, it will be understood that each of the polynucleotide sequences set forth in the Figures has an identifying entry number (e.g., pk002b). Each of these sequences may generally comprise three parts: a 5' upstream region, a coding region, and a downstream region. The particular sequences shown in the figures represent the open reading frames. The putative functions of these proteins are indicated in Table 4.

In another preferred embodiment, an isolated nucleic acid molecule of the present invention encodes a polypeptide that is able to participate in the metabolism of seed storage compounds such as lipids, starch and seed storage proteins and that contains a DNA-binding (or transcription factor) domain, a protein kinase domain, a signal transduction domain, a protease domain, or a carbohydarte metabolism domain. Examples of isolated LMPs that contain such domains can be found in Table 5. LMPs containing a DNA-binding domain include those shown in SEQ ID NO:4, SEQ ID NO:8, SEQ ID NO:20, SEQ ID NO:24, SEQ ID NO:26, SEQ ID NO:28, SEQ ID NO:32, or SEQ ID NO:44. LMPs containing a protein kinase domain include those shown in SEQ ID NO:36, SEQ ID NO:38, SEQ ID NO:48, SEQ ID NO:22 or SEQ ID NO:16. LMPs containing a signal transduction domain include those shown in SEQ ID NO:2, SEQ ID NO:14, SEQ ID NO:34, SEQ ID NO:40, SEQ ID NO:42 or SEQ ID NO:46. LMPs containing a protease domain include those shown in SEQ ID NO:6 or SEQ ID NO:12. LMPs containing a carbohydrate metabolism domain include those shown in SEQ ID NO:10, SEQ ID NO:18 or SEQ ID NO:30.

In another preferred embodiment, an isolated nucleic acid molecule of the invention comprises a nucleic acid molecule which is a complement of any of the nucleic acid sequences disclosed herein, including one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47, or a portion thereof. As used herein, the term "complementary" refers to a nucleotide sequence that can hybridize to one of the nucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47, thereby forming a stable duplex.

In another preferred embodiment, an isolated nucleic acid of the invention comprises a polynucleotide sequence encoding a polypeptide selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48.

In still another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in the Figures, or a portion thereof. In an additional preferred embodiment, an isolated nucleic acid molecule of the invention comprises a nucleotide sequence which hybridizes, e.g., hybridizes under stringent conditions, to one of the nucleotide sequences shown in the Figures, or a portion thereof. These hybridization conditions include washing with a solution having a salt concentration of about 0.02 molar at pH 7 at about 60° C.

Moreover, the nucleic acid molecule of the invention can comprise only a portion of the coding region of one of the sequences in the Figures, for example a fragment which can be used as a probe or primer or a fragment encoding a biologically active portion of a LMP. The nucleotide sequences determined from the cloning of the LMP genes from *Arabidopsis thaliana* allows for the generation of probes and primers designed for use in identifying and/or cloning LMP homologues in other cell types and organisms, as well as LMP homologues from other plants or related species. Therefore this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in the Figures, an anti-sense sequence of one of the sequences set forth in the Figures, or naturally occurring mutants thereof. Primers based on a nucleotide sequence of the Figures can be used in PCR reactions to clone LMP homologues. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a LMP, such as by measuring a level of a LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to an amino acid encoded by a sequence of the Figures such that the protein or portion thereof maintains the same or a similar function as the wild-type protein. As used herein, the language "sufficiently homologous" refers to proteins or portions thereof which have amino acid sequences which include a minimum number of identical or equivalent (e.g., an amino acid residue which has a similar side chain as an amino acid residue in one of the ORFs of a sequence of the Figures) amino acid residues to an amino acid sequence such that the protein or portion thereof is able to participate in the metabolism of compounds necessary for the production of seed storage compounds in plants, construction of cellular membranes in microorganisms or plants, or in the transport of molecules across these membranes. Regulatory proteins, such as DNA binding proteins, transcription factors, kinases, phosphatases, or protein members of metabolic pathways such as the lipid, starch and protein biosynthetic pathways, or membrane transport systems, may play a role in the biosynthesis of seed storage compounds. Examples of such activities are described herein (see putative annotations in Table 4). Examples of LMP-encoding nucleic acid sequences are set forth in the Figures.

As altered or increased sugar and/or fatty acid production is a general trait wished to be inherited into a wide variety of plants like maize, wheat, rye, oat, triticale, rice, barley, soybean, peanut, cotton, rapeseed, canola, *manihot*, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut) and perennial grasses and forage crops, these crop plants are also preferred target plants for genetic engineering as one further embodiment of the present invention.

Portions of proteins encoded by the LMP nucleic acid molecules of the invention are preferably biologically active portions of one of the LMPs. As used herein, the term "biologically active portion of a LMP" is intended to include a portion, e.g., a domain/motif, of a LMP that participates in the metabolism of compounds necessary for the biosynthesis of seed storage lipids, or the construction of cellular membranes in microorganisms or plants, or in the transport of molecules across these membranes, or has an activity as set forth in Table 3. To determine whether a LMP or a biologically active portion thereof can participate in the metabolism of compounds necessary for the production of seed storage compounds and cellular membranes, an assay of enzymatic activity may be performed. Such assay methods are well known to those skilled in the art, and as described in Example 14 of the Exemplification.

Biologically active portions of a LMP include peptides comprising amino acid sequences derived from the amino acid sequence of a LMP (e.g., an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48 or the amino acid sequence of a protein homologous to a LMP, which include fewer amino acids than a full length LMP or the full length protein which is homologous to a LMP) and exhibit at least one activity of a LMP. Typically, biologically active portions (peptides, e.g., peptides which are, for example, 5, 10, 15, 20, 25, 30, 35, 36, 37, 38, 39, 40, 50, 100 or more amino acids in length) comprise a domain or motif with at least one activity of a LMP. Moreover, other biologically active portions, in which other regions of the protein are deleted, can be prepared by recombinant techniques and evaluated for one or more of the activities described herein. Preferably, the biologically active portions of a LMP include one or more selected domains/motifs or portions thereof having biological activity.

Additional nucleic acid fragments encoding biologically active portions of a LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from one of the polynucleotide sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47 (and portions thereof) due to degeneracy of the genetic code and thus encode the same LMP as that encoded by the nucleotide sequences shown in the Figures. In a further embodiment, the nucleic acid molecule of the invention encodes a full length protein which is substantially homologous to an amino acid sequence of a polypeptide encoded by an open reading frame shown in the Figures. In one embodiment, the full-length nucleic acid or protein or fragment of the nucleic acid or protein is from *Arabidopsis thaliana*.

In addition to the *Arabidopsis thaliana* LMP nucleotide sequences described herein, it will be appreciated by those skilled in the art that DNA sequence polymorphisms that lead to changes in the amino acid sequences of LMPs may exist within a population (e.g., the *Arabidopsis thaliana* population). Such genetic polymorphism in the LMP gene may exist among individuals within a population due to natural variation. As used herein, the terms "gene" and "recombinant gene" refer to nucleic acid molecules comprising an open reading frame encoding a LMP, preferably a *Arabidopsis thaliana* LMP. Such natural variations can typically result in 1-40% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-*Arabidopsis thaliana* orthologs of the *Arabidopsis thaliana* LMP cDNA of the invention can be isolated based on their homology to *Arabidopsis thaliana* LMP nucleic acid disclosed herein using the *Arabidopsis thaliana* cDNA, or a portion thereof, as a hybridization probe according to standard hybridization techniques under stringent hybridization conditions. As used herein, the term "orthologs" refers to two nucleic acids from different species, but that have evolved from a common ancestral gene by speciation. Normally, orthologs encode proteins having the same or similar functions. Accordingly, in another embodiment, an isolated nucleic acid molecule of the invention is at least 15 nucleotides in length and hybridizes under stringent conditions to the nucleic acid molecule comprising a nucleotide sequence of the Figures. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, N.Y. (1989) 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a polynucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45 or SEQ ID NO:47 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Arabidopsis thaliana* LMP.

In addition to naturally-occurring variants of the LMP sequence that may exist in the population, the skilled artisan will further appreciate that changes can be introduced by mutation into a nucleotide sequence of the Figures, thereby leading to changes in the amino acid sequence of the encoded LMP, without altering the functional ability of the LMP. For example, nucleotide substitutions leading to amino acid substitutions at "non-essential" amino acid residues can be made in a a LMP polynucleotide sequence. A "non-essential" amino acid residue is a residue that can be altered from the wild-type sequence of one of the LMPs provided herein without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein. In one embodiment, the isolated nucleic acid molecule comprises a nucleotide sequence encoding a protein, wherein the protein comprises an amino acid sequence at least about 50% homologous to an amino acid sequence encoded by a nucleic acid of the Figures and is capable of participation in the metabolism of compounds necessary for the production of seed storage compounds in *Arabidopsis thaliana*, or cellular membranes, or has one or more activities set forth in Table 4. Preferably, the protein encoded by the nucleic acid molecule is at least about 50-60% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48, more preferably at least about 60-70% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48, even more preferably at least about 70-80%, 80-90%, 90-95% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48, and most preferably at least about 96%, 97%, 98%, or 99% homologous as shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48.

To determine the percent homology of two amino acid sequences (e.g., the sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48) is occupied by the same amino acid residue or nucleotide as the corresponding position in the other sequence (e.g., a mutant or homolog of the sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 or SEQ ID NO:48), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An isolated nucleic acid molecule encoding a LMP homologous to a protein sequence encoded by a nucleic acid of the Figures can be created by introducing one or more nucleotide substitutions, additions or deletions into a nucleotide sequence of the Figures such that one or more amino acid substitutions, additions or deletions are introduced into the encoded protein. Mutations can be introduced into one of the sequences of the Figures by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a LMP is preferably replaced with another amino acid residue from the same side chain family. Alternatively, in another embodiment, mutations can be introduced randomly along all or part of a LMP coding sequence, such as by saturation mutagenesis, and the resultant mutants can be screened for a LMP activity described herein to identify mutants that retain LMP activity. Following mutagenesis of one of the sequences of the Figures, the encoded protein can be expressed recombinantly and the activity of the protein can be determined using, for example, assays described herein (see Examples 9, 13,-14 of the Exemplification).

LMPs are preferably produced by recombinant DNA techniques. For example, a nucleic acid molecule encoding the protein is cloned into an expression vector (as described above), the expression vector is introduced into a host cell (as described herein) and the LMP is expressed in the host cell. The LMP can then be isolated from the cells by an appropriate purification scheme using standard protein purification techniques. Alternative to recombinant expression, a LMP or peptide thereof can be synthesized chemically using standard peptide synthesis techniques. Moreover, native LMP can be isolated from cells, for example using an anti-LMP antibody, which can be produced by standard techniques utilizing a LMP or fragment thereof of this invention.

The invention also provides LMP chimeric or fusion proteins. As used herein, a LMP "chimeric protein" or "fusion protein" comprises a LMP polypeptide operatively linked to a non-LMP polypeptide. An "LMP polypeptide" refers to a polypeptide having an amino acid sequence corresponding to a LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. Within the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP (glutathione S-transferase) fusion protein in which the LMP sequences are fused to the C-terminus of the GST sequences. Such fusion proteins can facilitate the purification of recombinant LMPs. In another embodiment, the fusion protein is a LMP containing a heterologous signal sequence at its N-terminus. In certain host cells (e.g., mammalian host cells), expression and/or secretion of a LMP can be increased through use of a heterologous signal sequence.

Preferably, a LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding a LMP. The term "coding region" refers to the region of the nucleotide sequence comprising codons which are translated into amino acid residues (e.g., the entire coding region of Pk002b comprises nucleotides 1 to 2050). In another embodiment, the antisense nucleic acid molecule is antisense to a "noncoding region" of the coding strand of a nucleotide sequence encoding LMP. The term "noncoding region" refers to 5' and 3' sequences which flank the coding region that are not translated into amino acids (i.e., also referred to as 5' and 3' untranslated regions).

Given the coding strand sequences encoding LMP disclosed herein (e.g., the sequences set forth in the Figures), antisense nucleic acids of the invention can be designed according to the rules of Watson and Crick base pairing. The antisense nucleic acid molecule can be complementary to the entire coding region of LMP mRNA, but more preferably is an oligonucleotide which is antisense to only a portion of the coding or noncoding region of LMP mRNA. For example, the antisense oligonucleotide can be complementary to the region surrounding the translation start site of LMP mRNA. An antisense oligonucleotide can be, for example, about 5, 10, 15, 20, 25, 30, 35, 40, 45 or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydro-uracil, beta-D-galactosylqueosine, inosine, N-6-isopentenyladenine, 1-methylguanine, 1-methylinosine, 2,2-dimethylguanine, 2-in ethyladenine, 2-methylguanine, 3-methylcytosine, 5-methyl-cytosine, N-6-adenine, 7-methylguanine, 5-methylaminomethyluracil, 5-methoxyamino-methyl-2-thiouracil, beta-D-mannosylqueosine, 5'-methoxycarboxymethyl-uracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diamino-purine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand interfering RNA construct can be used to cause a down-regulation of the LMP mRNA level and LMP activity in transgenic plants. This requires transforming the plants with a chimeric construct containing a portion of the LMP sequence in the sense orientation fused to the antisense sequence of the same portion of the LMP sequence. A DNA linker region of variable length can be used to separate the sense and antisense fragments of LMP sequences in the construct.

The antisense nucleic acid molecules of the invention are typically administered to a cell or generated in situ such that they hybridize with or bind to cellular mRNA and/or genomic DNA encoding a LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. 1987, Nucleic Acids Res. 15:6625-6641). The antisense nucleic acid molecule can also comprise a 2'-o-methylribonucleotide (Inoue et al. 1987, Nucleic Acids Res. 15:6131-6148) or a chimeric RNA-DNA analogue (Inoue et al. 1987, FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff & Gerlach 1988, Nature 334:585-591)) can be used to catalytically cleave LMP mRNA transcripts to thereby inhibit translation of LMP mRNA. A ribozyme having specificity for a LMP-encoding nucleic acid can be designed based upon the nucleotide sequence of a LMP cDNA disclosed herein (i.e., Pk002b in the Figures) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a LMP-encoding mRNA (see, e.g., Cech et al., U.S. Pat. No. 4,987,071 and Cech et al., U.S. Pat. No. 5,116,742). Alternatively, LMP mRNA can be used to select a catalytic RNA having a specific ribonuclease activity from a pool of RNA molecules (see, e.g., Bartel, D. & Szostak J. W. 1993, Science 261:1411-1418).

Alternatively, LMP gene expression can be inhibited by targeting nucleotide sequences complementary to the regulatory region of a LMP nucleotide sequence (e.g., a LMP promoter and/or enhancers) to form triple helical structures that prevent transcription of a LW gene in target cells (See generally, Helene C. 1991, Anticancer Drug Des. 6:569-84; Helene C. et al. 1992, Ann. N.Y. Acad. Sci. 660:27-36; and Maher, L. J. 1992, Bioassays 14:807-15).

Another aspect of the invention pertains to vectors, preferably expression vectors, containing a nucleic acid encoding a LMP (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used inter-changeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnolgy, CRC Press, Boca Raton, Fla., eds.: Glick & Thompson, Chapter 7, 89-108 including the references therein. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells (using baculovirus expression vectors), yeast and other fungal cells (see Romanos M. A. et al. 1992, Foreign gene expression in yeast: a review, Yeast 8:423-488; van den Hondel, C. A. M. J. J. et al. 1991, Heterologous gene expression in filamentous fungi, in: More Gene Manipulations in Fungi, Bennet & Lasure, eds., p. 396-428:Academic Press: an Diego; and van den Hondel & Punt 1991, Gene transfer systems and vector development for filamentous fungi, in: Applied Molecular Genetics of Fungi, Peberdy et al., eds., p. 1-28, Cambridge University Press: Cambridge), algae (Falciatore et al. 1999, Marine Biotechnology 1:239-251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and *Stylonychia*, especially of the genus *Stylonychia lemnae* with vectors following a transformation method as described in WO 98/01572 and multicellular plant cells (see Schmidt & Willmitzer 1988, High efficiency *Agrobacterium tumefaciens*-mediated transformation of *Arabidopsis thaliana* leaf and cotyledon plants, Plant Cell Rep.:583-586); Plant Molecular Biology and Biotechnology, C Press, Boca Raton, Fla., chapter 6/7, S.71-119 (1993); White, Jenes et al., Techniques for Gene Transfer, in: Transgenic Plants, Vol. 1, Engineering and Utilization, eds.: Kung and Wu, Academic Press 1993, 128-43; Potrykus 1991, Annu. Rev. Plant Physiol. Plant Mol. Biol. 42:205-225 (and references cited therein) or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith & Johnson 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al. 1988, Gene 69:301-315) and pET 1 ld (Studier et al. 1990, Gene Expression Technology:Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman S. 1990, Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al. 1992, Nucleic Acids Res. 20:2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec 1 (Baldari et al. 1987, EMBO J. 6:229-234), pMFa (Kurjan & Herskowitz 1982, Cell 30:933-943), pJRY88 (Schultz et al. 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt 1991, "Gene transfer systems and vector development for filamentous fungi, in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf 9 cells) include the pAc series (Smith et al. 1983, Mol. Cell. Biol. 3:2156-2165) and the pVL series (Lucklow & Summers 1989, Virology 170:31-39).

In yet another embodiment, a nucleic acid of the invention is expressed in mammalian cells using a mammalian expression vector. Examples of mammalian expression vectors include pCDM8 (Seed 1987, Nature 329:840) and pMT2PC (Kaufman et al. 1987, EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, Fritsh and Maniatis, Molecular Cloning: A Laboratoiy Manual. 2nd, ed., Cold Spring Harbor Laboratoiy, Cold Spring Harbor Laboratory Press, Cold Spring Harbor, N.Y., 1989.

In another embodiment, the LMPs of the invention may be expressed in uni-cellular plant cells (such as algae, see Falciatore et al. (1999, Marine Biotechnology 1:239-251 and references therein) and plant cells from higher plants (e.g., the spermatophytes, such as crop plants)). Examples of plant expression vectors include those detailed in: Becker, Kemper, Schell and Masterson (1992, "New plant binary vectors with selectable markers located proximal to the left border", Plant Mol. Biol. 20:1195-1197) and Bevan (1984, "Binary *Agrobacterium* vectors for plant transformation, Nucleic Acids Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38).

A plant expression cassette preferably contains regulatory sequences capable to drive gene expression in plant cells and which are operably linked so that each sequence can fulfill its function such as termination of transcription such as polyadenylation signals. Preferred polyadenylation signals are those originating from *Agrobacterium tumefaciens* t-DNA such as the gene 3 known as octopine synthase of the Ti-plasmid pTiACH5 (Gielen et al. 1984, EMBO J. 3:835) or functional equivalents thereof but also all other terminators functionally active in plants are suitable.

As plant gene expression is very often not limited on transcriptional levels a plant expression cassette preferably contains other operably linked sequences like translational enhancers such as the overdrive-sequence containing the 5'-untranslated leader sequence from tobacco mosaic virus enhancing the protein per RNA ratio (Gallie et al. 1987, Nucleic Acids Res. 15:8693-8711).

Plant gene expression has to be operably linked to an appropriate promoter conferring gene expression in a timely, cell or tissue specific manner. Preferred are promoters driving constitutive expression (Benfey et al. 1989, EMBO J. 8:2195-2202) like those derived from plant viruses like the 35S CAMV (Franck et al. 1980, Cell 21:285-294), the 19S CaMV (see also U.S. Pat. No. 5,352,605 and WO 84/02913) or plant promoters like those from Rubisco small subunit described in U.S. Pat. No. 4,962,028. Even more preferred are seed-specific promoters driving expression of LMP proteins during all or selected stages of seed development. Seed-specific plant promoters are known to those of ordinary skill in the art and are identified and characterized using seed-specific mRNA libraries and expression profiling techniques. Seed-specific promoters include the napin-gene promoter from rapeseed (U.S. Pat. No. 5,608,152), the USP-promoter from *Vicia faba* (Baeumlein et al. 1991, Mol. Gen. Genetics 225:459-67), the oleosin-promoter from *Arabidopsis* (WO 98/45461), the phaseolin-promoter from *Phaseolus vulgaris* (U.S. Pat. No. 5,504,200), the Bce4-promoter from *Brassica* (WO9113980) or the legumin B4 promoter (LeB4; Baeumlein et al. 1992, Plant J. 2:233-239) as well as promoters conferring seed specific expression in monocot plants like maize, barley, wheat, rye, rice etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the *Sorghum kasirin*-gene, the rye secalin gene).

Plant gene expression can also be facilitated via an inducible promoter (for review see Gatz 1997, Annu. Rev. Plant Physiol. Plant Mol. Biol. 48:89-108). Chemically inducible promoters are especially suitable if gene expression is desired in a time specific manner. Examples for such promoters are a salicylic acid inducible promoter (WO 95/19443), a tetracycline inducible promoter (Gatz et al. 1992, Plant J. 2:397-404) and an ethanol inducible promoter (WO 93/21334).

Promoters responding to biotic or abiotic stress conditions are also suitable promoters such as the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375091).

Other preferred sequences for use in plant gene expression cassettes are targeting-sequences necessary to direct the gene-product in its appropriate cell compartment (for review see Kermode 1996, Crit. Rev. Plant Sci. 15:285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Also especially suited are promoters that confer plastid-specific gene expression, as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner, which allows for expression (by transcription of the DNA molecule) of an RNA molecule, which is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a LMP can be expressed in bacterial cells, insect cells, fungal cells, mammalian cells (such as Chinese hamster ovary cells (CHO) or COS cells), algae, ciliates or plant cells. Other suitable host cells are known to those skilled in the art.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, *Molecular Cloning: A Laboratory Manual. 2nd, ed., Cold Spring Harbor Laboratory*, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, kanamycin and methotrexate or in plants that confer resistance towards an herbicide such as glyphosate or glufosinate. A nucleic acid encoding a selectable marker can be introduced into a host cell on the same vector as that encoding a LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of a LMP gene into which a deletion, addition or substitution has been introduced to thereby alter, e.g., functionally disrupt, the LMP gene. Preferably, this LMP gene is an *Arabidopsis thaliana* LMP gene, but it can be a homologue from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as ehimeraplasty (Cole-Strauss et al. 1999, Nucleic Acids Res. 27:1323-1330 and Kmiec 1999, American Scientist 87:240-247). Homologous recombination procedures in *Arabidopsis thaliana* are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous LMP gene carried by the vector and an endogenous LMP gene in a microorganism or plant. The additional flankinLMP nucleic acid is of sufficient length for successful homologous recombination with the endogenous gene. Typically, several hundreds of base pairs up to kilobases of flanking DNA (both at the 5' and 3' ends) are included in the vector (see e.g., Thomas & Capecchi 1987, Cell 51:503, for a description of homologous recombination vectors). The vector is introduced into a microorganism or plant cell (e.g., via polyethyleneglycol mediated DNA). Cells in which the introduced LMP gene has homologously recombined with the endogenous LMP gene are selected using art-known techniques.

In another embodiment, recombinant microorganisms can be produced which contain selected systems which allow for regulated expression of the introduced gene. For example, inclusion of a LMP gene on a vector placing it under control of the lac operon permits expression of the LMP gene only in the presence of IPTG. Such regulatory systems are well known in the art.

A host cell of the invention, such as a prokaryotic or eukaryotic host cell in culture can be used to produce (i.e., express) a LMP. Accordingly, the invention further provides methods for producing LMPs using the host cells of the invention. In one embodiment, the method comprises culturing a host cell of the invention (into which a recombinant expression vector encoding a LMP has been introduced, or which contains a wild-type or altered LMP gene in it's genome) in a suitable medium until LMP is produced. Tn another embodiment, the method further comprises isolating LMPs from the medium or the host cell.

Another aspect of the invention pertains to isolated LMPs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals which are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, an *Arabidopsis thaliana* LMP in other plants than *Arabidopsis thaliana* or microorganisms, algae or fungi.

An isolated LMP or a portion thereof of the invention can participate in the metabolism of compounds necessary for the production of seed storage compounds in *Arabidopsis thaliana*, or of cellular membranes, or has one or more of the activities set forth in Table 4. In preferred embodiments, the protein or portion thereof comprises an amino acid sequence which is sufficiently homologous to an amino acid sequence encoded by a nucleic acid of the Figures such that the protein or portion thereof maintains the ability to participate in the metabolism of compounds necessary for the construction of cellular membranes in *Arabidopsis thaliana*, or in the transport of molecules across these membranes. The portion of the protein is preferably a biologically active portion as described herein. In another preferred embodiment, a LMP of the invention has an amino acid sequence encoded by a nucleic acid of the Figures. In yet another preferred embodiment, the LMP has an amino acid sequence which is encoded by a nucleotide sequence which hybridizes, e.g., hybridizes under stringent conditions, to a nucleotide sequence of the Figures. In still another preferred embodiment, the LMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99% or more homologous to one of the amino acid sequences encoded by a nucleic acid of the Figures. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to a nucleotide sequence of the Figures, and which can participate in the metabolism of compounds necessary for the construction of cellular membranes in *Arabidopsis thaliana*, or in the transport of molecules across these membranes, or which has one or more of the activities set forth in Table 4.

In other embodiments, the LMP is substantially homologous to an amino acid sequence encoded by a nucleic acid of the Figures and retains the functional activity of the protein of one of the sequences encoded by a nucleic acid of the Figures yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence and which has at least one of the LMP activities described herein. In another embodiment, the invention pertains to a full *Arabidopsis thaliana* protein which is substantially homologous to an entire amino acid sequence encoded by a nucleic acid of the Figures.

Homologues of the LMP can be generated by mutagenesis, e.g., discrete point mutation or truncation of the LMP. As used herein, the term "homologue" refers to a variant form of the LMP which acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP, by, for example, competitively binding to a downstream or upstream member of the cell membrane component metabolic cascade which includes the LMP, or by binding to a LMP which mediates transport of compounds across such membranes, thereby preventing translocation from taking place.

In an alternative embodiment, homologues of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods which can be used to produce libraries of potential LMP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (see, e.g., Narang 1983, Tetrahedron 39:3; Itakura et al. 1984, Annu. Rev. Biochem. 53:323; Itakura et al. 1984, Science 198:1056; Ike et al. 1983, Nucleic Acids Res. 11:477).

In addition, libraries of fragments of the LMP coding sequences can be used to generate a variegated population of LMP fragments for screening and subsequent selection of homologues of a LMP. In one embodiment, a library of coding sequence fragments can be generated by treating a double stranded PCR fragment of a LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LMP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LMP homologues (Arkin & Yourvan 1992, Proc. Natl. Acad. Sci. USA 89:7811-7815; Delgrave et al. 1993, Protein Engineering 6:327-331).

In another embodiment, cell based assays can be exploited to analyze a variegated LMP library, using methods well known in the art.

The nucleic acid molecules, proteins, protein homologues, fusion proteins, primers, vectors, and host cells described herein can be used in one or more of the following methods: identification of *Arabidopsis thaliana* and related organisms; mapping of genomes of organisms related to *Arabidopsis thaliana*; identification and localization of *Arabidopsis thaliana* sequences of interest; evolutionary studies; determination of LMP regions required for function; modulation of a LMP activity; modulation of the metabolism of one or more cell functions; modulation of the transmembrane transport of one or more compounds; and modulation of seed storage compound accumulation.

The plant *Arabidopsis thaliana* represents one member of higher (or seed) plants. It is related to other plants such as *Brassica napus* or soybean which require light to drive photosynthesis and growth. Plants like *Arabidopsis thaliana* and *Brassica napus* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of *Arabidopsis* genomes, or of genomes of related organisms.

The LMP nucleic acid molecules of the invention have a variety of uses. First, they may be used to identify an organism as being *Arabidopsis thaliana* or a close relative thereof. Also, they may be used to identify the presence of *Arabidopsis thaliana* or a relative thereof in a mixed population of microorganisms. The invention provides the nucleic acid sequences of a number of *Arabidopsis thaliana* genes; by probing the extracted genomic DNA of a culture of a unique or mixed population of microorganisms under stringent conditions with a probe spanning a region of an *Arabidopsis thaliana* gene which is unique to this organism, one can ascertain whether this organism is present.

Further, the nucleic acid and protein molecules of the invention may serve as markers for specific regions of the genome. This has utility not only in the mapping of the genome, but also for functional studies of *Arabidopsis thaliana* proteins. For example, to identify the region of the genome to which a particular *Arabidopsis thaliana* DNA-binding protein binds, the *Arabidopsis thaliana* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Arabidopsis thaliana*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related plants.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of a LMP of the invention may directly affect the accumulation of seed storage compounds. In the case of plants expressing LMPs, increased transport can lead to altered accumulation of compounds and/or solute partitioning within the plant tissue and organs which ultimately could be used to affect the accumulation of one or more seed storage compounds during seed development. An example is provided by Mitsukawa et al. (1997, Proc. Natl. Acad. Sci. USA 94:7098-7102), where over expression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al. 2000, Plant J. 24:383-396) and the lipid composition in leaves and roots (Bartel et al. 2000, Proc. Natl. Acad. Sci. USA 97:10649-10654). Likewise, the activity of the plant ACCase has been demonstrated to be regulated by phosphorylation (Savage & Ohlrogge 1999, Plant J. 18:521-527) and alterations in the activity of the kinases and phosphatases (LMPs) that act on the ACCase could lead to increased or decreased levels of seed lipid accumulation. Moreover, the presence of lipid kinase activities in chloroplast envelope membranes suggests that signal transduction pathways and/or membrane protein regulation occur in envelopes (see, e.g., Müller et al. 2000, J. Biol. Chem. 275:19475-19481 and literature cited therein). The ABI1 and ABI2 genes encode two protein serine/threonine phosphatases 2C, which are regulators in abscisic acid signaling pathway, and thereby in early and late seed development (e.g. Merlot et al. 2001, Plant J. 25:295-303). For more examples see also the section 'background of the invention'.

The present invention also provides antibodies which specifically binds to an LMP-polypeptide, or a portion thereof, as encoded by a nucleic acid disclosed herein or as described herein.

Antibodies can be made by many well-known methods (see, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then be fused with an immortal cell line and screened for antibody secretion. The antibodies can be used to screen nucleic acid clone libraries for cells secreting the antigen. Those positive clones can then be sequenced (see, for example, Kelly et al. 1992, Bio/Technology 10:163-167; Bebbington et al. 1992, Bio/Technology 10:169-175).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes a) General Cloning Processes:

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics", Cold Spring Harbor Laboratory Press: ISBN 0-87969-451-3).

b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg) and Sigma (Deisenhofen). Solutions were prepared using purified, pyrogen-free water, designated as $H_2O$ in the following text, from a Milli-Q water system water purification plant (Millipore, Eschborn). Restriction endonucleases, DNA-modifying enzymes and molecular biology kits were obtained from the companies AGS (Heidelberg), Amersham (Braunschweig), Biometra (Gottingen), Boehringer (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.

c) Plant Material:

For this study, in one series of experiments, root material of wild-type and pickle mutant plants of *Arabidopsis thaliana* were used. The pkl mutation was isolated from an ethyl methanesulfonate-mutagenized population of the Columbia ecotype as described (Ogas et al. 1997, Science 277:91-94; Ogas et al. 1999, Proc. Natl. Acad. Sci. USA 96:13839-13844). In other series of experiments, siliques of individual ecotypes of *Arabidopsis thaliana* and of selected *Arabidopsis* phytohormone mutants were used. Seeds were obtained from the *Arabidopsis* stock center.

d) Plant Growth:

Plants were either grown on Murashige-Skoog medium as described in Ogas et al. (1997, Science 277:91-94; 1999, Proc. Natl. Acad. Sci. USA 96:13839-13844) or on soil under standard conditions as described in Focks & Benning (1998, Plant Physiol. 118:91-101).

Example 2

Total DNA Isolation from Plants

The details for the isolation of total DNA relate to the working up of one gram fresh weight of plant material.

CTAB buffer: 2% (w/v) N-cethyl-N,N,N-trimethylammonium bromide (CTAB); 100 mM Tris HCl pH 8.0; 1.4 M NaCl; 20 mM EDTA. N-Laurylsarcosine buffer:10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosinc buffer, 20 μl of β-mercaptoethanol and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000 g and RT for 15 min in each case. The DNA was then precipitated at −70° C. for 30 min using ice-cold isopropanol. The precipitated DNA was sedimented at 4° C. and 10,000 g for 30 mM and resuspended in 180 μl al of TE buffer (Sambrook et al. 1989, Cold Spring Harbor Laboratory Press: ISBN 0-87969-309-6). For further purification, the DNA was treated with NaCl (1.2 M final concentration) and precipitated again at −70° C. for 30 min using twice the volume of absolute ethanol. After a washing step with 70% ethanol, the DNA was dried and subsequently taken up in 50 μl of $H_2O$+RNAse (50 mg/ml final concentration). The DNA was dissolved overnight at 4° C. and the RNAse digestion was subsequently carried out at 37° C. for 1 h. Storage of the DNA took place at 4° C.

Example 3

Isolation of Total RNA and poly-(A)+ RNA from Plants

For the investigation of transcripts, both total RNA and poly-(A)±RNA were isolated.

RNA is isolated from siliques of *Arabidopsis* plants according to the following procedure:

RNA preparation from *Arabidopsis* seeds—"hot" extraction:

1. Buffers, enzymes and solution

2M KCl

Proteinase K

Phenol (for RNA)

Chloroform:Isoamylalcohol (Phenol:choloroform 1:1; pH adjusted for RNA)

4 M LiCl, DEPC-treated

DEPC-treated water

3M NaOAc, pH 5, DEPC-treated

Isopropanol

70% ethanol (made up with DEPC-treated water)

Resuspension buffer:0.5% SDS, 10 mM Tris pH 7.5, 1 mM EDTA made up with DEPC-treated water as this solution can not be DEPC-treated Extraction Buffer:

0.2M Na Borate 30 mM EDTA 30 mM EGTA

1% SDS (250 μl of 10% SDS-solution for 2.5 ml buffer)

1% Deoxycholate (25 mg for 2.5 ml buffer)

2% PVPP (insoluble −50 mg for 2.5 ml buffer)

2% PVP 40K (50 mg for 2.5 ml buffer)

10 mM DTT 100 mM ☐-Mercaptoethanol (fresh, handle under fume hood—use 35 μl of 14.3M solution for 5 ml buffer)

2. Extraction

Heat extraction buffer up to 80° C. Grind tissue in liquid nitrogen-cooled mortar, transfer tissue powder to 1.5 ml tube. Tissue should kept frozen until buffer is added so transfer the sample with pre-cooled spatula and keep the tube in liquid nitrogen all time. Add 350 μpreheated extraction buffer (here for 100 mg tissue, buffer volume can be as much as 500 μl for bigger samples) to tube, vortex and heat tube to 80° C. for ~1 min. Keep then on ice. Vortex sample, grind additionally with electric mortar.

3. Digestion

Add Proteinase K (0.15 mg/100 mg tissue), vortex and keep at 37° C. for one hour.

4. First Purification

Add 27 μl 2M KCl. Chill on ice for 10 min. Centrifuge at 12.000 rpm for 10 minutes at room temperature. Transfer supernatant to fresh, RNAase-free tube and do one phenol extraction, followed by a choloroform:isoamylalcohol extraction. Add 1 vol. isopropanol to supernatant and chill on ice for 10 min. Pellet RNA by centrifugation (7000 rpm for 10 min at RT). Resolve pellet in 1 ml 4M LiCl by 10 to 15 min vortexing. Pellet RNA by 5 min centrifugation.

5. Second Purification

Resuspend pellet in 500 μl Resuspension buffer. Add 5000 phenol and vortex. Add 250 μl ehloroform:isoamylalcohol and vortex. Spin for 5 min. and transfer supernatant to fresh tube. Repeat choloform:isoamylalcohol extraction until interface is clear. Transfer supernatant to fresh tube and add 1/10 vol 3M NaOAc, pH 5 and 6000 isopropanol. Keep at −20 for 20 min or longer. Pellet RNA by 10 min centrifugation. Wash pellet once with 70% ethanol. Remove all remaining alcohol before resolving pellet with 15 to 20 μl DEPC-water. Determine quantity and quality by measuring the absorbance of a 1:200 dilution at 260 and 280 nm. 40 μg RNA/ml=1OD260

RNA from roots of wild-type and the pickle mutant of Arabidopsis is isolated as described (Ogas et al. 1997, Science 277:91-94; Ogas et al. 1999, Proc. Natl. Acad. Sci. USA 96:13839-13844).

The mRNA is prepared from total RNA, using the Amersham Pharmacia Biotech mRNA purification kit, which utilizes oligo(dT)-cellulose columns.

Isolation of Poly-(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

Example 4 cDNA Library Construction

For cDNA library construction, first strand synthesis was achieved using Murine Leukemia Virus reverse transcriptase (Roche, Mannheim, Germany) and oligo-d(T)-primers, second strand synthesis by incubation with DNA polymerase 1, Klenow enzyme and RNAseH digestion at 12° C. (2 h), 16° C. (1 h) and 22° C. (1 h). The reaction was stopped by incubation at 65° C. (10 min) and subsequently transferred to ice. Double stranded DNA molecules were blunted by T4-DNA-polymerase (Roche, Mannheim) at 37° C. (30 min). Nucleotides were removed by phenol/chloroform extraction and Sephadex G50 spin columns. EcoR_I adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 min). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 5

Identification of LMP Genes of Interest

The pickle Arabidopsis mutant was used to identify LMP-encoding genes. The pickle mutant accumulates seed storage compounds, such as seed storage lipids and seed storage proteins, in the root tips (Ogas et al. 1997, Science 277:91-94; Ogas et al. 1999, Proc. Natl. Acad. Sci. USA 96:13839-13844). mRNA isolated from roots of wild-type and pickle plants was used to create a subtracted and normalized cDNA library (SSH library) containing cDNAs that are only present in the pickle roots, but not in the wild-type roots. Clones from the SSH library were spotted onto nylon membranes and hybridized with radio-labeled pickle or wild-type root mRNA to ascertain that the SSH clones were more abundant in pickle roots compared to wild-type roots. These SSH clones were randomly sequenced and the sequences were annotated (see Example 9). Based on the expression levels and on these initial functional annotations (see Table 4), clones from the SSH library were identified as potential LMP-encoding genes.

Other LMP candidate genes were identified by selecting various Arabidopsis phytohormone mutants (e.g. obtained from EMS treatment) from the Arabidopsis stock center. These mutants and control wild-type plants were grown under standard conditions in growth chambers and screened for the accumulation of seed storage compounds. Mutants showing altered levels of seed storage lipids were considered as having a mutation in a LMP candidate gene and were investigated further. Table X3 contains the phytohormone mutants that showed the largest decrease in seed storage lipids. Based on our finding that some mutants had significantly decreased seed oil content we selected the respective wild-type allele or other enzymes in the same pathway as LMP-encoding genes (see table 4, sequence codes pk095, pk096, pk097, pk098, pk099, pk199, pk105 and pk107).

TABLE 3

Total fatty acid content in seeds of selected phytohormone mutants

| Allele | Phenotype | FA (g/g) Analysis of the first generation of seeds | FA (g/g) Analysis of the next generation of seeds |
|---|---|---|---|
| Ler-0 wild type | | 0.35 ± 0.02 | 0.35 ± 0.02 |
| abi1-1 (in Ler background) | ABA-insensitive | 0.33 ± 0.01 | 0.34 ± 0.02 |
| abi2-1 (in Ler background) | ABA-insensitive | 0.34 ± 0.03 | 0.37 ± 0.02 |
| abi3-1 (in Ler background) | ABA-insensitive | 0.29 ± 0.02 | 0.29 ± 0.02 |
| Col wild type | | 0.35 ± 0.02 | 0.35 ± 0.01 |
| axr2 (in Col background) | Auxin-resistant | 0.28 ± 0.02 | 0.28 ± 0.02 |
| etr1-1 (in Col background) | Ethylene-insensitive | 0.27 ± 0.03 | 0.29 ± 0.02 |
| ein5-1 (in Col background) | Ethylene-insensitive | 0.29 ± 0.03 | 0.30 ± 0.03 |
| Ein7 (in Col background) | Ethylene-insensitive | 0.29 ± 0.02 | 0.30 ± 0.01 |

TABLE 4

Putative LMP Functions

| Sequence code | Function | SEQ ID NO: |
|---|---|---|
| Pk002b | Hypothetical protein - *Arabidopsis thaliana* | 1 |
| Pk020b | Unknown protein - conserved hypothetical protein SPCC330.09 - *Schizosaccharomyces pombe* | 3 |
| Pk033 | Hypothetical protein - *A. thaliana* chromosome II BAC T08I13 genomic | 5 |
| Pk037 | 65 kDa regulatory subunit of protein phosphatase 2A, PP2A-A | 7 |
| Pk038 | Beta-1,3-glucanase class I precursor | 9 |
| Pk042a | ATP dependent copper transporter - *Arabidopsis* | 11 |
| Pk053b | unknown protein - *Arabidopsis thaliana* | 13 |
| Pk060 | Sequence of BAC T22H22 from *Arabidopsis thaliana* | 15 |
| Pk063b | putative malate dehydrogenase - *Arabidopsis thaliana* | 17 |
| Pk064 | late embryogenesis abundant protein - *Arabidopsis* | 19 |
| Pk073 | gene: "T18B16.210"; product : "putative protein" | 21 |
| Pk082 | Nucleic acid binding protein-like - *Arabidopsis thaliana* | 23 |
| Pk084a | *A. thaliana*, BAC F13K23.10, chromosome 1, | 25 |
| Pk086 | hypothetical protein A_IG002P16.9-*Arabidopsis thaliana* | 27 |
| Pk088b | putative nonspecific lipid-transfer protein precursor | 29 |
| Pk095 | *A. thaliana* AP2 domain family transcription factor homolog (ABI4) | 31 |
| Pk096 | *Arabidopsis thaliana* putative ethylene receptor (ETR2) | 33 |
| Pk097a | *Arabidopsis* ethylene-response gene ETR1 | 35 |
| Pk097b | *Arabidopsis* ethylene-response gene ETR1 like | 37 |
| Pk098 | *Arabidopsis thaliana* IAA17 (F19P19.31), auxin response gene | 39 |
| Pk099 | *A. thaliana* IAA7 (IAA7) gene, primary auxin-responsive genes | 41 |
| Pk100 | ABI3 gene; abscisic acid insensitive gene | 43 |
| Pk105 | protein phosphatase 2C involved in ABA signal (abi1) | 45 |
| Pk107 | regulation of ethylene response pathway (ctr1) | 47 |

TABLE 5

Grouping of LMPs based on Functional protein domains

| Functional category | SEQ ID: | SEQ Code: | Functional domain | Domain position |
|---|---|---|---|---|
| DNA-binding proteins | 4 | pk020b | HMG-I and HMG-Y DNA-binding domain (A + T-hook) | 206-226 |
| | 8 | pk037 | LexA DNA binding domain | 127-141 |
| | 8 | pk037 | STE-like transcription factor | 7-12 |
| | 20 | pk064 | DM DNA-binding domain | 201-240 |
| | 20 | pk064 | Histone H2B | 209-253 |
| | 24 | pk082 | HMG-I and HMG-Y DNA-binding domain (A + T-hook) | 174-192 |
| | 24 | pk082 | B-box zinc finger superfamily | 212-225 |
| | 26 | pk084a | HMG-I and HMG-Y DNA-binding domain (A + T-hook) | 8-30 |
| | 26 | pk084a | High mobility group proteins HMG1 and HMG2 | 11-35 |
| | 28 | pk086 | GATA-type zinc finger | 38-70 |
| | 32 | pk095 | Ethylene responsive element binding protein | 55-66, 77-93, 93-113, 119-140 |
| | 44 | pk100 | B3 DNA-binding domain | 37-47, 270-312, 457-473, 533-549, 565-598, 617-631 |
| Kinases | 36, 38 | pk097a, pk097b | His-kinase A | 351-360, 466-475, 511-519 |
| | 48 | pk107 | Protein kinase C-terminal domain | 666-700 |
| | 48 | pk107 | Tyrosine kinase catalytic domain | 714-752 |
| | 22 | pk073 | Shikimate kinase | 165-161 |
| | 22 | pk073 | Diacylglycerol kinase accessory domain | 138-161 |
| | 16 | pk060 | Glycerate kinase | 156-181 |
| Signal Transduction | 2 | pk002b | Troponin Ca2+ sensitive switch | 336-371 |
| | 2 | pk002b | HMG1 and HMG2 domain | 352-376 |
| | 14 | pk053b | Developmental signaling protein Wnt-1 family | 8-69 |
| | 34 | pk096 | Response regulator receiver domain | 697-710 |
| | 34 | pk096 | Inositol 1,4,5-triphosphate-binding protein receptor | 645-669 |
| | 40 | pk098 | AUX/IAA family domain | 7-22, 82-95, 112-143, 181-210 |
| | 42 | pk099 | AUX/IAA family domain | 6-21, 82-95, 126-157, 194-223 |
| | 46 | Pk105 | Protein phosphatase 2C family | 135-420 |
| Proteases | 6 | pk033 | DnaJ chaperonin central domain | 6-38 |
| | 6 | pk033 | ATP-dependent protease La (LON) domain | 535-569 |
| | 6 | pk033 | Protease-associated (PA) domain | 375-405 |
| | 12 | pk042a | Carboxypeptidase Taq metalloprotease signature | 176-196 |
| | 12 | pk042a | Gamma-glutamyltranspeptidase | 110-164 |
| | 12 | pk042a | E1-E2 ATPase | 127-156 |
| | 12 | pk042a | X-His dipeptidase (M25) signature | 3-20 |
| Carbohydrate metabolism | 10 | pk038 | Beta-1,3-glucanase, Glycoside hydrolase family 17 | 24-334 |
| | 18 | pk063b | Malic enzyme | 45-555 |
| | 30 | pk088b | Lipid transfer protein | 42-56, 70-95 |
| | 30 | pk088b | Cellulose-binding domain | 56-86 |
| | 30 | pk088b | Mannose-6-phosphate isomerase type II | 150-174 |
| | 30 | pk088b | Glyceraldehyde 3-phosphate dehydrogenase | 137-171 |

Classification of the proteins was done by Blasting against the BLOCKS database (S. Henikoff & J. G. Henikoff, "Protein family classification based on searching a database of blocks", Genomics 19: 97-107 (1994)).

Example 6

Cloning of Full-Length cDNAs and Binary Plasmids for Plant Transformation
RACE PCR to Determine Full-Length Sequences Full-length sequences of the *Arabidopsis thaliana* partial cDNAs (ESTs) that were identified in the SSH library and from MegaSort and MPSS EST sequencing in the *Arabidopsis thaliana* EST sequencing program using the annotation program EST-Max were isolated by RACE PCR using the SMART RACE cDNA amplification kit from Clontech allowing both 5'- and 3' rapid amplification of cDNA ends (RACE). The isolation of cDNAs and the RACE PCR protocol used were based on the manufacturer's conditions. The RACE product fragments were extracted from agarose gels with a QIAquick® Gel Extraction Kit (Qiagen) and ligated into the TOPO® pCR 2.1 vector (Invitrogen) following manufacturer's instructions. Recombinant vectors were transformed into TOP10 cells (Invitrogen) using standard conditions (Sambrook et al. 1989). Transformed cells are grown overnight at 37° C. on LB agar containing 50 μg/ml kanamycin and spread with 40 μl of a 40 mg/ml stock solution of X-gal in dimethylformamide for blue-white selection. Single white colonies are selected and used to inoculate 3 ml of liquid LB containing 50 μg/ml kanamycin and grown overnight at 37° C. Plasmid DNA was extracted using the QIAprep® Spin Miniprep Kit (Qiagen) following manufacturer's instructions. Subsequent analyses of clones and restriction mapping was performed according to standard molecular biology techniques (Sambrook et al. 1989). The sequences obtained from the RACE reactions were compiled to give the nucleotide sequences for the LMP genes (SEQ ID NOs: 1, 3, 5, 7, 9, 11, 13, 15, 17, 19, 21, 23, 25, 27, 29, 31, 33, 35, 37, 39, 41, 43, 45 and 47).

RT-PCR and Cloning of *Arabidopsis thaliana* LMP Genes

Full-length LMP cDNAs were isolated by RT-PCR from *Arabidopsis thaliana* RNA. The synthesis of the first strand cDNA was achieved using AMV Reverse Transcriptase (Roche, Mannheim, Germany). The resulting single-stranded cDNA was amplified via Polymerase Chain Reaction (PCR) utilizing two gene-specific primers. The conditions for the reaction were standard conditions with Expand High Fidelity PCR system (Roche). The parameters for the reaction were: five minutes at 94° C. followed by five cycles of 40 seconds at 94° C., 40 seconds at 50° C. and 1.5 minutes at 72° C. This was followed by thirty cycles of 40 seconds at 94° C., 40 seconds at 65° C. and 1.5 minutes at 72° C. The fragments generated under these RT-PCR conditions were analyzed by agarose gel electrophoresis to make sure that PCR products of the expected length had been obtained.

Full-length LMP cDNA were isolated by using synthetic oligonucleotide primers (MWG-Biotech) designed based on the LMP gene specific DNA sequence that was determined by EST sequencing and by sequencing of RACE PCR products. All 5' PCR primers ("forward primer", F) contained an AscI restriction site 5' upstream of the ATG start codon. All 3' PCR primers ("reverse primers", R) contained a PacT restriction site 3' downstream of the stop codon. The restriction sites were added so that the RT-PCR amplification products could be cloned into the AscI and PacT restriction sites located in the multiple cloning site of the binary vector pBPS-GB 1. The first 2 nucleotides are used as spacers so the restriction enzymes cut properly. The following "forward" (F) and "reverse" (R) primers were used to amplify the full-length *Arabidopsis thaliana* cDNAs by RT-PCR using RNA from *Physcomitrella* as original template:

```
For amplification of SEQ ID NO: 1
Pk002F
                                          (SEQ ID NO: 49)
(5'-ATGGCGCGCCATGGTTCGTCCTGGATTCATTATGC-3')

pk002R
                                          (SEQ ID NO: 50)
(5'-GCTTAATTAATCAGGCTTTGGATTTTACCGGGAC-3')

For amplification of SEQ ID NO: 3
pk020F
                                          (SEQ ID NO: 51)
(5'-ATGGCGCGCCGGGGAGGCCACCAAGAAAGTGCTG-3')

pk020R
                                          (SEQ ID NO: 52)
(5'-TCTTAATTAAGCTACATTTATCATTGCCGGCCTC-3')

For amplification of SEQ ID NO: 5
pk033F
                                          (SEQ ID NO: 53)
(5'-ATGGCGCGCCGAGCCGTTATTAGTTTTCATTCAAGGG-3')

pk033R
                                          (SEQ ID NO: 54)
(5'-AGTTAATTAATCTTAACTTACCAAGGAGCCGACAAA-3')

For amplification of SEQ ID NO: 7
pk037F
                                          (SEQ ID NO: 55)
(5'-ATTGGCGCGCCTGGTGTTGCAGTGATTTGATTC-3')

pk037R
                                          (SEQ ID NO: 56)
(3'-GCGTTAATTAAGCAGTTCATAGCCAGCAACCAA-5')

For amplification of SEQ ID NO: 9
pk038F
                                          (SEQ ID NO: 57)
(5'-ATGGCGCGCCATGACCACGTTATTCCTCCTTATTGC-3')

pk038R
                                          (SEQ ID NO: 58)
(5'-GCTTAATTAACATCACTCAACCGCCGTACCGTC-3')

For amplification of SEQ ID NO: 11
pk042F
                                          (SEQ ID NO: 59)
(5'-ATGGCGCGCCGGGCAAAGGCCATTGTCGAGT-3')

pk042R
                                          (SEQ ID NO: 60)
(5'-GCTTAATTAACCGGTACTCGGTTTAGTTCAATTT-3')

For amplification of SEQ ID NO: 13
pk053F
                                          (SEQ ID NO: 61)
(5'-ATGGCGCGCCCATGGATGTCTTGTTTCTCGATCTG-3')

pk053R
                                          (SEQ ID NO: 62)
(5'-GCTTAATTAAGATTTCTGACTTTGAATGGAAATGG-3')

For amplification of SEQ ID NO: 15
pk060F
                                          (SEQ ID NO: 63)
(5'-ATGGCGCGCCGAATCAGAAATTGGGCGAAGAAG-3')

pk060R
                                          (SEQ ID NO: 64)
(5'-GCTTAATTAACACAACAATCACTAGCTCAGAAGAGC-3')

For amplification of SEQ ID NO: 17
pk063F
                                          (SEQ ID NO: 65)
(5'-ATGGCGCGCCATGGAGAAAGTGACCAACTCAGACT-3')

pk063R
                                          (SEQ ID NO: 66)
(5'-GCTTAATTAATTCAACGGTAGAGACGGTATGTGGG-3')

For amplification of SEQ ID NO: 19
pk064F
                                          (SEQ ID NO: 67)
(5'-ATGGCGCGCCAGAAAAAAGCAATGGCGTCAGAC-3')

pk064R
                                          (SEQ ID NO: 68)
(5'-GCTTAATTAACTCACAGCTTTCCCTTATCTTTCC-3')

For amplification of SEQ ID NO: 21
pk073F
                                          (SEQ ID NO: 69)
(5'-ATGGCGCGCCGCCAGAGGACGAGACAAGGGG-3')

pk073R
                                          (SEQ ID NO: 70)
(5'-GCTTAATTAACCATTGGGGATGGTCTAAGTTTCC-3')

For amplification of SEQ ID NO: 23
pk082F
                                          (SEQ ID NO: 71)
(5'-ATGGCGCGCCATGGAAGGTGGAGCTGCTCTC-3')

pk082R
```

```
                                                      (SEQ ID NO: 72)
(5'-GCTTAATTAAGCCAAATAAAGACAGATCGAGGG-3')

For amplification of SEQ ID NO: 25
pk084F
                                                      (SEQ ID NO: 73)
(5'-ATGGCGCGCCATGGGGTCATCACAGTCTTCGC-3')

pk084R
                                                      (SEQ ID NO: 74)
(5'-GCTTAATTAATCAATAGTGTAGAAACCTAACAAGTATTGG-3')

For amplification of SEQ ID NO: 27
pk086F
                                                      (SEQ ID NO: 75)
(5'-ATGGCGCGCCCAAGGGGGGTCTCTGTCGGTTC-3')

pk086R
                                                      (SEQ ID NO: 76)
(5'-GCTTAATTAACATCATCATTGCTCTCCAAACCC-3')

For amplification of SEQ ID NO: 29
pk088F
                                                      (SEQ ID NO: 77)
(5'-ATGGCGCGCCGAGAAGAAGAATCAAAATCCCACACA-3')

pk088R
                                                      (SEQ ID NO: 78)
(5'-GCTTAATTAAGCGATAGATCGAATAAAAGGACCA-3')

For amplification of SEQ ID NO: 31
pk095F
                                                      (SEQ ID NO: 79)
(5'-ATGGCGCGCCCCTTCTTGATTCGTCCTCTCCACT-3')

pk095R
                                                      (SEQ ID NO: 80)
(5'-GCTTAATTAACCACCATCTCCTCCGATTCTCTTC-3')

For amplification of SEQ ID NO: 33
pk096F
                                                      (SEQ ID NO: 81)
(5'-ATGGCGCGCCATGGTTAAAGAAATAGCTTCTTGGTT-3')

pk096R
                                                      (SEQ ID NO: 82)
(5'-GCTTAATTAATTAGAGAAGTTGGTCAGCTTGCAAC-3')

For amplification of SEQ ID NO: 35
pk097F
                                                      (SEQ ID NO: 83)
(5'-ATGGCGCGCCATGGAAGTCTGCAATTGTATTGAACC-3')

pk097R
                                                      (SEQ ID NO: 84)
(5'-GCTTAATTAATTACATGCCCTCGTACAGTACCCG-3')

For amplification of SEQ ID NO: 37
pk097F
                                                      (SEQ ID NO: 85)
(5'-ATGGCGCGCCATGGAAGTCTGCAATTGTATTGAACC-3')

pk097R
                                                      (SEQ ID NO: 86)
(5'-GCTTAATTAATTACATGCCCTCGTACAGTACCCG-3')

For amplification of SEQ ID NO: 39
pk098F
                                                      (SEQ ID NO: 87)
(5'-ATGGCGCGCCATGATGGGCAGTGTCGAGCTG-3')

pk098R
                                                      (SEQ ID NO: 88)
(5'-GCTTAATTAATCAAGCTCTGCTCTTGCACTTCT-3')

For amplification of SEQ ID NO: 41
Pk099F
                                                      (SEQ ID NO: 89)
(5'-ATGGCGCGCCATGATCGGCCAACTTATGAACCT-3')

pk099R
                                                      (SEQ ID NO: 90)
(5'-GCTTAATTAATCAAGATCTGTTCTTGCAGTACTTCTC-3')

For amplification of SEQ ID NO: 43
Pk100F
                                                      (SEQ ID NO: 91)
(5'-ATGGCGCGCCGGAGAAAATAGTTAGCTTTGGTCGG-3')

pk100R
                                                      (SEQ ID NO: 92)
(5'-GCTTAATTAACCAAACGAGTGGTGCAATTACAC-3')

For amplification of SEQ ID NO: 45
Pk105F
                                                      (SEQ ID NO: 93)
(5'-ATGGCGCGCCATGGAGGAAGTATCTCCGGCGATC-3')

pk105R
                                                      (SEQ ID NO: 94)
(5'-GCTTAATTAATCAGTTCAAGGGTTTGCTCTTGAG-3')

For amplification of SEQ ID NO: 47
Pk107F
                                                      (SEQ ID NO: 95)
(5'-ATGGCGCGCCATGGAAATGCCCGGTAGAAGATC-3')

pk107R
                                                      (SEQ ID NO: 96)
(5'-GCTTAATTAATTACAAATCCGAGCGGTTGGGCG-3')
```

Example 7

*Agrobacterium* Mediated Plant Transformation

For plant transformation, binary vectors such as pBinAR can be used (Höfgen & Willmitzer 1990, Plant Sci. 66: 221-230). Plant binary vectors encoding LMP genes were constructed with the aim to achieve the overexpression of functionally active proteins in transgenic plants. All LMP gene candidates were cloned into the plant binary vector pBPS-GB 1 vector. The binary vector contains a selectable marker gene driven under the control of the AtAct2-I promoter (Ann Y-Q et al., 1996, Plant Journal 10:107-121) and a USP (unknown seed protein, Bäumlein et al., Mol Gen Genet. 225: 459-467, 1991) seed-specific promoter driving the candidate LMP gene with the NOSpA terminator. Full-length LMP cDNA were cloned into AscI and PacI restriction sites in the multiple cloning site of pBPS-GB 1 in sense orientation behind the USP seed-specific promoter. The recombinant binary vectors (based on pBPS-GB1) containing the genes of interest were transformed into *E. coli* Top10 cells (Invitrogen) using standard conditions. Transformed cells were selected for on LB agar containing an antibiotic and grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al. 1989, Molecular Cloning, A Laboratory Manual. $2^{nd}$ Edition. Cold Spring Harbor Laboratory Press. Cold Spring Harbor, N.Y.). The nucleotide sequence of the inserted LMP genes was verified by "2+1" sequencing (the insert DNA was sequence by determining the nucleotide sequence of one DNA stand with two independent sequence reactions and the complementary DNA strand with on sequencing reaction according to the Bermuda convention). The full length sequences are shown as SEQ ID NOs: 1, 3, 5, 7, 9, 11, 13, 15, 17, 19, 21, 23, 25, 27, 29, 31, 33, 35, 37, 39, 41, 43, 45 and 47.

Agrobacterium mediated plant transformation with binary vectors encoding the LMP nucleic acids described herein was performed using standard transformation and regeneration techniques (Gelvin, Stanton B. & Schilperoort R.A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993).

The *Agrobacterium* mediated transformation of *Arabidopsis thaliana* was performed using the GV3 (pMP90) (Koncz & Schell, 1986, Mol. Gen. Genet. 204: 383-396) *Agrobacterium tumefaciens* strain. *Arabidopsis thaliana* ecotype Col-2 was grown and transformed according to standard conditions (Bechtold 1993, Acad. Sci. Paris. 316: 1194-1199; Bent et al. 1994, Science 265: 1856-1860). Kanamycin was used as antibiotic selection marker for *Agrobacterium* transformation. The presence and correct orientation of the LMP-encoding binary vectors in *Agrobacterium* cultures was verified by PCR using the LMP gene-specific primers described in example 6. For the plant transformation flowering *Arabidopsis* plants were dipped into the recombinant *Agrobacterium* cultures and allowed to go to seed. Transgenic *Arabidopsis* T1 plants were identified by growing the seeds on Petri plates containing the selection agent appropriate for the selection marker present on the T-DNA. Surviving healthy seedlings were transferred to soil and grown in a growth chamber under controlled conditions. T2 seeds were harvested from these Ti plants. The transgenic lines were propagated through successive generations and T2, T3 and T4 seeds were obtained. The segregation ratio of the presence or absence of the T-DNA was monitored in order to determine whether the lines contained single-locus or multi-locus insertions and whether the lines were homozygous or heterozygous for the T-DNA insertion. T2, T3 and T4 seeds were analyzed for seed oil content (see also example 8).

*Agrobacterium* mediated plant transformation is also applicable to *Brassica* and other crops. In particular, seeds of canola are surface sterilized with 70% ethanol for 4 minutes at room temperature with continuous shaking, followed by 20% (v/v) CLOROX supplemented with 0.05% (v/v) TWEEN for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige & Skoog 1962, Physiol. Plant. 15: 473-497) medium supplemented with 100 µM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced *Agrobacterium* suspension culture. (The imbibition of dry embryos with a culture of *Agrobacterium* is also applicable to maize embryo axes). The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the agrobacteria. The liquid medium is used to moisten the sterile filter paper. The embryos are incubated during 4 weeks at 25° C., under 440 µmol m$^{-2}$ sec$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 µmol m$^{-2}$ s$^{-1}$ light intensity and 12 h photoperiod for about 80 days.

Samples of the primary transgenic plants ($T_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR, and used as recommended by the manufacturer.

Transformation of soybean can be performed using for example a technique described in EP 424 047, U.S. Pat. No. 5,322,783 (Pioneer Hi-Bred International) or in EP 0397 687, U.S. Pat. No. 5,376,543 or U.S. Pat. No. 5,169,770 (University Toledo). Soybean seeds are surface sterilized with 70% ethanol for 4 minutes at room temperature with continuous shaking, followed by 20% (v/v) CLOROX supplemented with 0.05% (v/v) TWEEN for 20 minutes with continuous shaking. Then the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

Example 8

Analysis of the Impact of Recombinant LMPs on the Production of a Desired Seed Storage Compound: Fatty Acid Production The total fatty acid content of *Arabidopsis* seeds was determined by saponification of seeds in 0.5 M KOH in methanol at 80° C. for 2 h followed by LC-MS analysis of the free fatty acids. Total fatty acid content of seeds of control and transgenic plants was measured with bulked seeds (usually 5 mg seed weight) of a single plant. Three different types of controls have been used: Col-2 (Columbia-2, the *Arabidopsis* ecotypes LMP gene of interest have been transformed in), C-24 (an *Arabidopsis* ecotype found to accumulate high amounts of total fatty acids in seeds) and BPS empty (without LMP gene of interest) binary vector construct. The controls indicated in the tables below have been grown side by side with the transgenic lines. Differences in the total values of the controls are explained either by differences in the growth conditions, which were found to be very sensitive to small variations in the plant cultivation, or by differences in the standards added to quantify the fatty acid content. Because of the seed bulking all values obtained with T2 seeds and in part also with T3 seeds are the result of a mixture of homozygous (for the gene of interest) and heterozygous events, implying that these data underestimate the LMP gene effect.

TABLE 6

Determination of the T2 seed total fatty acid content of transgenic lines of pk002b (containing SEQ ID NO: 1). Shown are the means (± standard deviation). (Average mean values are shown ± standard deviation, number of individual measurements per plant line: 12-18; Col-2 is the Arabidopsis ecotype the LMP gene has been transformed in, C-24 is a high-oil *Arabidopsis* ecotype used as another control)

| Genotype | g total fatty acids/g seed weight |
| --- | --- |
| C-24 wild-type seeds | 0.513 ± 0.042 |
| Col-2 wild-type seeds | 0.462 ± 0.053 |
| pk002b transgenic seeds | 0.487 ± 0.047 |

TABLE 7

Determination of the T2 seed total fatty acid content of transgenic lines of pk020b (containing SEQ ID NO: 3). Shown are the means (± standard deviation) of 10 (Col-2) and ~9 (pk020b) individual plants, respectively.

| Genotype | g total fatty acids/g seed weight |
| --- | --- |
| Col-2 wild-type seeds | 0.353 ± 0.045 |
| pk020b transgenic seeds | 0.402 ± 0.050 |

TABLE 8

Determination of the T2 seed total fatty acid content of transgenic lines of pk033 (containing SEQ ID NO: 5). Shown are the means (± standard deviation) of 9 (Col-2) and 18 (pk033) individual plants, respectively.

| Genotype | g total fatty acids/g seed weight |
| --- | --- |
| Col-2 wild-type seeds | 0.481 ± 0.034 |
| Pk033 transgenic seeds | 0.507 ± 0.047 |

TABLE 9

Determination of the T2 seed total fatty acid content of transgenic lines of pk037 (containing SEQ ID NO: 7). Shown are the means (± standard deviation) of 10 (Col-2) and 19 (pk037) individual plants, respectively.

| Genotype | g total fatty acids/g seed weight |
| --- | --- |
| Col-2 wild-type seeds | 0.301 ± 0.028 |
| pk037 transgenic seeds | 0.328 ± 0.026 |

TABLE 10

Determination of the T2 seed total fatty acid content of transgenic lines of pk038 (containing SEQ ID NO: 9). Shown are the means (± standard deviation) of 12-20 individual plants per line.

| Genotype | g total fatty acids/g seed weight |
| --- | --- |
| C-24 wild-type seeds | 0.366 ± 0.025 |
| Col-2 wild-type seeds | 0.319 ± 0.026 |
| Pk038 transgenic seeds | 0.382 ± 0.028 |

TABLE 11

Determination of the T2 seed total fatty acid content of transgenic lines of pk053b (containing SEQ ID NO: 13). Shown are the means (± standard deviation) of 13-19 individual plants per line.

| Genotype | g total fatty acids/g seed weight |
| --- | --- |
| Col-2 wild-type seeds | 0.483 ± 0.040 |
| C-24 wild-type seeds | 0.483 ± 0.040 |
| pk053b transgenic seeds | 0.472 ± 0.042 |

TABLE 12

Determination of the T2 seed total fatty acid content of transgenic lines of pk060 (containing SEQ ID NO: 15). Shown are the means (± standard deviation) of 14-18 individual plants per line.

| Genotype | g total fatty acids/g seed weight |
| --- | --- |
| Col-2 wild-type seeds | 0.406 ± 0.047 |
| pk060 transgenic seeds | 0.435 ± 0.034 |

TABLE 13

Determination of the T2 seed total fatty acid content of transgenic lines of pk063b (containing SEQ ID NO: 17). Shown are the means (± standard deviation) of 16-19 individual plants per line.

| Genotype | g total fatty acids/g seed weight |
| --- | --- |
| Col-2 wild-type seeds | 0.466 ± 0.036 |
| C-24 wild-type seeds | 0.485 ± 0.046 |
| pk063b transgenic seeds | 0.480 ± 0.064 |

TABLE 14

Determination of the T2 seed total fatty acid content of transgenic lines of pk064 (containing SEQ ID NO: 19). Shown are the means (± standard deviation) of 15-19 individual plants per line.

| Genotype | g total fatty acids/g seed weight |
| --- | --- |
| Col-2 wild-type seeds | 0.466 ± 0.036 |
| C-24 wild-type seeds | 0.485 ± 0.046 |
| pk064 transgenic seeds | 0.480 ± 0.055 |

TABLE 15

Determination of the T2 seed total fatty acid content of transgenic lines of pk073 (containing SEQ ID NO: 21). Shown are the means (± standard deviation) of 13-17 individual plants per line.

| Genotype | g total fatty acids/g seed weight |
| --- | --- |
| C-24 wild-type seeds | 0.513 ± 0.042 |
| Col-2 wild-type seeds | 0.462 ± 0.053 |
| pk073 transgenic seeds | 0.498 ± 0.035 |

TABLE 16a

Determination of the T2 seed total fatty acid content of transgenic lines of pk082 (containing SEQ ID NO: 23). Shown are the means (± standard deviation) of 14-19 individual plants per line.

| Genotype | g total fatty acids/g seed weight |
|---|---|
| C-24 wild-type seeds | 0.377 ± 0.041 |
| Col-2 wild-type seeds | 0.358 ± 0.028 |
| pk082 transgenic seeds | 0.381 ± 0.029 |

TABLE 16b

Determination of the T3 seed total fatty acid content of transgenic lines of pk082 (containing SEQ ID NO: 23). Shown are the means (± standard deviation) of 14-19 individual plants per line.

| Genotype | g total fatty acids/g seed weight |
|---|---|
| C-24 wild-type seeds | 0.351 ± 0.026 |
| Col-2 wild-type seeds | 0.326 ± 0.036 |
| pk082-4 transgenic seeds | 0.351 ± 0.021 |
| pk082-10 transgenic seeds | 0.361 ± 0.027 |
| pk082-11 transgenic seeds | 0.342 ± 0.032 |
| pk082-12 transgenic seeds | 0.335 ± 0.019 |

TABLE 17

Determination of the T2 seed total fatty acid content of transgenic lines of pk084 (containing SEQ ID NO: 25). Shown are the means (± standard deviation) of 12-18 individual plants per line.

| Genotype | g total fatty acids/g seed weight |
|---|---|
| C-24 wild-type seeds | 0.377 ± 0.041 |
| Col-2 wild-type seeds | 0.358 ± 0.028 |
| pk084 transgenic seeds | 0.372 ± 0.042 |

TABLE 18

Determination of the T2 seed total fatty acid content of transgenic lines of pk086 (containing SEQ ID NO: 27). Shown are the means (± standard deviation) of 14-20 individual plants per line.

| Genotype | g total fatty acids/g seed weight |
|---|---|
| C-24 wild-type seeds | 0.496 ± 0.049 |
| Col-2 wild-type seeds | 0.443 ± 0.036 |
| Pk086 transgenic seeds | 0.472 ± 0.049 |

TABLE 19

Determination of the T2 seed total fatty acid content of transgenic lines of pk088 (containing SEQ ID NO: 29). Shown are the means (± standard deviation) of 14-20 individual plants per line.

| Genotype | g total fatty acids/g seed weight |
|---|---|
| C-24 wild-type seeds | 0.466 ± 0.033 |
| Col-2 wild-type seeds | 0.372 ± 0.045 |
| Pk088 transgenic seeds | 0.448 ± 0.015 |

TABLE 20

Determination of the T2 seed total fatty acid content of transgenic lines of pk095 (containing SEQ ID NO: 31). Shown are the means (± standard deviation) of 14-20 individual plants per line.

| Genotype | g total fatty acids/g seed weight |
|---|---|
| C-24 wild-type seeds | 0.439 ± 0.036 |
| Col-2 wild-type seeds | 0.419 ± 0.034 |
| Pk095 transgenic seeds | 0.442 ± 0.037 |

TABLE 21

Determination of the T2 seed total fatty acid content of transgenic lines of pk096 (containing SEQ ID NO: 33). Shown are the means (± standard deviation) of 11-19 individual plants per line.

| Genotype | g total fatty acids/g seed weight |
|---|---|
| C-24 wild-type seeds | 0.496 ± 0.049 |
| Col-2 wild-type seeds | 0.443 ± 0.036 |
| Pk096 transgenic seeds | 0.472 ± 0.039 |

TABLE 22

Determination of the T2 seed total fatty acid content of transgenic lines of pk097a (containing SEQ ID NO: 35). Shown are the means (± standard deviation) of 14-18 individual plants per line.

| Genotype | g total fatty acids/g seed weight |
|---|---|
| C-24 wild-type seeds | 0.513 ± 0.042 |
| Col-2 wild-type seeds | 0.462 ± 0.053 |
| Pk097a transgenic seeds | 0.506 ± 0.034 |

TABLE 23

Determination of the T2 seed total fatty acid content of transgenic lines of pk097b (containing SEQ ID NO: 37). Shown are the means (± standard deviation) of 14-18 individual plants per line.

| Genotype | g total fatty acids/g seed weight |
|---|---|
| C-24 wild-type seeds | 0.513 ± 0.042 |
| Col-2 wild-type seeds | 0.462 ± 0.053 |
| Pk097b transgenic seeds | 0.506 ± 0.034 |

TABLE 24

Determination of the T2 seed total fatty acid content of transgenic lines of pk098 (containing SEQ ID NO: 39). Shown are the means (± standard deviation) of 12-19 individual plants per line.

| Genotype | g total fatty acids/g seed weight |
|---|---|
| C-24 wild-type seeds | 0.513 ± 0.042 |
| Col-2 wild-type seeds | 0.462 ± 0.053 |
| Pk098 transgenic seeds | 0.489 ± 0.027 |

TABLE 25

Determination of the T2 seed total fatty acid content of transgenic lines of pk099 (containing SEQ ID NO: 41). Shown are the means (± standard deviation) of 11-20 individual plants per line.

| Genotype | g total fatty acids/g seed weight |
| --- | --- |
| C-24 wild-type seeds | 0.496 ± 0.049 |
| Col-2 wild-type seeds | 0.443 ± 0.036 |
| Pk099 transgenic seeds | 0.492 ± 0.034 |

TABLE 26

Determination of the T2 seed total fatty acid content of transgenic lines of pk105 (containing SEQ ID NO: 45). Shown are the means (± standard deviation) of 14-20 individual plants per line.

| Genotype | g total fatty acids/g seed weight |
| --- | --- |
| C-24 wild-type seeds | 0.439 ± 0.036 |
| Col-2 wild-type seeds | 0.419 ± 0.034 |
| pp84 transgenic seeds | 0.442 ± 0.037 |

TABLE 27a

Determination of the T2 seed total fatty acid content of transgenic lines of pk107 (containing SEQ ID NO: 47). Shown are the means (± standard deviation) of 14-20 individual plants per line.

| Genotype | g total fatty acids/g seed weight |
| --- | --- |
| C-24 wild-type seeds | 0.496 ± 0.049 |
| Col-2 wild-type seeds | 0.443 ± 0.036 |
| Pk107 transgenic seeds | 0.492 ± 0.059 |

TABLE 27b

Determination of the T3 seed total fatty acid content of transgenic lines of pk107 (containing SEQ ID NO: 47). Shown are the means (± standard deviation) of 18-30 individual plants per line.

| Genotype | g total fatty acids/g seed weight |
| --- | --- |
| C-24 wild-type seeds | 0.371 ± 0.025 |
| Col-2 wild-type seeds | 0.321 ± 0.028 |
| Pk107-10 transgenic seeds | 0.375 ± 0.023 |
| Pk107-14 transgenic seeds | 0.383 ± 0.023 |
| Pk107-17 transgenic seeds | 0.399 ± 0.024 |

Example 9

Analysis of the Impact of Recombinant Proteins on the Production of a Desired Seed Storage Compound The effect of the genetic modification in plants on a desired seed storage compound (such as a sugar, lipid or fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman 1985, Encyclopedia of Industrial Chemistry, vol. A2, pp. 89-90 and 443-613, VCH: Weinheim; Fallon, A. et al. 1987, Applications of HPLC in Biochemistry in: Laboratory Techniques in Biochemistry and Molecular Biology, vol. 17; Rehm et al., 1993 Product recovery and purification, Biotechnology, vol. 3, Chapter III, pp. 469-714, VCH: Weinheim; Better, P. A. et al., 1988 Bioseparations: downstream processing for biotechnology, John Wiley & Sons; Kennedy J. F. & Cabral J. M. S. 1992, Recovery processes for biological materials, John Wiley and Sons; Shaeiwitz J. A. & Henry J. D. 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad. Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland:Oily Press.—(Oily Press Lipid Library; Christie, William W., Gas Chromatography and Lipids. A Practical Guide—Ayr, Scotland:Oily Press, 1989 Repr. 1992.—IX,307 S.—(Oily Press Lipid Library; and "Progress in Lipid Research, Oxford:Pergamon Press, 1 (1952)-16 (1977) Progress in the Chemistry of Fats and Other Lipids CODEN.

Unequivocal proof of the presence of fatty acid products can be obtained by the analysis of transgenic plants following standard analytical procedures: GC, GC-MS or TLC as variously described by Christie and references therein (1997 in: Advances on Lipid Methodology 4th ed.: Christie, Oily Press, Dundee, pp. 119-169; 1998). Detailed methods are described for leaves by Lemieux et al. (1990, Theor. Appl. Genet. 80:234-240) and for seeds by Focks & Benning (1998, Plant Physiol. 118:91-101)

Positional analysis of the fatty acid composition at the C-1, C-2 or C-3 positions of the glycerol backbone is determined by lipase digestion (see, e.g., Siebertz & Heinz 1977, Z. Naturforsch. 32c:193-205, and Christie 1987, Lipid Analysis $2^{nd}$ Edition, Pergamon Press, Exeter, ISBN 0-08-023791-6).

A typical way to gather information regarding the influence of increased or decreased protein activities on lipid and sugar biosynthetic pathways is for example via analyzing the carbon fluxes by labeling studies with leaves or seeds using $^{14}$C-acetate or $^{14}$C-pyruvate (see, e.g. Focks & Benning 1998, Plant Physiol. 118:91-101; Eccleston & Ohlrogge 1998, Plant Cell 10:613-621). The distribution of carbon-14 into lipids and aqueous soluble components can be determined by liquid scintillation counting after the respective separation (for example on TLC plates) including standards like $^{14}$C-sucrose and $^{14}$C-malate (Eccleston & Ohlrogge 1998, Plant Cell 10:613-621).

Material to be analyzed can be disintegrated via sonification, glass milling, liquid nitrogen and grinding or via other applicable methods. The material has to be centrifuged after disintegration. The sediment is re-suspended in distilled water, heated for 10 minutes at 100° C., cooled on ice and centrifuged again followed by extraction in 0.5 M sulfuric acid in methanol containing 2% dimethoxypropane for 1 hour at 90° C. leading to hydrolyzed oil and lipid compounds resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 min. at 240° C. The identity of resulting fatty acid methylesters is defined by the use of standards available form commercial sources (i.e., Sigma).

In case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt M., Lilley R. Mc. C., Gerhardt R. and Heldt M. W. (1989, "Determination of metabolite levels in specific cells and subcellular compartments of plant leaves" Methods Enzymol. 174:518-552; for other methods see also Härtel et al. 1998, Plant Physiol. Biochem. 36:407-417 and Focks & Benning 1998, Plant Physiol. 118:91-101).

For the extraction of soluble sugars and starch, 50 seeds are homogenized in 500 μl of 80% (v/v) ethanol in a 1.5-ml polypropylene test tube and incubated at 70° C. for 90 min. Following centrifugation at 16,000 g for 5 min, the supernatant is transferred to a new test tube. The pellet is extracted twice with 500 μl of 80% ethanol. The solvent of the combined supernatants is evaporated at room temperature under a vacuum. The residue is dissolved in 50 μl of water, representing the soluble carbohydrate fraction. The pellet left from the ethanol extraction, which contains the insoluble carbohydrates including starch, is homogenized in 200 μl of 0.2 N KOH, and the suspension is incubated at 95° C. for 1 h to dissolve the starch. Following the addition of 35 μl of 1 N acetic acid and centrifugation for 5 mM at 16,000 g, the supernatant is used for starch quantification.

To quantify soluble sugars, 10 μl of the sugar extract is added to 990 μl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose and sucrose, 4.5 units of hexokinase, 1 unit of phosphoglucoisomerase, and 2 μl of a saturated fructosidase solution are added in succession. The production of NADPH is photometrically monitored at a wavelength of 340 nm. Similarly, starch is assayed in 30 μl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding" Anal. Biochem. 72:248-254). For quantification of total seed protein, 15-20 seeds are homogenized in 250 μl of acetone in a 1.5-ml polypropylene test tube. Following centrifugation at 16,000 g, the supernatant is discarded and the vacuum-dried pellet is resuspended in 250 μl of extraction buffer containing 50 mM Tris-HCl, pH 8.0, 250 mM NaCl, 1 mM EDTA, and 1% (w/v) SDS. Following incubation for 2 h at 25° C., the homogenate is centrifuged at 16,000 g for 5 mM and 200 ml of the supernatant will be used for protein measurements. In the assay, ☐-globulin is used for calibration. For protein measurements, Lowry DC protein assay (Bio-Rad) or Bradford-assay (Bio-Rad) are used.

Enzymatic assays of hexokinase and fructokinase are performed spectrophotometrically according to Renz et al. (1993, Planta 190:156-165), of phosphoglucoisomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase and pyruvate kinase are performed according to Burrell et al. (1994, Planta 194:95-101) and of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Härtel et al. (1998, Plant Physiol. Biochem. 36:407-417) and metabolites are measured as described in Jelitto et al. (1992, Planta 188:238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (Fiehn et al. 2000, Nature Biotech. 18:1447-1161).

For example, yeast expression vectors comprising the nucleic acids disclosed herein, or fragments thereof, can be constructed and transformed into Saccharomyces cerevisiae using standard protocols. The resulting transgenic cells can then be assayed for alterations in sugar, oil, lipid or fatty acid contents.

Similarly, plant expression vectors comprising the nucleic acids disclosed herein, or fragments thereof, can be constructed and transformed into an appropriate plant cell such as *Arabidopsis*, soybean, rape, maize, wheat, *Medicago truncatula*, etc., using standard protocols. The resulting transgenic cells and/or plants derived therefrom can then be assayed for alterations in sugar, oil, lipid or fatty acid contents.

Additionally, the sequences disclosed herein, or fragments thereof, can be used to generate knockout mutations in the genomes of various organisms, such as bacteria, mammalian cells, yeast cells, and plant cells (Girke at al. 1998, Plant J. 15:39-48). The resultant knockout cells can then be evaluated for their composition and content in seed storage compounds, and the effect on the phenotype and/or genotype of the mutation. For other methods of gene inactivation include U.S. Pat. No. 6,004,804 "Non-Chimeric Mutational Vectors" and Puttaraju et al. (1999, "Spliceosome-mediated RNA trans-splicing as a tool for gene therapy" Nature Biotech. 17:246-252).

Example 10

Northern-Hybridization

For RNA hybridization, 20 μg of total RNA or 1 μg of poly-(A)+ RNA is separated by gel electrophoresis in 1.25% strength agarose gels using formaldehyde as described in Amasino (1986, Anal. Biochem. 152:304), transferred by capillary attraction using 10×SSC to positively charged nylon membranes (Hybond N+, Amersham, Braunschweig), immobilized by UV light and pre-hybridized for 3 hours at 68° C. using hybridization buffer (10% dextran sulfate w/v, 1 M NaCl, 1% SDS, 100 μg/ml of herring sperm DNA). The labeling of the DNA probe with the Highprime DNA labeling kit (Roche, Mannheim, Germany) is carried out during the pre-hybridization using alpha-$^{32}$P dCTP (Amersham, Braunschweig, Germany). Hybridization is carried out after addition of the labeled DNA probe in the same buffer at 68° C. overnight. The washing steps are carried out twice for 15 min using 2×SSC and twice for 30 min using 1×SSC, 1% SDS at 68° C. The exposure of the sealed filters is carried out at −70° C. for a period of 1 day to 14 days.

Example 11

DNA Sequencing and Computational Functional Analysis of SSH Library

The SSH cDNA library as described in Examples 4 and 5 was used for DNA sequencing according to standard methods, in particular by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown E. coli cultures grown in Luria-Broth medium containing ampicillin (see Sambrook et al. (1989, Cold Spring Harbor Laboratory Press: ISBN 0-87969-309-6) on a Qiagene DNA preparation robot (Qiagen, Hilden) according to the manufacturer's protocols). Sequencing primers with the following nucleotide sequences were used:

```
                                          (SEQ ID NO: 97)
5'-CAGGAAACAGCTATGACC-3'

(SEQ ID NO: 98)
5'-CTAAAGGGAACAAAAGCTG-3'

(SEQ ID NO: 99)
5'-TGTAAAACGACGGCCAGT-3'
```

Sequences were processed and annotated using the software package EST-MAX commercially provided by Bio-Max (Munich, Germany). The program incorporates practically all bioinformatics methods important for functional and structural characterization of protein sequences. For reference see webpage at pedant.mips.biochem.mpg.de.

The most important algorithms incorporated in EST-MAX are: FASTA: Very sensitive protein sequence database searches with estimates of statistical significance (Pearson W. R. 1990, Rapid and sensitive sequence comparison with FASTP and FASTA. Methods Enzymol. 183:63-98). BLAST: Very sensitive protein sequence database searches with estimates of statistical significance (Altschul S. F., Gish W., Miller W., Myers E. W. and Lipman D. J. Basic local alignment search tool. J. Mol. Biol. 215:403-410). PREDATOR: High-accuracy secondary structure prediction from single and multiple sequences. (Frishman & Argos 1997, 75% accuracy in protein secondary structure prediction. Proteins 27:329-335). CLUSTALW: Multiple sequence alignment (Thompson, J. D., Higgins, D. G. and Gibson, T. J. 1994, CLUSTAL W: improving the sensitivity of progressive multiple sequence alignment through sequence weighting, positions-specific gap penalties and weight matrix choice, Nucleic Acids Res. 22:4673-4680). TMAP: Transmembrane region prediction from multiply aligned sequences (Persson B. & Argos P. 1994, Prediction of transmembrane segments in proteins utilizing multiple sequence alignments, J. Mol. Biol. 237:182-192). ALOM2:Transmembrane region prediction from single sequences (Klein P., Kanehisa M., and DeLisi C. 1984, Prediction of protein function from sequence properties: A discriminant analysis of a database. Biochim. Biophys. Acta 787:221-226. Version 2 by Dr. K. Nakai). PROSE-ARCH: Detection of PROSITE protein sequence patterns. Kolakowski L. F. Jr., Leunissen J. A. M. and Smith J. E. 1992, ProSearch: fast searching of protein sequences with regular expression patterns related to protein structure and function. Biotechniques 13:919-921). BLIMPS: Similarity searches against a database of ungapped blocks (Wallace & Henikoff 1992, PATMAT:A searching and extraction program for sequence, pattern and block queries and databases, CABIOS 8:249-254. Written by Bill Alford).

Example 12

In Vivo Mutagenesis

In vivo mutagenesis of microorganisms can be performed by incorporation and passage of the plasmid (or other vector) DNA through E. coli or other microorganisms (e.g. Bacillus spp. or yeasts such as Saccharomyces cerevisiae) which are impaired in their capabilities to maintain the integrity of their genetic information. Typical mutator strains have mutations in the genes for the DNA repair system (e.g., mutHLS, mutD, mutT, etc.; for reference, see Rupp W. D. 1996, DNA repair mechanisms, in: Escherichia coli and Salmonella, p. 2277-2294, ASM: Washington.) Such strains are well known to those skilled in the art. The use of such strains is illustrated, for example, in Greener and Callahan 1994, Strategies 7:32-34. Transfer of mutated DNA molecules into plants is preferably done after selection and testing in microorganisms. Transgenic plants are generated according to various examples within the exemplification of this document.

Example 13

Assessment of the mRNA Expression and Activity of a Recombinant Gene Product in the Transformed Organism The activity of a recombinant gene product in the transformed host organism can be measured on the transcriptional or/and on the translational level. A useful method to ascertain the level of transcription of the gene (an indicator of the amount of mRNA available for translation to the gene product) is to perform a Northern blot (for reference see, for example, Ausubel et al. 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (see, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar H. et al. 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 14

In Vitro Analysis of the Function of *Arabidopsis thaliana* Genes in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M. & Webb, B. C. 1979, Enzymes. Longmans: London; Fersht, (1985) Enzyme Structure and Mechanism. Freeman: New York; Walsh (1979) Enzymatic Reaction Mechanisms. Freeman: San Francisco; Price, N.C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

Those skilled in the art will recognize, or will be able to ascertain using no more than routine experimentation, many equivalents to the specific embodiments of the invention described herein. Such equivalents are intended to be encompassed by the following claims.

We claim:

1. A method of producing a transgenic plant having an increased level of a seed storage compound as compared to an untransformed wild type variety of the plant comprising, transforming a plant cell with an expression vector comprising a lipid metabolism protein (LMP) nucleic acid and generating from the plant cell the transgenic plant, wherein the nucleic acid encodes a polypeptide that functions as a modulator of a seed storage compound in the plant, and wherein the LMP nucleic acid comprises
   a) the polynucleotide sequence of SEQ ID NO: 23;
   b) a polynucleotide sequence encoding a polypeptide comprising the amino acid sequence of SEQ ID NO: 24;
   c) a polynucleotide sequence having at least 95% sequence identity with the polynucleotide sequence of a) or b) above;
   d) a polynucleotide sequence encoding a polypeptide comprising an amino acid sequence having at least 95% sequence identity with the sequence of SEQ ID NO: 24; or
   e) a polynucleotide sequence that hybridizes to the complement of the polynucleotide sequence of a) or b) above under stringent conditions which comprise hybridization in 6×SSC at about 45° C. followed by one or more washes in 0.2×SSC, 0.1% SDS at 50-65° C.

2. The method of claim 1, wherein the LMP nucleic acid comprises
   a) a polynucleotide having at least 95% sequence identity with the polynucleotide of a) or b); or
   b) a polynucleotide encoding a polypeptide comprising an amino acid sequence having at least 95% sequence identity with the sequence of SEQ ID NO: 24.

3. The method of claim 1, wherein the nucleic acid encodes a polypeptide that contains a DNA-binding domain.

4. The method of claim 3, wherein the nucleic acid encodes a polypeptide comprising the amino acid sequence of SEQ ID NO: 24.

5. A transgenic plant made by the method of claim 1, or progeny thereof, wherein the plant or progeny thereof has an increased level of a seed storage compound as compared to a corresponding wild type variety of the plant; and wherein the transgenic plant or progeny thereof comprise the recombinant LMP nucleic acid.

6. The transgenic plant of claim 5, wherein the plant is a dicotyledonous plant.

7. The transgenic plant of claim 5, wherein the plant is a monocotyledonous plant.

8. The transgenic plant of claim 5, wherein the plant is an oil producing species.

9. A seed produced by the transgenic plant of claim 5, wherein the seed comprises the recombinant LMP nucleic acid.

10. The method of claim 1, further comprising obtaining a plant, plant part or progeny thereof, wherein the plant, plant part or progeny thereof comprise the recombinant nucleic acid and the plant, plant part or progeny thereof have an increased level of a seed storage compound compared to a corresponding wild type variety of the plant.

11. The method of claim 10, wherein the seed storage compound comprises oil.

12. The method of claim 1, wherein the seed storage compound comprises oil.

13. A method of increasing a level of a seed storage compound in a plant or seed as compared to an untransformed wild type variety of the plant or seed comprising, providing a transgenic plant or seed in which a lipid metabolism protein (LMP) nucleic acid has been introduced, wherein the transgenic plant or seed has an increased level of a seed storage compound as compared to an untransformed wild type variety of the plant, wherein the LMP nucleic acid comprises
   a) the polynucleotide sequence of SEQ ID NO: 23;
   b) a polynucleotide sequence encoding the polypeptide of SEQ ID NO: 24;
   c) a polynucleotide sequence having at least 95% sequence identity with the polynucleotide sequence of a) or b) above;
   d) a polynucleotide sequence encoding a polypeptide comprising an amino acid sequence having at least 95% sequence identity with the sequence of SEQ ID NO: 24; or
   e) a polynucleotide sequence that hybridizes to the complement of the polynucleotide sequence of a) or b) above under stringent conditions which comprise hybridization in 6×SSC at about 45° C. followed by one or more washes in 0.2×SSC, 0.1% SDS at 50-65° C.

14. The method of claim 13, wherein the seed storage compound comprises oil.

15. A recombinant lipid metabolism protein (LMP) nucleic acid comprising a polynucleotide sequence encoding a polypeptide that functions as a modulator of a seed storage compound in a plant, wherein the polynucleotide is operably linked to a heterologous promoter, wherein the polynucleotide comprises
   a) the polynucleotide of SEQ ID NO: 23; or
   b) a polynucleotide encoding a polypeptide comprising the amino acid sequence of SEQ ID NO: 24.

16. An expression construct comprising the recombinant LMP nucleic acid of claim 15 operably linked to one or more regulatory sequences.

17. A transgenic plant cell, plant part, plant, or progeny thereof, comprising 1) the recombinant LMP nucleic acid of claim 15; or 2) an expression construct comprising the recombinant LMP nucleic acid operably linked to one or more regulatory sequences.

18. The transgenic plant of claim 17, wherein the plant or progeny thereof has an increased level of a seed storage compound compared to a corresponding wild type variety of the plant.

19. The transgenic plant of claim 18, wherein the seed storage compound comprises oil.

20. A transgenic seed comprising the recombinant LMP nucleic acid of claim 15, wherein the seed has an increased level of oil compared to a corresponding wild type variety of the seed.

* * * * *